(12) United States Patent
Vitti et al.

(10) Patent No.: US 11,071,780 B2
(45) Date of Patent: Jul. 27, 2021

(54) METHODS AND FORMULATIONS FOR TREATING VASCULAR EYE DISEASES USING AFLIBERCEPT AND NESVACUMAB

(71) Applicant: REGENERON PHARMACEUTICALS, INC., Tarrytown, NY (US)

(72) Inventors: Robert L. Vitti, Old Tappan, NJ (US); Kristine A. Erickson, Roxbury, CT (US); Karen W. Chu, White Plains, NY (US); Stanley J. Wiegand, Hopewell Junction, NY (US); Jingtai Cao, White Plains, NY (US); Ivan B. Lobov, New York, NY (US); Saurabh Wadhwa, Nanuet, NY (US); Kenneth S. Graham, Pleasant Valley, NY (US); Daniel Dix, LaGrangeville, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 125 days.

(21) Appl. No.: 16/235,221

(22) Filed: Dec. 28, 2018

(65) Prior Publication Data
US 2019/0117767 A1  Apr. 25, 2019

Related U.S. Application Data

(62) Division of application No. 15/370,896, filed on Dec. 6, 2016, now abandoned, which is a division of
(Continued)

(51) Int. Cl.
*A61K 39/395* (2006.01)
*A61K 38/18* (2006.01)
(Continued)

(52) U.S. Cl.
CPC ........ *A61K 39/3955* (2013.01); *A61K 9/0048* (2013.01); *A61K 38/179* (2013.01);
(Continued)

(58) Field of Classification Search
None
See application file for complete search history.

(56) References Cited

U.S. PATENT DOCUMENTS

7,087,411 B2   8/2006   Daly et al.
7,608,261 B2   10/2009  Furfine
(Continued)

FOREIGN PATENT DOCUMENTS

CN   102458471 A   5/2012
CN   102549015 A   7/2012
(Continued)

OTHER PUBLICATIONS

Daly et al., REGN910, a fully-human, Ang2-specific monoclonal antibody, inhibits tumor growth as a monotherapy and dramatically potentiates the effects of VEGF Trap (aflibercept), Proceedings of the 102nd Ann. Meeting Am. Assoc. Cancer Res.; Apr. 2-6, 2011; Cane. Res. 71(8 Suppl):Abst 3290, Apt. 2011.*
(Continued)

*Primary Examiner* — Claire Kaufman
(74) *Attorney, Agent, or Firm* — Karl Bozicevic; Bozicevic Field & Francis LLP

(57) ABSTRACT

The present invention provides methods for treating, preventing or reducing the severity of an eye disease. The methods of the present invention comprise administering to a subject in need thereof a therapeutic composition comprising an angiopoietin-2 (Ang-2) inhibitor such as an anti-Ang-2 antibody in combination with a vascular
(Continued)

endothelial growth factor (VEGF) antagonist (e.g., aflibercept).

9 Claims, 4 Drawing Sheets

Specification includes a Sequence Listing.

Related U.S. Application Data application No. 14/943,490, filed on Nov. 17, 2015, now abandoned.

(60) Provisional application No. 62/084,003, filed on Nov. 25, 2014, provisional application No. 62/147,232, filed on Apr. 14, 2015.

(51) Int. Cl.
| | |
|---|---|
| A61K 38/17 | (2006.01) |
| C07K 16/22 | (2006.01) |
| A61K 9/00 | (2006.01) |
| A61K 47/02 | (2006.01) |
| A61K 47/26 | (2006.01) |
| C07K 14/71 | (2006.01) |
| C07K 16/46 | (2006.01) |
| A61K 39/00 | (2006.01) |

(52) U.S. Cl.
CPC ........ A61K 39/39591 (2013.01); A61K 47/02 (2013.01); A61K 47/26 (2013.01); C07K 14/71 (2013.01); C07K 16/22 (2013.01); C07K 16/46 (2013.01); A61K 2039/505 (2013.01); A61K 2039/54 (2013.01); C07K 2317/21 (2013.01); C07K 2317/565 (2013.01); C07K 2317/76 (2013.01); C07K 2319/30 (2013.01); C07K 2319/32 (2013.01)

(56) References Cited

U.S. PATENT DOCUMENTS

| | | | |
|---|---|---|---|
| 8,268,314 | B2 | 9/2012 | Baehner et al. |
| 8,703,130 | B2 | 4/2014 | Baehner et al. |
| 8,980,268 | B2 | 3/2015 | Lowry |
| 8,987,420 | B2 | 3/2015 | Thurston et al. |
| 9,062,105 | B1 | 6/2015 | Clube |
| 9,265,827 | B2* | 2/2016 | Wiegand ............... A61P 13/12 |
| 9,365,646 | B2* | 6/2016 | Ghosh .................. A61P 27/02 |
| 9,402,898 | B2 | 8/2016 | Walsh |
| 9,650,444 | B2 | 5/2017 | Wiegand |
| 2011/0110932 | A1* | 5/2011 | Patel ...................... C07K 16/22 424/133.1 |
| 2012/0189635 | A1 | 7/2012 | Thurston et al. |
| 2013/0129722 | A1 | 5/2013 | Lowy et al. |
| 2013/0186797 | A1 | 7/2013 | Walsh |
| 2013/0295094 | A1 | 11/2013 | Yancopoulos |
| 2014/0017244 | A1 | 1/2014 | Duerr et al. |
| 2014/0323983 | A1 | 10/2014 | Furfine et al. |
| 2016/0159893 | A1* | 6/2016 | Burian ............... A61K 38/1709 606/4 |

FOREIGN PATENT DOCUMENTS

| | | |
|---|---|---|
| CN | 103533950 A | 1/2014 |
| EP | 2344537 | 1/2014 |
| JP | 2013-500970 A | 1/2013 |
| RU | 2432155 | 11/2017 |
| WO | WO 2005/072772 | 8/2005 |
| WO | WO 2007/089445 | 8/2007 |
| WO | WO 2007/149334 | 12/2007 |
| WO | WO 2010/136492 | 12/2010 |
| WO | WO 2011/014469 | 2/2011 |
| WO | WO 2011/117329 | 9/2011 |
| WO | WO 2012/097019 | 7/2012 |
| WO | WO 2013/112438 | 8/2013 |

OTHER PUBLICATIONS

NCI Drug Dictionary, Nesvascumab, Retrieved online from <URL:https://www.cancer.gov/publications/dictionaries/cancer-drug/def/nesvacumab>, Retrieved on Jul. 14, 2020, 2020.*
Daly et al., Angiopoietin-2 functions as a Tie2 agonist in tumor models, where it limits the effects of VEGF inhibition, Cane. Res. 73(1):1-11, Nov. 2012.*
Papadopoulos et al.,A phase 1b study of combined angiogenesis blockade with nesvacumab, a selective monoclonal antibody (MAb) to angiopoietin-2 (Ang2) and ziv-aflibercept in patients with advanced solid malignancies, J. Clin. Oncol. 32(15 Suppl.):2522, May 20, 2014.*
Boyer, D.S., Intravitreal nesvacumab+aflibercept in diabetic macular edema: The phase 2 RUBY trail, Invest. Ophthalmol. Vis. Sci. 59:3620, Jul. 2018.*
Avery et al., "Systemic pharmacokinetics following intravitreal injetions of ranibizumab, bevacizumab or aflibercept in patients with neovascular AMD" British Journal of Ophthalmology (Jul. 2014) 98(12):1636-1641.
Korobelnik et al., "Intravitreal Aflibercept for Diabetic Macular Edema" Ophthalmology (Jul. 2014) 121(11)2247-2254.
ClinicalTrials.gov.archive, Study of Intravitreal (IVT) REGN910-3 and IVT REGN910 in Patients With Either Neovacular ("Wet") Age Related Macular Degeneration (AMD) or Diabetic Macular Edema (DME) (Nov. 22, 2013), History of Changes for Study: NCT01997164, URL:https://clinicaltrials.gov/ct2/history/NCT01997164?V_1=View#StudyPageTop.
Ratner et al., "Next-generation AMD drugs to wed blockbusters" Nature Biotechnology (Aug. 2014) 32(8):701-702.
Cheung, Gemmy Chio Ming et al. "ARVO Annual Meeting Abstract: Dual Inhibition of angiopoietin-2 and vascular endothelial growth factor-A laser-induced choroidal neovascularization in a non-human primate model" Investigative Ophthalmology & Visual Science (Apr. 1, 2014) 55:1174.
Dixon et al., "VEGF Trap-Eye for the treatment of neurovascular age-related macular degeneration" Expert Opinion on Investigational Drugs, Informa Healthcare (Oct. 1, 2009) 18(10):1-8.
Hashizume et al., "Complementary Actions of Inhibitors of Angiopoietin-2 and VEGF on Tumor Angiogenesis and Growth" Cancer Research (Mar. 2010) 70(6):2213-2223.
Koenig et al. "Deep Sequencing-guided Design of a High Affinity Dual Specificity Antibody to Target Two Angiogenic Factors in Neovascular Age-related Macular Degeneration" Journal of Biological Chemistry, Sep. 4, 2015, vol. 290, No. 36. pp. 21773-21786.
Oliner et al. "AMG 386, a Selective Angiopoietin 1/2-Neutralizing Peptibody, Inhibits Angiogenesis in Models of Ocular Neovascular Diseases" Investigative Ophthalmology & Visual Science, Apr. 2012, vol. 53, No. 4, pp. 2170-2180.
Rennel et al. "A Human Neutralizing Antibody Specific to Ang-2 Inhibits Ocular Angiogenesis" 2011, Microcirculation, vol. 18, pp. 598-607.
Rubio et al. "Ocular Angiogenesis: Vascular Endothelial Growth Factor and Other Factors" Retinal Pharmacotherapeutics, 2016, vol. 55, pp. 28-37.
Subramian et al., "Effect of histidine oxidation on the loss of potency of a humanized monoclonal antibody," AAPD PharmSci, Supp 3(3), Abstract @ M2154, Oct. 2001.
Tuuminen et al. "Increased Intravitreal angiopoietin-2 levels in patients with retinal vein occlusion" Acta Ophthalmologica, 2014, pp. e164-e165.
Von Leithner et al., "ARVO Annual Meeting Abstract: Bispecific anti-VEGF/ANG2 antibody exhibits superior efficacy to vegF monotherapy in a model of spontaneous CNV" Investigative Ophthalmology & Visual Science (Apr. 1, 2014) 55:2356.
You et al. "Effects of laser photocoagulation on serum agiopoietin-1, agiopoietin-2, angiopoietin-1/angiopoietin-2 ratio,, and soluble angiopoietin receptor Tie-2 levels in type 2 diabetic patients with

(56) References Cited

OTHER PUBLICATIONS proliferative diabetic retinopathy." International Journal of Ophthalmology, vol. 7, No. 4, Aug. 18, 2014, pp. 648-653.

* cited by examiner

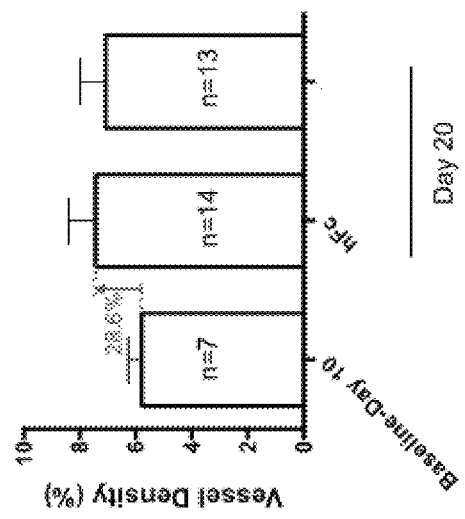
Figure 3 (Contd.)

METHODS AND FORMULATIONS FOR TREATING VASCULAR EYE DISEASES USING AFLIBERCEPT AND NESVACUMAB

FIELD OF THE INVENTION

The present invention relates to methods of treating or ameliorating at least one symptom or indication of a vascular eye disease comprising administering a pharmaceutical formulation comprising an angiopoietin-2 (Ang-2) inhibitor and a vascular endothelial growth factor (VEGF) antagonist to a subject in need thereof.

BACKGROUND

Vascular eye diseases are the leading cause of vision loss in today's aging population. These diseases are characterized by abnormal 'leaky' blood vessels growing into the retina. Two of the largest contributors to this patient population are diabetic retinopathy and exudative age-related macular degeneration.

Diabetic retinopathy (DR) is a major cause of visual impairment in the United States (Klein et al 1984, Ophthalmology 91:1464-1474; Moss et al 1998, Ophthalmology 105:998-1003). Diabetic retinopathy results from microvascular decompensation beginning with basement membrane thickening (Ruggiero et al 1997, Diabetes Metab. 23:30-42), and eventually leading to vascular occlusion and neovascularization (Porta et al 2002, Diabetologia. 45:1617-1634). It is estimated that about 28% of patients 40 years and older with diabetes have DR, and 4.4% have vision threatening DR (Zhang et al 2010, JAMA. 304: 649-656). Diabetic macular edema (DME) is a manifestation of DR and is the most frequent cause of blindness in young and mid-aged adults (Klein et al 1984, Ophthalmology 91:1464-1474; Moss et al 1998, Ophthalmology 105:998-1003).

Age-related macular degeneration (AMD) is the leading cause of severe visual loss in people aged 50 years or older in the developed world. In recent years, major advances have been made in the treatment of AMD, with the introduction of anti-angiogenic agents, offering hope of significant visual recovery for patients with neovascular AMD (Keane et al 2012, Sury Ophthalmol. 57: 389-414).

Anti-vascular endothelial growth factor (VEGF) therapy (e.g., aflibercept) is standard of care treatment for neovascular AMD and DME. The efficacy and safety of aflibercept in these patient populations is well-characterized (Dixon et al 2009; Expert Opin. Investig. Drugs 18: 1573-80). However, in AMD, although ~95% of patients maintained their vision, only approximately 30% of patients achieved an improvement of 15 or more letters in best corrected visual acuity (BCVA) at 1 year. In DME, there is also the possibility of improving treatment outcomes, as seen with aflibercept and with ranibizumab, less than 50% of patients with vision loss due to DME achieve a 15 or more letter improvement over 1 and 2 years. Also, in the studies with ranibizumab, clinical evidence of proliferative retinopathy developed in up to 7.2% of patients who had received 3 years of monthly treatment of ranibizumab, with up to 3.2% of patients requiring panretinal photocoagulation, a potentially visually disabling treatment modality (Brown et al 2013 Ophthalmology 10: 2013-22).

Intravitreal (IVT) deliveries of anti-VEGF therapies such as ranibizumab and aflibercept have demonstrated efficacy and safety for chorioretinal diseases. However, there are many additional factors that contribute to vascular permeability, neovascularization, and other vascular dysfunction. One of the most studied factors that contribute to vascular permeability is angiopoietin-2 (Ang-2). Ang-2 is expressed by vascular endothelial cells during normal vascular development and also in the course of physiological or pathological angiogenesis in the adult (Maisonpierre et al 1997, Science 277: 55-60; Holash et al 1999, Science 284: 1994-98). Binding of Ang-2 to its receptor Tie-2 promotes angiogenesis, both during normal vascular development and in conditions characterized by pathological neovascularization. Genetic deletion of Ang-2 in the mouse markedly inhibits both normal retinal vascular development and pathological neovascularization (Hackett et al 2000, J. Cell Physiol. 184: 275-83; Hackett et al 2002, J. Cell Physiol. 192: 182-7; Gale et al 2002, Dev. Cell 3: 411-423). Targeting angiopoietin-2 (Ang2) will support inhibition of any of these factors, either alone or in combination, and has the potential to improve upon the success of anti-VEGF therapy alone.

BRIEF SUMMARY OF THE INVENTION

According to one aspect of the present invention, methods are provided for treating, preventing or ameliorating at least one symptom or indication of a vascular eye disease or disorder in a subject. The methods according to this aspect of the invention comprise administering a therapeutically effective amount of a pharmaceutical composition comprising an angiopoietin-2 (Ang-2) inhibitor to a subject in need thereof. In certain embodiments, the Ang-2 inhibitor is administered in combination with a vascular endothelial growth factor (VEGF) antagonist.

According to another aspect of the present invention, methods are provided for inhibiting retinal angiogenesis in a subject. The methods comprise administering a therapeutically effective amount of a pharmaceutical composition comprising an Ang-2 inhibitor in combination with a VEGF antagonist to the subject in need thereof. In certain embodiments, combined administration results in reduction of the retinal vascular area by at least 65% as compared to the administration of either Ang-2 inhibitor or the VEGF antagonist alone. In some embodiments, the retinal angiogenesis is associated with a vascular eye disease or disorder.

In another aspect, the present invention provides for methods for inhibiting retinal neovascularization in a subject with an eye disease or disorder associated with angiogenesis, the methods comprising administering a therapeutically effective amount of a pharmaceutical composition comprising an Ang-2 inhibitor in combination with a VEGF antagonist to the subject in need thereof.

According to another aspect of the present invention, methods are provided for inhibiting vascular leak in a subject with an eye disease or disorder. The methods comprise administering a therapeutically effective amount of a pharmaceutical composition comprising an Ang-2 inhibitor in combination with a VEGF antagonist to a subject in need thereof.

In a related aspect, the present invention provides methods for suppressing vascular leak in a subject with an eye disease or disorder associated with angiogenesis, wherein the methods comprise administering a single dose of a VEGF antagonist followed by one or more doses of a pharmaceutical composition comprising an Ang-2 inhibitor to the subject in need thereof.

In several embodiments, the vascular leak is inhibited for at least 3 weeks, more than 3 weeks, more than 4 weeks, more than 8 weeks, or more than 10 weeks as compared to a subject who has been administered the VEGF antagonist alone.

In another aspect, the present invention provides for methods for inhibiting choroidal neovascularization comprising administering a therapeutically effective amount of a pharmaceutical composition comprising an Ang-2 inhibitor to a subject in need thereof.

According to another aspect of the present invention, methods are provided for reducing the dependence and treatment burden of frequent intravitreal injections in a subject with a vascular eye disease or disorder. The methods comprise sequentially administering an initial dose followed by one or more secondary doses of a therapeutically effective amount of a pharmaceutical composition comprising an Ang-2 inhibitor in combination with a VEGF antagonist to the subject in need thereof; wherein the administration of the pharmaceutical composition is reduced to once every 9 weeks as compared to a subject who has been administered the VEGF antagonist alone.

In certain embodiments, the present invention provides method for treating a vascular eye disease, the methods comprising administering one or more doses of a pharmaceutical composition comprising a therapeutically active amount of an anti-Ang-2 inhibitor and a therapeutically active amount of a VEGF antagonist to a subject in need thereof. In certain embodiments, the methods comprise administering an initial dose of the pharmaceutical composition followed by one or more secondary doses. In certain embodiments, each secondary dose is administered 1 to 4 weeks after the immediately preceding dose. In certain embodiments, the methods further comprise administration of one or more tertiary doses to the subject. In certain embodiments, each tertiary dose is administered 5 to 12 weeks after the immediately preceding dose. In one embodiment, each secondary dose is administered 4 weeks after the immediately preceding dose. In certain embodiments, each tertiary dose is administered 8 weeks or 12 weeks after the immediately preceding dose. In certain embodiments, the pharmaceutical composition comprises about 10 mg/mL to about 120 mg/mL of the anti-Ang-2 inhibitor. In certain embodiments, the pharmaceutical composition comprises about 40 mg/mL of the VEGF antagonist. In certain embodiments, the pharmaceutical composition comprises about 10 mg/mL to about 120 mg/mL of the anti-Ang-2 inhibitor and about 40 mg/mL of the VEGF antagonist. In certain embodiments, the pharmaceutical composition is intravitreally administered to the subject. In certain embodiments, each dose of the pharmaceutical composition comprises about 0.5 mg to about 6 mg of the anti-Ang-2 inhibitor and about 2 mg of the VEGF antagonist. In one embodiment, each dose of the pharmaceutical composition comprises about 3 mg of the anti-Ang-2 inhibitor and about 2 mg of the VEGF antagonist. In one embodiment, each dose of the pharmaceutical composition comprises about 6 mg of the anti-Ang-2 inhibitor and about 2 mg of the VEGF antagonist.

In certain embodiments, the eye disease or disorder is selected from the group consisting of diabetic retinopathy, diabetic macular edema, age-related macular degeneration, retinal neovascularization, central retinal vein occlusion, branched retinal vein occlusion, polypoidal choroidal vasculopathy, and choroidal neovascularization.

In certain embodiments, the Ang-2 inhibitor is administered as a co-formulation with a VEGF antagonist. In certain embodiments, the Ang-2 inhibitor alone or in combination with the VEGF antagonist is intravitreally administered to a subject in need thereof. In alternate embodiments, the Ang-2 inhibitor is administered intravenously or subcutaneously. In certain embodiments, the Ang-2 inhibitor is administered intravenously or subcutaneously in combination with the VEGF antagonist, wherein the VEGF antagonist is administered intravitreally. In certain embodiments, an Ang-2 inhibitor and a VEGF antagonist are co-administered topically or intraocularly (e.g., intravitreally).

In certain embodiments, the Ang-2 inhibitor is administered at a dose of from 0.05 mg to 10 mg to a subject in need thereof. In certain embodiments, the VEGF antagonist is administered at a dose of from 0.01 mg to 5 mg to a subject in need thereof. In some embodiments, the Ang-2 inhibitor is administered at a dose of about 1-50 mg/kg of the subject's body weight.

In certain embodiments, one or more secondary doses of the pharmaceutical composition comprising the Ang-2 inhibitor are administered to a subject in need thereof. In some embodiments, the one or more doses comprise at least 2 secondary doses of the pharmaceutical composition. In certain embodiments, each secondary dose is administered 1 to 4 weeks after the immediately preceding dose.

Exemplary Ang-2 inhibitors that can be used in the context of the methods of the present invention include, e.g., small molecule chemical inhibitors of Ang-2, or biological agents that target Ang-2. According to certain embodiments, the Ang-2 inhibitor is an antibody or antigen binding protein that binds the Ang-2 ligand and blocks Tie2 signaling. In certain embodiments, the anti-Ang-2 antibody or antigen-binding protein comprises the heavy chain complementarity determining regions (HCDRs) of a heavy chain variable region (HCVR) comprising the amino acid sequence of SEQ ID NO: 1 and the light chain CDRs of a light chain variable region (LCVR) comprising the amino acid sequence of SEQ ID NO: 2.

VEGF antagonists that may be used in combination with an Ang-2 inhibitor in the compositions and methods of the present invention include anti-VEGF antibodies (e.g., ranibizumab), small molecule VEGF inhibitors (e.g., sunetinib), and VEGF-inhibiting fusion proteins ("VEGF Traps"). An example of a VEGF antagonist that may be used in combination with the anti-Ang-2 antibodies in the methods of treatment of the present invention is aflibercept, a VEGF-inhibiting fusion protein (see U.S. Pat. No. 7,087,411).

In another aspect, the present invention provides a pharmaceutical composition comprising a therapeutically effective amount of an Ang-2 inhibitor and a pharmaceutically acceptable carrier or diluent. In certain embodiments, the pharmaceutical composition further comprises a VEGF antagonist.

In certain embodiments, the present invention provides use of an anti-Ang-2 antibody or antigen-binding fragment thereof of the invention in the manufacture of a medicament to treat or prevent or ameliorate at least a symptom or indication of an eye disease or disorder in a subject, including humans.

In certain embodiments, the present invention provides use of an Ang-2 inhibitor of the invention in conjunction with a VEGF antagonist in the manufacture of a medicament to treat an eye disease or disorder in a subject, including humans.

According to another aspect of the present invention, a stable liquid pharmaceutical formulation is provided, comprising: (i) a VEGF antagonist; (ii) an antibody or antigen-binding fragment thereof that specifically binds to Ang-2; (iii) a buffer; (iv) a non-ionic detergent; (v) a tonicity agent; and (vi) a stabilizer. In one embodiment, a stable ophthalmic formulation is provided, comprising: (i) a VEGF antagonist; (ii) an antibody or antigen-binding fragment thereof that specifically binds to Ang-2; (iii) a buffer; (iv) a non-ionic detergent; (v) a tonicity agent; and (vi) a stabilizer.

In one embodiment, the VEGF antagonist is provided at a concentration of from 5 mg/mL±0.75 mg/mL to about 100 mg/mL±15 mg/mL and the anti-Ang-2 antibody is provided at a concentration of from 10±1.5 mg/mL to 120±18.0 mg/mL. In some embodiments, the VEGF antagonist is provided at a concentration of from 10 mg/mL±1.5 mg/mL to 80 mg/mL±12 mg/mL, or from 20 mg/mL±3.0 mg/mL to 60 mg/mL±9.0 mg/mL. In one embodiment, the VEGF antagonist is provided at a concentration of 40 mg/mL±6.0 mg/mL, or about 40 mg/mL. In one embodiment, the antibody is provided at a concentration of 10 mg/ml±1.5 mg/mL, or about 10 mg/mL. In another embodiment, the antibody is provided at a concentration of 20 mg/mL±3.0 mg/mL, or about 20 mg/mL. In another embodiment, the antibody is provided at a concentration of 60 mg/mL±9.0 mg/mL, or about 60 mg/mL. In another embodiment, the antibody is provided at a concentration of 120 mg/mL±18.0 mg/mL, or about 120 mg/mL.

In certain embodiments, the pH of the liquid formulation is from about pH 5.5 to about pH 6.5. In some embodiments, the pH of the liquid formulation is pH 6.2±0.3, pH 6.2±0.25, pH 6.2±0.2, pH 6.2±0.15, pH 6.2±0.1, pH 6.2±0.05, pH 6.2±0.01, or pH 6.2. In one embodiment, the pH of the liquid formulation is pH 6.2±0.3, or about pH 6.2.

In one embodiment, the buffer is sodium phosphate. In some embodiments, the sodium phosphate is at a concentration of from 5 mM±0.75 mM to 50 mM±7.5 mM, 5 mM±0.75 mM to 40 mM±6.0 mM, or 5 mM±0.75 mM to 25 mM±3.75 mM. In one embodiment, the sodium phosphate is at a concentration of 10 mM±1.5 mM or about 10 mM.

In some embodiments, the non-ionic detergent is a non-ionic polymer containing a polyoxyethylene moiety. In some embodiments, the non-ionic detergent is any one or more of polysorbate 20, poloxamer 188 and polyethylene glycol 3350. In one embodiment, the detergent is polysorbate 20. In one embodiment, the detergent is polysorbate 80.

In certain embodiments, the non-ionic detergent is at a concentration of from 0.005%±0.00075% to 1%±0.15% "weight to volume" or "w/v", wherein, e.g., 0.1 g/ml=10% and 0.01 g/ml=1%. In one embodiment, the non-ionic detergent is polysorbate 20, which is at a concentration of from about 0.01%±0.0045% to about 0.05%±0.0045% w/v. In one embodiment, the non-ionic detergent is polysorbate 20, which is at a concentration of 0.03%±0.0045% w/v or about 0.03% w/v.

In some embodiments, the tonicity agent is sodium chloride or potassium chloride. In one embodiment, the tonicity agent is sodium chloride. In some embodiments, the tonicity agent is sodium chloride at a concentration of from 10 mM±1.5 mM to 75 mM±11.25 mM, 20 mM±3.0 mM to 60 mM±9.0 mM, or 30 mM±4.5 mM to 50 mM±7.5 mM. In one embodiment, the sodium chloride is at a concentration of 40 mM±6.0 mM, or about 40 mM.

In one embodiment, the stabilizer is a sugar. In one embodiment, the sugar is selected from the group consisting of sucrose, mannitol and trehalose. In one embodiment, the stabilizer is sucrose.

In some embodiments, the stabilizer is at a concentration of from 1%±0.15% w/v to 20%±3% w/v. In some embodiments, the stabilizer is sucrose at a concentration of from 1%±0.15% w/v to 15%±2.25% w/v, or from 1%±0.15% w/v to 10%±1.5% w/v. In one embodiment, the stabilizer is sucrose at a concentration of 5%±0.15% w/v or about 5% w/v. In another embodiment, the stabilizer is sucrose at a concentration of 7.5%±1.125% w/v or about 7.5% w/v. In another embodiment, the stabilizer is sucrose at a concentration of 10%±1.5% w/v or about 10% w/v. In another embodiment, the stabilizer is sucrose at a concentration of 12.5%±1.875% w/v or about 12.5% w/v. In another embodiment, the stabilizer is sucrose at a concentration of 15%±2.25% w/v or about 15% w/v. In another embodiment, the stabilizer is sucrose at a concentration of 20%±3% w/v or about 20% w/v.

In one aspect, a stable liquid pharmaceutical formulation is provided, comprising: (i) from 5±0.75 mg/mL to 100±15.0 mg/mL of a VEGF antagonist; (ii) from 5±0.75 mg/ml to 150±22.5 mg/ml of a human antibody that specifically binds to human Ang-2; (iii) from 5 mM±0.75 mM to 50 mM±7.5 mM sodium phosphate; (iv) from 0.01%±0.0015% to 0.1%±0.015% (w/v) polysorbate 20; (v) from 10 mM±1.5 mM to 100 mM±15 mM sodium chloride; and (vi) from 1%±0.15% to 20%±3% (w/v) sucrose, at a pH of from about 5.5 to about 6.5.

In one embodiment, the pharmaceutical formulation comprises (i) 40 mg/mL±6.0 mg/mL of aflibercept; (ii) 10±1.5 mg/mL of anti-Ang-2 antibody; (iii) 10±1.5 mM sodium phosphate; (iv) 0.03%±0.0045% (w/v) polysorbate 20; (v) 40 mM±6.0 mM sodium chloride; and (vi) 5%±0.75% (w/v) sucrose, at a pH of 6.2±0.3.

In one embodiment, the pharmaceutical formulation comprises (i) 40 mg/mL±6.0 mg/mL of aflibercept; (ii) 20±3.0 mg/mL of anti-Ang-2 antibody; (iii) 10±1.5 mM sodium phosphate; (iv) 0.03%±0.0045% (w/v) polysorbate 20; (v) 40 mM±6.0 mM sodium chloride; and (vi) 5%±0.75% (w/v) sucrose, at a pH of 6.2±0.3.

In one embodiment, the pharmaceutical formulation comprises (i) 40 mg/mL±6.0 mg/mL of aflibercept; (ii) 60±9.0 mg/mL of anti-Ang-2 antibody; (iii) 10±1.5 mM sodium phosphate; (iv) 0.03%±0.0045% (w/v) polysorbate 20; (v) 40 mM±6.0 mM sodium chloride; and (vi) 5%±0.75% (w/v) sucrose, at a pH of 6.2±0.3.

In one embodiment, the pharmaceutical formulation comprises (i) 40 mg/mL±6.0 mg/mL of aflibercept; (ii) 120±18.0 mg/mL of anti-Ang-2 antibody; (iii) 10±1.5 mM sodium phosphate; (iv) 0.03%±0.0045% (w/v) polysorbate 20; (v) 40 mM±6.0 mM sodium chloride; and (vi) 5%±0.75% (w/v) sucrose, at a pH of 6.2±0.3.

In one aspect, a liquid pharmaceutical formulation of the present invention is provided in a container. In one embodiment, the container is a polycarbonate vial. In another embodiment, the container is a glass vial. In one embodiment, the glass vial is a type 1 borosilicate glass vial with a fluorocarbon-coated butyl rubber stopper. In another embodiment, the container is a microinf user. In another embodiment, the container is a syringe. In a specific embodiment, the syringe comprises a fluorocarbon-coated plunger. In one embodiment, the syringe is a 2 mL long glass syringe containing less than about 500 parts per billion of tungsten equipped with a 30-G needle, a fluorocarbon-coated butyl rubber stopper, and a latex-free, non-cytotoxic rubber tip cap. In one embodiment, the syringe is a NUOVA OMPI 2 mL long glass syringe equipped with a 30-G thin wall needle, a FLUROTEC-coated 4432/50 GRY B2-40 stopper, and a FM 27 rubber tip cap. In certain embodiments, the syringe is 1 mL, 2 mL or 3 mL plastic syringe fitted with a 27-G needle. In one embodiment, the container is a polyvinyl chloride IV bag. In another embodiment, the container is a polyolefin IV bag.

In one aspect, the present invention comprises a pre-filled syringe comprising a pharmaceutical formulation of any of the preceding aspects.

In one aspect, a kit comprising a pharmaceutical composition of any one of the preceding aspects, a container, and instructions is provided. In one embodiment, the container is a prefilled syringe. In one embodiment, the container is a borosilicate vial fitted with a FLUROTEC-coated 4432/50 rubber stopper.

Other embodiments of the present invention will become apparent from a review of the ensuing detailed description.

DETAILED DESCRIPTION

Figure 1:
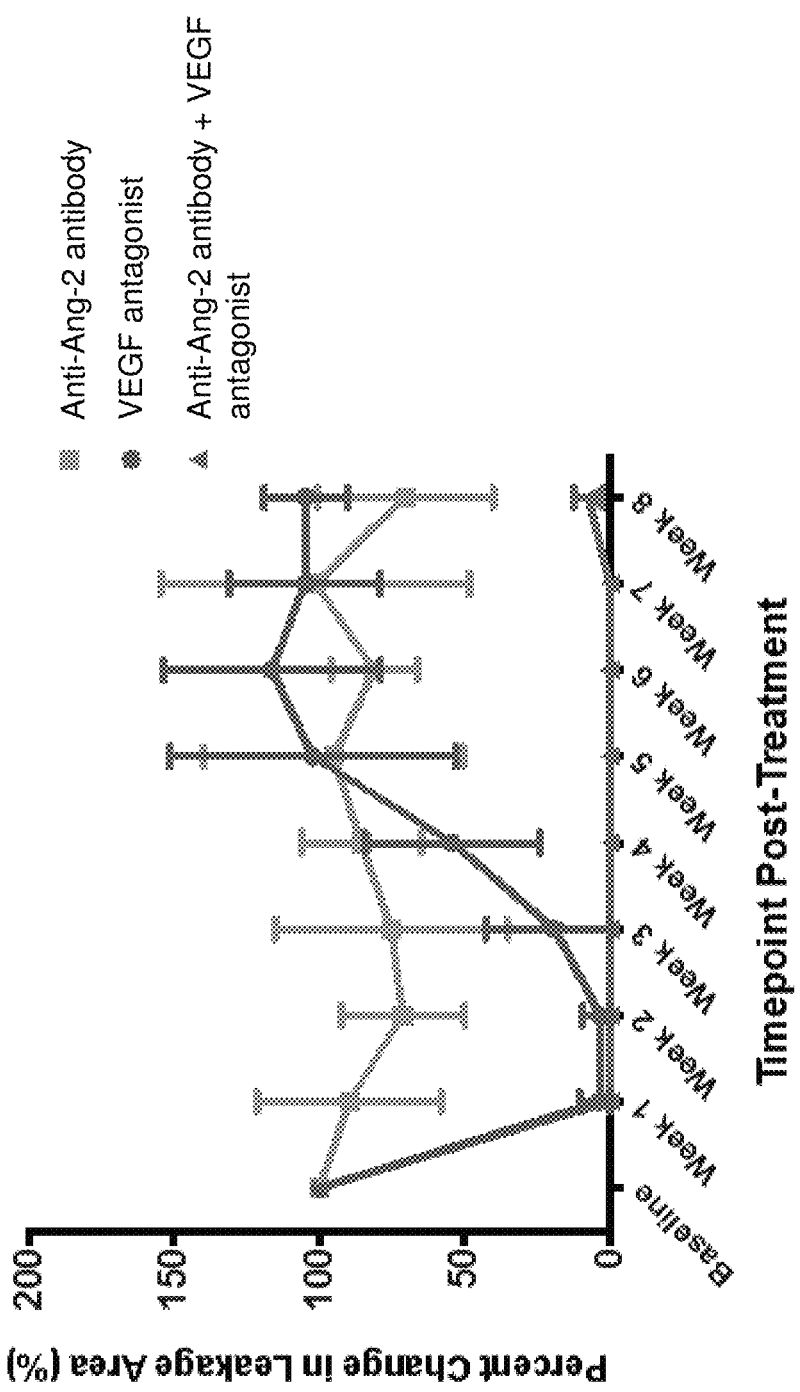
FIG. 1 shows the percent change in leakage area in rabbits with DL-alpha-aminoadipic acid (DL-alpha-AAA)—induced retinal neovascularization which have been treated with anti-Ang-2 antibody, VEGF antagonist, or a combination of anti-Ang-2 antibody and VEGF antagonist, as described in Example 2 herein.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All publications mentioned herein are incorporated herein by reference to describe in their entirety.

Methods for Treating or Ameliorating Vascular Eye Diseases or Disorders

The present invention includes methods for treating, preventing, or ameliorating at least one symptom or indication of a vascular eye disease or disorder in a subject. The methods according to this aspect of the invention comprise administering a therapeutically effective amount of a pharmaceutical composition comprising an Ang-2 inhibitor to the subject in need thereof. In some embodiments, the Ang-2 inhibitor is administered subcutaneously or intravenously. In some embodiments, the Ang-2 inhibitor is administered in combination with a VEGF antagonist. In some embodiments, the Ang-2 inhibitor is intravitreally administered in combination with the VEGF antagonist. In some embodiments, the Ang-2 inhibitor is administered as a single combined dosage formulation with the VEGF antagonist. In some embodiments, the Ang-2 inhibitor is administered in combination with the VEGF antagonist, wherein the Ang-2 inhibitor is administered intravenously and the VEGF antagonist is administered intravitreally. The VEGF antagonist may be administered before, after or concurrently with the Ang-2 inhibitor.

As used herein, the terms "treat", "treating", or the like, mean to alleviate symptoms, eliminate the causation of symptoms either on a temporary or permanent basis, or to prevent or slow the appearance of symptoms of a neovascular eye disease. In certain embodiments, the present methods are useful for treating or ameliorating at least one symptom or indication including, but not limited to, retinal angiogenesis, neovascularization, vascular leak, retinal thickening within 500 μm of the center of the fovea, hard, yellow exudates within 500 μm of the center of the fovea with adjacent retinal thickening, and at least 1 disc area of retinal thickening, any part of which is within 1 disc diameter of the center of the fovea, blurry vision, floaters, loss of contrast, double vision, and eventual loss of vision. In the context of methods for treating a vascular eye disease such as AMD or DME, the term means that, from the initiation of treatment, the patient exhibits gain of one or more (e.g., 1, 2, 3, 4, 5, 6, 7, 8, 9, 10 or more) letters on the Early Treatment Diabetic Retinopathy Study (EDTRS) visual acuity chart. In certain embodiments, the term means that, from initiation of treatment, vision loss of greater than or equal to 15 letters is prevented in the patient.

As used herein, the terms "prevent", "preventing", or the like, mean to prevent development of a symptom, indication or a complication of a vascular eye disease. In the context of methods for treating a vascular eye disease such as AMD or DME, the term means, from initiation of treatment, moderate or severe vision loss is prevented in a patient.

As used herein, a "vascular eye disease or disorder" refers to eye disease or disorders that affect blood vessels in the eye. The diseases may be caused due to abnormal angiogenesis (formation of new blood vessels) or occlusion or blockage of blood vessels. The term, as used herein, includes eye diseases or disorders associated with angiogenesis. The term includes, but is not limited to eye disease or disorder selected from the group consisting of diabetic retinopathy, diabetic macular edema, age-related macular degeneration, retinal neovascularization, central retinal vein occlusion, branched retinal vein occlusion, polypoidal choroidal vasculopathy, and choroidal neovascularization. In certain embodiments, the term "neovascular eye disease or disorder" may be used interchangeably with the term "eye disease or disorder associated with angiogenesis."

In certain embodiments, the present invention includes methods for treating, preventing, or ameliorating at least one symptom or indication of an eye disease or disorder associated with angiogenesis in a subject, wherein the disease or disorder is selected from the group consisting of diabetic retinopathy, diabetic macular edema, age-related macular degeneration, retinal neovascularization, polypoidal choroidal vasculopathy, and choroidal neovascularization.

"Diabetic Macular Edema" (DME), as used herein, refers to a serious eye condition that affects people with diabetes (type 1 or 2). Macular edema occurs when blood vessels in the retina leak into the macula and fluid and protein deposits collect on or under the macula of the eye (a yellow central area of the retina) and causes it to thicken and swell (edema). The swelling may distort a person's central vision, as the macula is near the center of the retina at the back of the eyeball. The primary symptoms of DME include, but are not limited to, blurry vision, floaters, loss of contrast, double vision, and eventual loss of vision. The pathology of DME is characterized by breakdown of the blood-retinal barrier, normally preventing water movement in the retina, thus allowing fluid to accumulate in the retinal tissue, and presence of retinal thickening. DME is presently diagnosed during an eye examination consisting of a visual acuity test, which determines the smallest letters a person can read on a standardized chart, a dilated eye exam to check for signs of the disease, imaging tests such as optical coherence tomography (OCT) or fluorescein angiography (FA) and tonometry, an instrument that measures pressure inside the eye. The following studies are also performed to determine treatment: optical coherence tomography (OCT), fluorescein angiography, and color stereo fundus photography. DME can be broadly characterized into two main categories— Focal and Diffuse. Focal DME is characterized by specific areas of separate and distinct leakage in the macula with sufficient macular blood flow. Diffuse DME results from leakage of the entire capillary bed surrounding the macula, resulting from a breakdown of the inner blood-retina barrier of the eye. In addition to Focal and Diffuse, DME is also categorized based on clinical exam findings into clinically significant macular edema (CSME), non-CSME and CSME with central involvement (CSME-CI), which involves the fovea. The present invention includes methods to treat the above-mentioned categories of DME.

Age-related macular degeneration (AMD), as used herein, refers to a serious eye condition when the small central portion of the retina, known as the macula, deteriorates. The wet form of AMD is characterized by the growth of abnormal blood vessels from the choroid underneath the macula. This is called choroidal neovascularization. These blood vessels leak blood and fluid into the retina, causing distortion of vision that makes straight lines look wavy, as well as blind spots and loss of central vision. These abnormal blood vessels eventually scar, leading to permanent loss of central vision. The symptoms of AMD include dark, blurry areas in the center of vision; and diminished or changed color perception. AMD can be detected in a routine eye exam. One of the most common early signs of macular degeneration is the presence of drusen—tiny yellow deposits under the retina—or pigment clumping.

As used herein, the expression "a subject in need thereof" means a human or non-human mammal that exhibits one or more symptoms or indications of, and/or who has been diagnosed with an eye disease or disorder associated angiogenesis. The term "a subject in need thereof" may also include, e.g., subjects who, prior to treatment, exhibit (or have exhibited) one or more indications of a neovascular eye disease such as, e.g., retinal angiogenesis, neovascularization, vascular leak, retinal thickening within 500 µm of the center of the fovea, hard, yellow exudates within 500 µm of the center of the fovea with adjacent retinal thickening, and at least 1 disc area of retinal thickening, any part of which is within 1 disc diameter of the center of the fovea, blurry vision, floaters, loss of contrast, double vision, and eventual loss of vision.

In the context of the invention, a "subject in need thereof" also includes human or non-human mammal who has a vascular eye disease or disorder selected from the group consisting of diabetic retinopathy, diabetic macular edema, age-related macular degeneration, retinal neovascularization, central retinal vein occlusion, branched retinal vein occlusion, polypoidal choroidal vasculopathy, and choroidal neovascularization.

In the context of the present invention, "a subject in need thereof" may include a subset of population which is more susceptible to DME or AMD or may show an elevated level of a DME-associated or an AMD-associated biomarker. For example, "a subject in need thereof" may include a subject suffering from diabetes for more than 10 years, have frequent high blood sugar levels or high fasting blood glucose levels. In certain embodiments, the term "a subject in need thereof" includes a subject who, prior to or at the time of administration of the Ang-2 inhibitor and/or VEGF antagonist, has or is diagnosed with diabetes. In certain embodiments, the term "a subject in need thereof" includes a subject who, prior to or at the time of administration of the Ang-2 inhibitor and/or VEGF antagonist, is more than 50 years old. In some embodiments, the term "a subject in need thereof" includes subjects who are smokers, or subjects with high blood pressure or high cholesterol.

The present invention includes methods for treating, preventing or reducing the severity of a vascular eye disease comprising administering a therapeutically effective amount of a pharmaceutical composition comprising an Ang-2 inhibitor in combination with a VEGF antagonist to a subject in need thereof, wherein the pharmaceutical composition is administered to the subject in multiple doses, e.g., as part of a specific therapeutic dosing regimen. For example, the therapeutic dosing regimen may comprise administering multiple doses of the pharmaceutical composition to the subject at a frequency of about once a day, once every two days, once every three days, once every four days, once every five days, once every six days, once a week, once every two weeks, once every three weeks, once every four weeks, once a month, once every two months, once every three months, once every four months, or less frequently. In certain embodiments, the therapeutic dosing regimen may comprise administering multiple doses of the pharmaceutical composition to the subject at a frequency of once a day or 2 times a day or more.

The methods of the present invention, according to certain embodiments, comprise administering to a subject a therapeutically effective amount of a pharmaceutical composition comprising an Ang-2 inhibitor in combination with a VEGF antagonist. In certain embodiments, the Ang-2 inhibitor of the invention may be administered in combination with therapy including laser treatment to stop leakage into the macula. As used herein, the phrase 'in combination with" means that the pharmaceutical composition comprising an Ang-2 inhibitor is administered to the subject at the same time as, just before, or just after administration of the VEGF antagonist.

The present invention also includes methods for inhibiting or reducing or suppressing vascular leak in a subject. In certain embodiments, the methods according to this aspect of the invention comprise administering to the subject one or more doses of a pharmaceutical composition comprising an Ang-2 inhibitor to reduce or inhibit vascular leak in the eye of a subject. In certain other embodiments, the methods comprise administering to the subject one or more doses of a pharmaceutical composition comprising an Ang-2 inhibitor in combination with a VEGF antagonist to reduce or inhibit vascular leak in the eye of a subject. In certain embodiments, the vascular leak is inhibited for more than 3 weeks, more than 4 weeks, more than 8 weeks, or more than 10 weeks than in a subject who has been administered the VEGF antagonist alone.

The methods of the present invention, according to certain embodiments, comprise administering to a subject a therapeutically effective amount of a pharmaceutical composition comprising an Ang-2 inhibitor in combination with a VEGF antagonist. As used herein, the phrase 'in combination with" means that the pharmaceutical composition comprising an Ang-2 inhibitor is administered to the subject at the same time as, just before, or just after administration of the VEGF antagonist. In certain embodiments, the VEGF antagonist is administered as a co-formulation with the Ang-2 inhibitor. In a related embodiment, the present invention includes methods comprising administering a therapeutically effective amount of a pharmaceutical composition comprising an Ang-2 inhibitor to a subject to provide a greater therapeutic effect or synergistic effect as compared to administration of the VEGF antagonist alone. The subject may be on a therapeutic regimen of intravitreally administered VEGF antagonist. In some embodiments, the Ang-2 inhibitor is added to this therapeutic regimen, wherein one or more intravitreal injections of the VEGF antagonist may be reduced or the duration between successive intravitreal injections may be increased.

In certain embodiments, the present invention provides methods to treat a vascular eye disease, the methods comprising administering one or more doses of a pharmaceutical composition comprising therapeutically effective amount of an anti-Ang-2 inhibitor and therapeutically effective amount of a VEGF antagonist to a subject in need thereof. In certain embodiments, the pharmaceutical composition is intravitreally administered to the subject. In certain embodiments, the pharmaceutical composition comprises about 10 mg/mL to about 120 mg/mL of the anti-Ang-2 inhibitor and about 40 mg/mL of the VEGF antagonist. In certain embodiments, the methods comprise administering an initial dose of the pharmaceutical composition, followed by one or more secondary doses, wherein each secondary dose is administered 1 to 4 weeks after the immediately preceding dose. In certain embodiments, one or more tertiary doses of the pharmaceutical composition are administered, wherein each tertiary dose is administered 5 to 12 weeks after the immediately preceding dose. In certain embodiments, each dose of the pharmaceutical composition comprises about 0.5 to about 6 mg of the anti-Ang-2 inhibitor and about 2 mg of the VEGF antagonist.

In certain embodiments, the present invention provides methods to reduce the number of intravitreal injections in a subject with a vascular eye disease, the methods comprising administering a pharmaceutical composition comprising an anti-Ang-2 inhibitor and a VEGF antagonist, wherein the intravitreal administration is reduced to once in 8 weeks as compared to a subject administered with the anti-Ang-2 inhibitor or the VEGF antagonist alone.

The methods of the present invention are useful for treating or preventing vascular eye disorders in patients that have been diagnosed with or are at risk of being afflicted with a vascular eye disorder. Generally, the methods of the present invention demonstrate efficacy within 36 weeks of the initiation of the treatment regimen (with the initial dose administered at "week 0"), e.g., by the end of week 6, by the end of week 12, by the end of week 18, by the end of week 24, etc. In the context of methods for treating angiogenic eye disorders such as AMD, and DME, "efficacy" means that, from the initiation of treatment, the patient exhibits a loss of 10 or fewer letters on the Early Treatment Diabetic Retinopathy Study (ETDRS) visual acuity chart. In certain embodiments, "efficacy" means a gain of one or more (e.g., 1, 2, 3, 4, 5, 6, 7, 8, 9, 10, 11 or more) letters on the ETDRS chart from the time of initiation of treatment.

Angiopoietin-2 (Ang-2) Inhibitors

As used herein, the term "Ang-2" or "ANG2" means a human angiopoietin-2, which is generally known as an autocrine antagonist of Tie2 activation. Ang-2 is generally known in the art to "prime" the vascular endothelium to receive the effects of cytokines. Ang-2 is strongly expressed in tumor vasculature, and is generally thought to act synergistically with other cytokines (i.e., vascular endothelial growth factor) to promote angiogenesis and tumor progression.

As used herein, an "Ang-2 inhibitor" (also referred to herein as an "Ang-2 antagonist," an "Ang-2 blocker," etc.) is any agent which binds to or interacts with Ang-2, and inhibits or attenuates the normal biological signaling function/activity of Ang-2.

Non-limiting examples of categories of Ang-2 inhibitors include small molecule Ang-2 inhibitors, anti-Ang-2 aptamers, peptide-based Ang-2 inhibitors (e.g., "peptibody" molecules), "receptor-bodies" (e.g., engineered molecules comprising the receptor-binding domain of an Ang-2 component), and antibodies or antigen-binding fragments of antibodies that specifically bind human Ang-2. In certain embodiments, the Ang-2 inhibitor is an antibody or antigen binding fragment thereof as disclosed in e.g., US Patent Application Publication No. US20110027286. In certain embodiments, the anti-Ang-2 antibody or antigen binding fragment thereof comprises a heavy chain variable region (HCVR) having an amino acid sequence of SEQ ID NO: 1 and a light chain variable region (LCVR) having an amino acid sequence of SEQ ID NO: 2.

The methods of the present invention comprise administering to a subject in need thereof a therapeutic composition comprising an Ang-2 inhibitor.

Anti-Ang-2 Antibodies and Antigen-Binding Fragments Thereof

According to certain exemplary embodiments of the present invention, the Ang-2 inhibitor is an anti-Ang-2 antibody or antigen-binding fragment thereof. The term "antibody," as used herein, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-Ang-2 antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or heterodimer (or other multimer) of any of the variable and constant domain configurations listed above in non-covalent association with one another and/or with one or more monomeric $V_H$ or $V_L$ domain (e.g., by disulfide bond(s)).

The term "antibody," as used herein, also includes multispecific (e.g., bispecific) antibodies. A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen-binding fragment of an antibody of the present invention using routine techniques available in the art. For example, the present invention includes methods comprising the use of bispecific antibodies wherein one arm of an immunoglobulin is specific for IL-4Rα or a fragment thereof, and the other arm of the immunoglobulin is specific for a second therapeutic target or is conjugated to a therapeutic moiety. Exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [*Epub: Dec.* 4, 2012]).

The antibodies used in the methods of the present invention may be human antibodies. The term "human antibody," as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies used in the methods of the present invention may be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

According to certain embodiments, the antibodies used in the pharmaceutical formulations and methods of the present invention specifically bind Ang-2. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" Ang-2, as used in the context of the present invention, includes antibodies that bind Ang-2 or portion thereof with a $K_D$ of less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human Ang-2 may, however, have cross-reactivity to other antigens, such as Ang-2 molecules from other (non-human) species.

According to certain exemplary embodiments of the present invention, the Ang-2 inhibitor is an anti-Ang-2 antibody, or antigen-binding fragment thereof comprising a heavy chain variable region (HCVR), light chain variable region (LCVR), and/or complementarity determining regions (CDRs) comprising any of the amino acid sequences of the anti-Ang-2 antibodies as set forth in US Patent Application Publication No. US20110027286.

In certain exemplary embodiments, the anti-Ang-2 antibody or antigen-binding fragment thereof that can be used in the context of the methods of the present invention comprises the heavy chain complementarity determining regions (HCDRs) of a heavy chain variable region (HCVR) comprising the amino acid sequence of SEQ ID NO: 1 and the light chain complementarity determining regions (LCDRs) of a light chain variable region (LCVR) comprising the amino acid sequence of SEQ ID NO: 2. According to certain embodiments, the anti-Ang-2 antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 3; the HCDR2 comprises the amino acid sequence of SEQ ID NO: 4; the HCDR3 comprises the amino acid sequence of SEQ ID NO: 5; the LCDR1 comprises the amino acid sequence of SEQ ID NO: 6; the LCDR2 comprises the amino acid sequence of SEQ ID NO: 7; and the LCDR3 comprises the amino acid sequence of SEQ ID NO: 8. In yet other embodiments, the anti-Ang-2 antibody or antigen-binding fragment thereof comprises an HCVR comprising SEQ ID NO: 1 and an LCVR comprising SEQ ID NO: 2. In certain embodiments, the methods of the present invention comprise the use of an anti-Ang-2 antibody, wherein the antibody comprises a heavy chain comprising the amino acid sequence of SEQ ID NO: 9. In some embodiments, the anti-Ang-2 antibody comprises a light chain comprising the amino acid sequence of SEQ ID NO: 10. An exemplary antibody comprising a heavy chain comprising the amino acid sequence of SEQ ID NO: 9 and a light chain comprising the amino acid sequence of SEQ ID NO: 10 is the fully human anti-Ang-2 antibody known as nesvacumab. According to certain exemplary embodiments, the methods of the present invention comprise the use of nesvacumab, or a bioequivalent thereof. The term "bioequivalent", as used herein, refers to anti-Ang-2 antibodies or Ang-2-binding proteins or fragments thereof that are pharmaceutical equivalents or pharmaceutical alternatives whose rate and/or extent of absorption do not show a significant difference with that of nesvacumab when administered at the same molar dose under similar experimental conditions, either single dose or multiple dose. In the context of the invention, the term refers to antigen-binding proteins that bind to Ang-2 which do not have clinically meaningful differences with nesvacumab in their safety, purity and/or potency.

The non-limiting, exemplary antibody used in the Examples herein is referred to as "H1H685P", as in US 2011/0027286. This antibody comprises an HCVR/LCVR amino acid sequence pair having SEQ ID NOs: 1/2, and HCDR1-HCDR2-HCDR3/LCDR1-LCDR2-LCDR3 domains represented by SEQ ID NOs: 3-4-5/SEQ ID NOs: 6-7-8.

Other antibodies to human Ang-2 are described in patent application publications US 2010/0166768, US 2011/0065902, and WO 2010/077854, which are herein incorporated by reference.

The amount of antibody, or antigen-binding fragment thereof, contained within the pharmaceutical formulations of the present invention may vary depending on the specific properties desired of the formulations, as well as the particular circumstances and purposes for which the formulations are intended to be used. In certain embodiments, the pharmaceutical formulations are liquid formulations that may contain 5±0.75 mg/mL to 150±22.5 mg/mL of antibody; 7.5±1.125 mg/mL to 140±21 mg/mL of antibody. For example, the formulations of the present invention may comprise about 10 mg/mL; about 20 mg/mL; about 30 mg/mL; about 50 mg/mL; about 60 mg/mL; about 80 mg/mL; about 100 mg/mL; about 120 mg/mL; or about 150 mg/mL of an antibody or an antigen-binding fragment thereof, that binds specifically to human Ang-2.

VEGF Antagonists

As used herein, a "VEGF antagonist" is any agent that binds to or interacts with VEGF, inhibits the binding of VEGF to its receptors (VEGFR1 and VEGFR2), and/or inhibits the biological signaling and activity of VEGF. VEGF antagonists include molecules which interfere with the interaction between VEGF and a natural VEGF receptor, e.g., molecules which bind to VEGF or a VEGF receptor and prevent or otherwise hinder the interaction between VEGF and a VEGF receptor. Specific exemplary VEGF antagonists include anti-VEGF antibodies (e.g., ranibizumab [LUCENTIS®]), anti-VEGF receptor antibodies (e.g., anti-VEGFR1 antibodies, anti-VEGFR2 antibodies, etc.), small molecule inhibitors of VEGF (e.g., sunitinib), and VEGF receptor-based chimeric molecules or VEGF-inhibiting fusion proteins (also referred to herein as "VEGF-Traps").

VEGF receptor-based chimeric molecules include chimeric polypeptides which comprise two or more immunoglobulin (Ig)-like domains of a VEGF receptor such as VEGFR1 (also referred to as Flt1) and/or VEGFR2 (also referred to as Flk1 or KDR), and may also contain a multimerizing domain (e.g., an Fc domain which facilitates the multimerization [e.g., dimerization] of two or more chimeric polypeptides). An exemplary VEGF receptor-based chimeric molecule is a molecule referred to as VEGFR1R2-FcΔC1(a) (also known as aflibercept; marketed under the product name EYLEA®). In certain embodiments, aflibercept is encoded by the amino acid sequence of SEQ ID NO: 11.

The amount of the VEGF antagonist contained within the pharmaceutical formulations of the present invention may vary depending on the specific properties desired of the formulations, as well as the particular circumstances and purposes for which the formulations are intended to be used. In certain embodiments, the pharmaceutical formulations are liquid formulations that may contain 5±0.75 mg/mL to 150±22.5 mg/mL of VEGF antagonist; 10±1.5 mg/mL to 100±15.0 mg/mL of VEGF antagonist; 20±3 mg/mL to 80±12 mg/mL of VEGF antagonist; 30±4.5 mg/mL to 70±10.5 mg/mL of VEGF antagonist or 40±6.0 mg/mL of the VEGF antagonist. For example, the formulations of the present invention may comprise about 20 mg/mL; about 30 mg/mL; about 40 mg/mL; about 50 mg/mL; or about 60 mg/mL of a VEGF antagonist.

Combination Therapies

The methods of the present invention, according to certain embodiments, comprise administering to the subject a VEGF antagonist in combination with an anti-Ang-2 antibody. As used herein, the expression "in combination with" means that the VEGF antagonist is administered before, after, or concurrent with the pharmaceutical composition comprising the anti-Ang-2 antibody. The term "in combination with" also includes sequential or concomitant administration of anti-Ang-2 antibody and a VEGF antagonist. For example, when administered "before" the pharmaceutical composition comprising the anti-Ang-2 antibody, the VEGF antagonist may be administered more than 72 hours, about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the anti-Ang-2 antibody. When administered "after" the pharmaceutical composition comprising the anti-Ang-2 antibody, the VEGF antagonist may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours, about 72 hours, or more than 72 hours after the administration of the pharmaceutical composition comprising the anti-Ang-2 antibody. Administration "concurrent" with the pharmaceutical composition comprising the anti-Ang-2 antibody means that the VEGF antagonist is administered to the subject in a separate dosage form within less than 5 minutes (before, after, or at the same time) of administration of the pharmaceutical composition comprising the anti-Ang-2 antibody, or administered to the subject as a single combined dosage formulation comprising both the VEGF antagonist and the anti-Ang-2 antibody.

Combination therapies may include an anti-Ang-2 antibody of the invention and a VEGF antagonist (e.g., aflibercept, a VEGF-Trap, see, e.g., U.S. Pat. No. 7,087,411 (also referred to herein as a "VEGF-inhibiting fusion protein"), anti-VEGF antibody (e.g., ranibizumab), a small molecule kinase inhibitor of VEGF receptor (e.g., sunitinib, sorafenib or pazopanib), etc.

The methods of the invention comprise administering an anti-Ang-2 antibody in combination with a VEGF antagonist for additive or synergistic activity to treat or ameliorate at least one symptom or indication of an eye disease or disorder selected from the group consisting of diabetic retinopathy, diabetic macular edema, age-related macular degeneration, retinal neovascularization, central retinal vein occlusion, branched retinal vein occlusion, polypoidal choroidal vasculopathy, and choroidal neovascularization.

Pharmaceutical Compositions and Formulations

The present invention includes methods which comprise administering an Ang-2 inhibitor to a subject wherein the Ang-2 inhibitor is contained within a pharmaceutical composition. In certain embodiments, the pharmaceutical composition further comprises a VEGF antagonist. In alternate embodiments, the Ang-2 inhibitor and the VEGF antagonist may be in own separate pharmaceutical dosage formulation. The pharmaceutical compositions of the invention may be formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

As used herein, the expression "pharmaceutical formulation" means a combination of at least one active ingredient (e.g., a small molecule, macromolecule, compound, etc. which is capable of exerting a biological effect in a human or non-human animal), and at least one inactive ingredient which, when combined with the active ingredient or one or more additional inactive ingredients, is suitable for therapeutic administration to a human or non-human animal. The term "formulation", as used herein, means "pharmaceutical formulation" unless specifically indicated otherwise. The present invention provides pharmaceutical formulations comprising at least one therapeutic polypeptide. According to certain embodiments of the present invention, the therapeutic polypeptide is an antibody, or an antigen-binding fragment thereof, which binds specifically to human angiopoietin-2 (Ang-2) protein. According to certain other embodiments, the present invention provides pharmaceutical formulations comprising more than one therapeutic polypeptide. More specifically, the present invention includes pharmaceutical formulations that comprise: (i) a human antibody that specifically binds to human Ang-2; (ii) a VEGF antagonist; (iii) a sodium phosphate buffer; (iv) an organic co-solvent that is a non-ionic surfactant; (v) a tonicity agent such as sodium chloride; and (vi) a thermal stabilizer that is a carbohydrate. Specific exemplary components and formulations included within the present invention are described in detail below.

The amount of antibody, or antigen-binding fragment thereof, contained within the pharmaceutical formulations of the present invention may vary depending on the specific properties desired of the formulations, as well as the particular circumstances and purposes for which the formulations are intended to be used. In certain embodiments, the pharmaceutical formulations are liquid formulations that may contain 5±0.75 mg/mL to 150±22.5 mg/mL of antibody; 7.5±1.125 mg/mL to 140±21 mg/mL of antibody; 10±1.5 mg/mL to 130±19.5 mg/mL of antibody; 10±1.5 mg/mL of antibody; 20±3 mg/mL of antibody; 60±9 mg/mL of antibody; or 120±18 mg/mL of antibody. For example, the formulations of the present invention may comprise about 10 mg/mL; about 20 mg/mL; about 40 mg/mL; about 60 mg/mL; about 80 mg/mL; about 100 mg/mL; about 120 mg/mL; or about 140 mg/mL of an antibody or an antigen-binding fragment thereof that binds specifically to human Ang-2.

In certain embodiments, the pharmaceutical formulations are liquid formulations that may contain 5±0.75 mg/mL to 100±15 mg/mL of a VEGF antagonist. For example, the formulations of the present invention may comprise about 5 mg/mL; about 10 mg/mL; about 15 mg/mL; about 20 mg/mL; about 25 mg/mL; about 30 mg/mL; about 35 mg/mL; about 40 mg/mL; about 50 mg/mL; about 60 mg/mL; about 70 mg/mL; about 80 mg/mL; about 90 mg/mL; or about 100 mg/mL of a VEGF antagonist such as aflibercept.

In certain embodiments, the pharmaceutical formulations are stable liquid co-formulations comprising about 5 mg/mL to about 150 mg/mL of the anti-Ang-2 antibody and about 5 to 100 mg/mL of the VEGF antagonist.

The pharmaceutical formulations of the present invention comprise one or more excipients. The term "excipient", as used herein, means any non-therapeutic agent added to the formulation to provide a desired consistency, viscosity or stabilizing effect.

In certain embodiments, the pharmaceutical formulation of the invention comprises at least one organic cosolvent in a type and in an amount that stabilizes the human Ang-2 antibody under conditions of rough handling or agitation, such as, e.g., vortexing. In some embodiments, what is meant by "stabilizes" is the prevention of the formation of more than 4% aggregated antibody of the total amount of antibody (on a molar basis) over the course of rough handling. In some embodiments, rough handling is vortexing a solution containing the antibody and the organic cosolvent for about 60 minutes or about 120 minutes.

In certain embodiments, the organic cosolvent is a non-ionic surfactant, such as an alkyl poly(ethylene oxide). Specific non-ionic surfactants that can be included in the formulations of the present invention include, e.g., polysorbates such as polysorbate 20, polysorbate 28, polysorbate 40, polysorbate 60, polysorbate 65, polysorbate 80, polysorbate 81, and polysorbate 85; poloxamers such as poloxamer 181, poloxamer 188, poloxamer 407; or polyethylene glycol (PEG). Polysorbate 20 is also known as TWEEN 20, sorbitan monolaurate and polyoxyethylenesorbitan monolaurate. Poloxamer 188 is also known as PLURONIC F68.

The amount of non-ionic surfactant contained within the pharmaceutical formulations of the present invention may vary depending on the specific properties desired of the formulations, as well as the particular circumstances and purposes for which the formulations are intended to be used. In certain embodiments, the formulations may contain 0.01%±0.0015% to 1%±0.15% surfactant. For example, the formulations of the present invention may comprise about 0.0085%; about 0.01%; about 0.02%; about 0.03%; about 0.04%; about 0.05%; about 0.06%; about 0.07%; about 0.08%; about 0.09%; about 0.1%; about 0.11%; about 0.12%; about 0.13%; about 0.14%; about 0.15%; about 0.16%; about 0.17%; about 0.18%; about 0.19%; about 0.20%; about 0.21%; about 0.22%; about 0.23%; about 0.24%; about 0.25%; about 0.3%; about 0.4%; about 0.5%; about 0.6%; about 0.7%; about 0.8%; about 0.9%; about 1%; about 1.1%; about 1.15%; or about 1.2% polysorbate 20, polysorbate 80 or poloxamer 188.

The pharmaceutical formulations of the present invention may also comprise one or more stabilizers in a type and in an amount that stabilizes the human Ang-2 antibody under conditions of thermal stress. In some embodiments, what is meant by "stabilizes" is maintaining greater than about 93% of the antibody in a native conformation when the solution containing the antibody and the thermal stabilizer is kept at about 45° C. for up to about 28 days. In some embodiments, what is meant by "stabilizes" is wherein less than about 4% of the antibody is aggregated when the solution containing the antibody and the thermal stabilizer is kept at about 45° C. for up to about 28 days. In some embodiments, what is meant by "stabilizes" is maintaining greater than about 96% of the antibody in a native conformation when the solution containing the antibody and the thermal stabilizer is kept at about 37° C. for up to about 28 days. In some embodiments, what is meant by "stabilizes" is wherein less than about 2% of the antibody is aggregated when the solution containing the antibody and the thermal stabilizer is kept at about 37° C. for up to about 28 days. As used herein, "native" means the major form of the antibody by size exclusion, which is generally an intact monomer of the antibody.

In certain embodiments, the thermal stabilizer is a sugar or sugar alcohol selected from sucrose, sorbitol, glycerol, trehalose and mannitol, or any combination thereof, the amount of which contained within the formulation can vary depending on the specific circumstances and intended purposes for which the formulation is used. In certain embodiments, the formulations may contain about 1% to about 20% sugar or sugar alcohol; about 2% to about 18% sugar or sugar alcohol; about 3% to about 15% sugar or sugar alcohol; about 4% to about 10% sugar or sugar alcohol; or about 5% sugar or sugar alcohol. For example, the pharmaceutical formulations of the present invention may comprise 4%±0.6%; 5%±0.75%; 6%±0.9%; 7%±1.05%; 8%±1.2%; 9%±1.35%; 10%±1.5%; 11%±1.65%; 12%±1.8%; 13%±1.95%; or about 14%±2.1% sugar or sugar alcohol (e.g., sucrose, trehalose or mannitol).

In certain embodiments, the pharmaceutical formulations of the present invention comprise a tonicity agent such as sodium chloride or potassium chloride. In some embodiments, the tonicity agent is sodium chloride. In some embodiments, the sodium chloride is present at a concentration of 5 mM±0.75 mM to 100 mM±15.0 mM; 10 mM±1.5 mM to 50 mM±7.5 mM; 40 mM±6.0 mM; or about 40 mM.

The pharmaceutical formulations of the present invention may also comprise a buffer or buffer system, which serves to maintain a stable pH and to help stabilize the human Ang-2 antibody. In some embodiments, what is meant by "stabilizes" is wherein less than 5%±0.5% or no more than about 4.3% of the antibody is aggregated when the solution containing the antibody and the buffer is kept at about 45° C. for up to about 28 days. In some embodiments, what is meant by "stabilizes" is wherein at least 92%±0.5% of the antibody is in its native conformation as determined by size exclusion chromatography when the solution containing the antibody and the buffer is kept at about 45° C. for up to about 28 days. By "native" or "native conformation", what is meant is the antibody fraction that is not aggregated or degraded. This is generally determined by an assay that measures the relative size of the antibody entity, such as a size exclusion chromatographic assay. The non-aggregated and non-degraded antibody elutes at a fraction that equates to the native antibody, and is generally the main elution fraction. Aggregated antibody elutes at a fraction that indicates a size greater than the native antibody. Degraded antibody elutes at a fraction that indicates a size less than the native antibody.

In some embodiments, what is meant by "stabilizes" is wherein at least 52%±0.5% of the antibody is in its main charge form as determined by cation exchange chromatography when the solution containing the antibody and the buffer is kept at about 45° C. for up to about 28 days. By "main charge" or "main charge form", what is meant is the fraction of antibody that elutes from an ion exchange resin in the main peak, which is generally flanked by more "basic" peaks on one side and more "acidic" peaks on the other side.

The pharmaceutical formulations of the present invention may have a pH of from about 5.5 to about 6.5. For example, the formulations of the present invention may have a pH of about 5.5; about 5.6; about 5.7; about 5.8; about 5.9; about 6.0; about 6.1; about 6.2; about 6.3; about 6.4; or about 6.5. In some embodiments, the pH is 6.2±0.3; 6.2±0.2; 6.2±0.1; about 6.2; or 6.2.

In some embodiments, the buffer or buffer system comprises at least one buffer that has a buffering range that overlaps fully or in part the range of pH 5.5-7.4. In one embodiment, the buffer has a pKa of about 6.2±0.5. In certain embodiments, the buffer comprises a sodium phosphate buffer. In certain embodiments, the sodium phosphate is present at a concentration of 5 mM±0.75 mM to 15 mM±2.25 mM; 6 mM±0.9 mM to 14 mM±2.1 mM; 7 mM±1.05 mM to 13 mM±1.95 mM; 8 mM±1.2 mM to 12 mM±1.8 mM; 9 mM±1.35 mM to 11 mM±1.65 mM; 10 mM±1.5 mM; or about 10 mM. In certain embodiments, the buffer system comprises sodium phosphate at 10 mM±1.5 mM, at a pH of 6.2±0.3 or 6.1±0.3.

Exemplary formulations comprising a VEGF antagonist that can be used in the context of the present invention are disclosed, e.g., in U.S. Pat. Nos. 7,531,173 and 7,608,261. Exemplary pharmaceutical compositions comprising an anti-Ang-2 antibody that can be used in the context of the present invention are disclosed, e.g., in US Patent Application Publication No. 20130186797.

Stability of the Pharmaceutical Formulations

The pharmaceutical formulations of the present invention typically exhibit high levels of stability. The term "stable", as used herein in reference to the pharmaceutical formulations, means that the antibodies within the pharmaceutical formulations retain an acceptable degree of chemical structure or biological function after storage under defined conditions. A formulation may be stable even though the antibody contained therein does not maintain 100% of its chemical structure or biological function after storage for a defined amount of time. Under certain circumstances, maintenance of about 90%, about 95%, about 96%, about 97%, about 98% or about 99% of an antibody's structure or function after storage for a defined amount of time may be regarded as "stable".

Stability can be measured, inter alia, by determining the percentage of native antibody that remains in the formulation after storage for a defined amount of time at a defined temperature. The percentage of native antibody can be determined by, inter alia, size exclusion chromatography (e.g., size exclusion high or ultra performance liquid chromatography [SE-HPLC or SE-UPLC]), such that native means non-aggregated and non-degraded. An "acceptable degree of stability", as that phrase is used herein, means that at least 90% of the native form of the antibody can be detected in the formulation after storage for a defined amount of time at a given temperature. In certain embodiments, at least about 90%, 91%, 92%, 93%, 94%, 95%, 96%, 97%, 98%, 99% or 100% of the native form of the antibody can be detected in the formulation after storage for a defined amount of time at a defined temperature. The defined amount of time after which stability is measured can be at least 14 days, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The defined temperature at which the pharmaceutical formulation may be stored when assessing stability can be any temperature from about −80° C. to about 45° C., e.g., storage at about −80° C., about −30° C., about −20° C., about 0° C., about 4°-8° C., about 5° C., about 25° C., about 35° C., about 37° C., or about 45° C. For example, a pharmaceutical formulation may be deemed stable if after nine months of storage at 5° C., greater than about 96%, 96.5%, 97%, 97.5%, 98%, 98.5%, 99% or 99.5% of native antibody is detected by SE-HPLC or SE-UPLC. A pharmaceutical formulation may also be deemed stable if after six months of storage at 25° C., greater than about 96%, 96.5%, 97%, 97.5%, 98%, 98.5%, 99% or 99.5% of native antibody is detected by SE-HPLC or SE-UPLC. A pharmaceutical formulation may also be deemed stable if after 28 days of storage at 37° C., greater than about 96%, 96.5%, 97%, 97.5%, 98%, 98.5%, 99% or 99.5% of native antibody is detected by SE-HPLC or SE-UPLC. A pharmaceutical formulation may also be deemed stable if after 28 days of storage at 45° C., greater than about 93%, 94%, 95%, 96%, 97%, 98% or 99% of native antibody is detected by SE-HPLC or SE-UPLC. A pharmaceutical formulation may also be deemed stable if after six months of storage at −20° C., greater than about 96%, 96.5%, 97%, 97.5%, 98%, 98.5%, 99% or 99.5% of native antibody is detected by SE-HPLC. A pharmaceutical formulation may also be deemed stable if after six months of storage at −30° C., greater than about greater than about 96%, 96.5%, 97%, 97.5%, 98%, 98.5%, 99% or 99.5% of native antibody is detected by SE-HPLC or SE-UPLC. A pharmaceutical formulation may also be deemed stable if after six months of storage at −80° C., greater than about 96%, 96.5%, 97%, 97.5%, 98%, 98.5%, 99% or 99.5% of native antibody is detected by SE-HPLC or SE-UPLC.

Stability can be measured, inter alia, by determining the percentage of antibody that forms in an aggregate within the formulation after storage for a defined amount of time at a defined temperature, wherein stability is inversely proportional to the percent aggregate that is formed. The percentage of aggregated antibody can be determined by, inter alia, size exclusion chromatography (e.g., size exclusion high performance liquid chromatography [SE-HPLC]). An "acceptable degree of stability", as that phrase is used herein, means that at most 6% of the antibody is in an aggregated form detected in the formulation after storage for a defined amount of time at a given temperature. In certain embodiments an acceptable degree of stability means that at most about 6%, 5%, 4%, 3%, 2%, 1%, 0.5%, or 0.1% of the antibody can be detected in an aggregate in the formulation after storage for a defined amount of time at a given temperature. The defined amount of time after which stability is measured can be at least 2 weeks, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The temperature at which the pharmaceutical formulation may be stored when assessing stability can be any temperature from about −80° C. to about 45° C., e.g., storage at about −80° C., about −30° C., about −20° C., about 0° C., about 4°-8° C., about 5° C., about 25° C., about 35° C., about 37° C. or about 45° C. For example, a pharmaceutical formulation may be deemed stable if after nine months of storage at 5° C., less than about 2%, 1.75%, 1.5%, 1.25%, 1%, 0.75%, 0.5%, 0.25%, or 0.1% of the antibody is detected in an aggregated form. A pharmaceutical formulation may also be deemed stable if after six months of storage at 25° C., less than about 2%, 1.75%, 1.5%, 1.25%, 1%, 0.75%, 0.5%, 0.25%, or 0.1% of the antibody is detected in an aggregated form. A pharmaceutical formulation may also be deemed stable if after 28 days of storage at 45° C., less than about 4%, 3.5%, 3%, 2.5%, 2%, 1.5%, 1%, 0.5%, or 0.1% of the antibody is detected in an aggregated form. A pharmaceutical formulation may also be deemed stable if after three months of storage at −20° C., −30° C., or −80° C. less than about 2%, 1.9%, 1.8%, 1.7%, 1.6%, 1.5%, 1%, 0.5%, or 0.1% of the antibody is detected in an aggregated form.

Stability can be measured, inter alia, by determining the percentage of antibody that migrates in a more acidic fraction during ion exchange ("acidic form") than in the main fraction of antibody ("main charge form"), wherein stability is inversely proportional to the fraction of antibody in the acidic form. While not wishing to be bound by theory, deamidation of the antibody may cause the antibody to become more negatively charged and thus more acidic relative to the non-deamidated antibody (see, e.g., Robinson, N., Protein Deamidation, *PNAS, Apr.* 16, 2002, 99(8):5283-5288). The percentage of "acidified" antibody can be determined by ion exchange chromatography (e.g., cation exchange high performance liquid chromatography [CEX-HPLC]). An "acceptable degree of stability", as that phrase is used herein, means that at most 52% of the antibody is in a more acidic form detected in the formulation after storage for a defined amount of time at a defined temperature. In certain embodiments an acceptable degree of stability means that at most about 52%, 50%, 45%, 40%, 35%, 30%, 29%, 28%, 27%, 26%, 25%, 20%, 15%, 10%, 5%, 4%, 3%, 2%, 1%, 0.5%, or 0.1% of the antibody can be detected in an acidic form in the formulation after storage for a defined amount of time at a given temperature. The defined amount of time after which stability is measured can be at least 2 weeks, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The temperature at which the pharmaceutical formulation may be stored when assessing stability can be any temperature from about −80° C. to about 45° C., e.g., storage at about −80° C., about −30° C., about −20° C., about 0° C., about 4°-8° C., about 5° C., about 25° C., or about 45° C. For example, a pharmaceutical formulation may be deemed stable if after three months of storage at −80° C., −30° C., or −20° C. less than about 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after nine months of storage at 5° C., less than about 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after 28 days of storage at 25° C., less than about 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after 28 days of storage at 37° C., less than about 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after 28 days of storage at 45° C., less than about 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody can be detected in a more acidic form.

Measuring the binding affinity of the antibody to its target may also be used to assess stability. For example, a formulation of the present invention may be regarded as stable if, after storage at e.g., −80° C., −30° C., −20° C., 5° C., 25° C., 37° C., 45° C., etc. for a defined amount of time (e.g., 14 days to 6 months), the anti-Ang-2 antibody contained within the formulation binds to Ang-2 with an affinity that is at least 84%, 90%, 95%, or more of the binding affinity of the antibody prior to said storage. Binding affinity may be determined by any method, such as e.g., ELISA or plasmon resonance. Biological activity may be determined by an Ang-2 activity assay, such as by contacting a cell that expresses Ang-2 with the formulation comprising the anti Ang-2 antibody. The binding of the antibody to such a cell may be measured directly, such as via FACS analysis. Alternatively, the downstream activity of the Ang-2 system may be measured in the presence of the antibody, and compared to the activity of the Ang-2 system in the absence of antibody. In some embodiments, the Ang-2 may be endogenous to the cell. In other embodiments, the Ang-2 may be ectopically expressed (i.e., heterologous expression) in the cell.

Additional methods for assessing the stability of an antibody in formulation are demonstrated in the Examples presented below.

Containers and Methods of Administration

Various delivery systems are known and can be used to administer the pharmaceutical composition of the invention, e.g., encapsulation in liposomes, micro-particles, microcapsules, recombinant cells capable of expressing the mutant viruses, receptor mediated endocytosis (see, e.g., Wu et al., 1987, J. Biol. Chem. 262: 4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

For the treatment of eye disorders, the pharmaceutical formulations of the invention may be administered, e.g., by eye drops, subconjunctival injection, subconjunctival implant, intravitreal injection, intravitreal implant, sub-Tenon's injection or sub-Tenon's implant.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used. In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

The pharmaceutical formulations of the present invention may be contained within any container suitable for storage or administration of medicines and other therapeutic compositions. For example, the pharmaceutical formulations may be contained within a sealed and sterilized plastic or glass container having a defined volume such as a vial, ampule, syringe, cartridge, bottle, or IV bag. Different types of vials can be used to contain the formulations of the present invention including, e.g., clear and opaque (e.g., amber) glass or plastic vials. Likewise, any type of syringe can be used to contain or administer the pharmaceutical formulations of the present invention.

The pharmaceutical formulations of the present invention may be contained within "normal tungsten" syringes or "low tungsten" syringes. As will be appreciated by persons of ordinary skill in the art, the process of making glass syringes generally involves the use of a hot tungsten rod which functions to pierce the glass thereby creating a hole from which liquids can be drawn and expelled from the syringe. This process results in the deposition of trace amounts of tungsten on the interior surface of the syringe. Subsequent washing and other processing steps can be used to reduce the amount of tungsten in the syringe. As used herein, the term "normal tungsten" means that the syringe contains greater than or equal to 500 parts per billion (ppb) of tungsten. The term "low tungsten" means that the syringe contains less than 500 ppb of tungsten. For example, a low tungsten syringe, according to the present invention, can contain less than about 490, 480, 470, 460, 450, 440, 430, 420, 410, 390, 350, 300, 250, 200, 150, 100, 90, 80, 70, 60, 50, 40, 30, 20, 10 or fewer ppb of tungsten.

The rubber plungers used in syringes, and the rubber stoppers used to close the openings of vials, may be coated to prevent contamination of the medicinal contents of the syringe or vial, or to preserve their stability. Thus, pharmaceutical formulations of the present invention, according to certain embodiments, may be contained within a syringe that comprises a coated plunger, or within a vial that is sealed with a coated rubber stopper. For example, the plunger or stopper may be coated with a fluorocarbon film. Examples of coated stoppers or plungers suitable for use with vials and syringes containing the pharmaceutical formulations of the present invention are mentioned in, e.g., U.S. Pat. Nos. 4,997,423; 5,908,686; 6,286,699; 6,645,635; and 7,226,554, the contents of which are incorporated by reference herein in their entireties. Particular exemplary coated rubber stoppers and plungers that can be used in the context of the present invention are commercially available under the tradename "FluroTec®", available from West Pharmaceutical Services, Inc. (Lionville, Pa.). FluroTec® is an example of a flurocarbon coating used to minimize or prevent drug product from adhering to the rubber surfaces.

According to certain embodiments of the present invention, the pharmaceutical formulations may be contained within a low tungsten syringe that comprises a fluorocarbon-coated plunger.

The pharmaceutical formulations can be administered to a patient by parenteral routes such as injection (e.g., subcutaneous, intravenous, intramuscular, intraperitoneal, etc.) or percutaneous, mucosal, nasal, pulmonary or oral administration. Numerous reusable pen or autoinjector delivery devices can be used to subcutaneously deliver the pharmaceutical formulations of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany). Examples of disposable pen or autoinjector delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park, Ill.).

The use of a microinfusor to deliver the pharmaceutical formulations of the present invention is also contemplated herein. As used herein, the term "microinfusor" means a subcutaneous delivery device designed to slowly administer large volumes (e.g., up to about 2.5 mL or more) of a therapeutic formulation over a prolonged period of time (e.g., about 10, 15, 20, 25, 30 or more minutes). See, e.g., U.S. Pat. Nos. 6,629,949; 6,659,982; and Meehan et al., *J. Controlled Release* 46:107-116 (1996). Microinfusors are particularly useful for the delivery of large doses of therapeutic proteins contained within high concentration (e.g., about 100, 125, 150, 175, 200 or more mg/mL) or viscous solutions.

In one embodiment, the pharmaceutical formulation is administered via an IV drip, such that the formulation is diluted in an IV bag containing a physiologically acceptable solution. In one embodiment, pharmaceutical composition is a compounded sterile preparation in an intravenous infusion bag, such that a single dose of drug product is diluted into 100 mL, 250 mL (or other like amount suitable for intravenous drip delivery) of a physiological buffer (e.g., 0.9% saline). In some embodiments, the infusion bag is made of a polyvinyl chloride (e.g., VIAFLEX, Baxter, Deerfield, Ill.). In some embodiments, the infusion bag is made of a polyolefin (EXCEL IV Bags, Braun Medical Inc., Bethlehem, Pa.).

In certain embodiments, the liquid formulation comprising of from 10 mg/mL to 120 mg/mL of anti-Ang-2 antibody is comprised in a prefilled syringe and is administered intravitreally in a volume of approximately upto 100 μL. In certain embodiments, the liquid formulation comprising of from 10 mg/mL to 120 mg/mL of anti-Ang-2 antibody and from 10 mg/mL to 100 mg/mL of aflibercept is comprised in a prefilled syringe and is administered intravitreally in a volume of approximately upto 100 μL. In certain embodiments, the liquid formulation comprising of from 10 mg/mL to 120 mg/mL of anti-Ang-2 antibody and from 10 mg/mL to 100 mg/mL of aflibercept is in a prefilled syringe and is administered intravitreally in a volume of approximately upto 500 μL. In certain embodiments, the liquid formulation comprising of from 60 mg/mL to 120 mg/mL of anti-Ang-2 antibody and about 40 mg/mL of aflibercept is in a prefilled syringe and is administered intravitreally in a volume of approximately upto 500 μL. In one embodiment, the syringe is a 2 mL long glass syringe fitted with a 30-gauge thin wall needle, a fluorocarbon coated rubber plunger and a rubber needle shield. In one embodiment, the syringe is a 1 mL long glass syringe fitted with a 30-gauge thin wall needle, a fluorocarbon coated rubber plunger and a rubber needle shield.

Administration Regimens

The present invention includes methods comprising administering to a subject a pharmaceutical composition comprising an anti-Ang-2 antibody at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments, the methods involve the administration of a pharmaceutical composition comprising an anti-Ang-2 antibody in combination with a VEGF antagonist at a dosing frequency of about four times a week, twice a week, once a week, once every two weeks, once every three weeks, once every four weeks, once every five weeks, once every six weeks, once every eight weeks, once every nine weeks, once every twelve weeks, or less frequently so long as a therapeutic response is achieved.

According to certain embodiments of the present invention, multiple doses of an anti-Ang-2 antibody may be administered to a subject over a defined time course. The methods according to this aspect of the invention comprise sequentially administering to a subject multiple doses of an anti-Ang-2 antibody. As used herein, "sequentially administering" means that each dose of anti-Ang-2 antibody is administered to the subject at a different point in time, e.g., on different days separated by a predetermined interval (e.g., hours, days, weeks or months). The present invention includes methods which comprise sequentially administering to the patient a single initial dose of an anti-Ang-2 antibody, followed by one or more secondary doses of the anti-Ang-2 antibody, and optionally followed by one or more tertiary doses of the anti-Ang-2 antibody.

According to certain embodiments of the present invention, multiple doses of a co-formulation comprising an anti-Ang-2 antibody and a VEGF antagonist may be administered to a subject over a defined time course. The methods according to this aspect of the invention comprise sequentially administering to a subject multiple doses of a co-formulation comprising an anti-Ang-2 antibody and a VEGF antagonist. As used herein, "sequentially administering" means that each dose of the anti-Ang-2 antibody in combination with the VEGF antagonist is administered to the subject at a different point in time, e.g., on different days separated by a predetermined interval (e.g., hours, days, weeks or months). The present invention includes methods which comprise sequentially administering to the patient a single initial dose of a co-formulation comprising an anti-Ang-2 antibody and a VEGF antagonist, followed by one or more secondary doses of the co-formulated anti-Ang-2 antibody and VEGF antagonist, and optionally followed by one or more tertiary doses of the co-formulated anti-Ang-2 antibody and VEGF antagonist.

The terms "initial dose," "secondary doses," and "tertiary doses," refer to the temporal sequence of administration. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-Ang-2 antibody (or a co-formulation comprising anti-Ang-2 antibody and VEGF antagonist), but generally may differ from one another in terms of frequency of administration. In certain embodiments, however, the amount contained in the initial, secondary and/or tertiary doses varies from one another (e.g., adjusted up or down as appropriate) during the course of treatment. In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses"). For example, an anti-Ang-2 antibody (or a co-formulation comprising anti-Ang-2 antibody and VEGF antagonist) may be administered to a patient with an eye disease or disorder at a loading dose of about 6 mg followed by one or more maintenance doses of about 0.5 mg to about 10 mg.

In one exemplary embodiment of the present invention, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of anti-Ang-2 antibody (or a co-formulation comprising anti-Ang-2 antibody and VEGF antagonist) which is administered to a patient prior to the administration of the very next dose in the sequence with no intervening doses.

The methods according to this aspect of the invention may comprise administering to a patient any number of secondary and/or tertiary doses of an anti-Ang-2 antibody (or a co-formulation comprising anti-Ang-2 antibody and VEGF antagonist). For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes methods comprising sequential administration of an anti-Ang-2 antibody in combination with a VEGF antagonist, to a patient to treat DME or AMD. In some embodiments, the present methods comprise administering one or more doses of an anti-Ang-2 antibody followed by one or more doses of a VEGF antagonist. In certain embodiments, the present methods comprise administering a single dose of a VEGF antagonist followed by one or more doses of an anti-Ang-2 antibody. In some embodiments, one or more doses of about 0.05 mg to about 2 mg of a VEGF antagonist may be administered followed by one or more doses of about 0.05 mg to about 10 mg of the Ang-2 inhibitor. In one embodiment, one or more doses of about 1 mg/kg to about 15 mg/kg of subject body weight of anti-Ang-2 antibody may be administered after which one or more doses of VEGF antagonist may be administered to treat, alleviate, reduce or ameliorate one or more conditions associated with DME or AMD (e.g., angiogenesis inhibition). In some embodiments, the anti-Ang-2 antibody is administered at one or more doses resulting in an improvement in one or more parameters (e.g., retinal thickening, visual acuity) followed by the administration of a VEGF antagonist (e.g., aflibercept) to prevent recurrence or have additive activity. Alternative embodiments of the invention pertain to concomitant administration of anti-Ang-2 antibody and a VEGF antagonist which is administered at a separate dosage at a similar or different frequency relative to the anti-Ang-2 antibody. In some embodiments, the VEGF antagonist is administered before, after or concurrently with the anti-Ang-2 antibody. In certain embodiments, the VEGF antagonist is administered as a single dosage formulation with the anti-Ang-2 antibody.

Dosage

The amount of Ang-2 inhibitor (e.g., anti-Ang-2 antibody) administered to a subject according to the methods of the present invention is, generally, a therapeutically effective amount. As used herein, the phrase "therapeutically effective amount" means an amount of Ang-2 inhibitor that results in one or more of: (a) a reduction in the severity of retinal vascular leak; (b) a reduction in the area of retinal or choroidal neo-vascularization; (c) change in central retinal thickness; (d) an increase in the duration of suppression of vascular leak in the eye; and (e) a reduction in the number of intravitreal injections in a subject having an eye disease or disorder associated with angiogenesis.

In the case of an anti-Ang-2 antibody, a therapeutically effective amount can be from about 0.05 mg to about 100 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, or about 100 mg, of the anti-Ang-2 antibody. In certain embodiments, 0.5 mg, 1.0 mg, 3.0 mg or 6.0 mg of an anti-Ang-2 antibody is administered.

The amount of Ang-2 inhibitor contained within the individual doses may be expressed in terms of milligrams of antibody per kilogram of patient body weight (i.e., mg/kg). For example, the Ang-2 inhibitor may be administered to a patient at a dose of about 0.0001 to about 100 mg/kg of patient body weight.

In certain embodiments, 0.5 mg, 1.0 mg, 3.0 mg or 6.0 mg of an anti-Ang-2 antibody is administered in combination with 0.05 mg to about 10 mg of a VEGF antagonist (e.g., aflibercept).

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Effects of Combined Inhibition of VEGF and Ang2 Using Aflibercept (VEGF Trap) and Anti-Ang2 Antibody on the Developing Retinal Angiogenesis in Mice Introduction: VEGF is the key modulator of angiogenesis in normal and pathological angiogenesis. However, other growth factors are also involved in angiogenesis and are able to mediate blood vessel resistance to anti-VEGF therapies. Angiopoietin-2 (Ang2) was shown to be involved in blood vessel growth and regression in various circumstances in a context-dependent manner. In this study we tested the effects of VEGF blockade using aflibercept alone and in combination with Ang2 inhibition with an anti-Ang2 antibody on blood vessel growth and regression in a normal retinal vascular development (RVD) model.

Human anti-Ang-2 antibodies were generated as described in US Patent Application Publication No. US20110027286. The exemplary anti-Ang-2 antibody used in the present and following Examples is the human anti-Ang-2 antibody designated as H1H685 with HCVR/LCVR of SEQ ID NOs: 1/2 (also referred to herein as "mAb1").

In a first experiment, anti-Ang-2 antibody alone or in combination with aflibercept was administered intravitreally.

Methods: Normal C57Bl/6 mouse pups were treated with aflibercept and anti-Ang2 antibody individually or in combination from postnatal day 4 (P4) to P6. Pups were injected IVT on P4 with 5 µg of a control protein (hFc), 5 µg mAb1 (anti-Ang2 antibody), or 1.25 µg aflibercept, as single agents, or mixture of both aflibercept and mAb1. Pups were humanely euthanized at P6, the eyes were removed and fixed in 4% paraformaldehyde. The retinas were then dissected and stained with FITC labeled GS Lectin I (for vascular endothelial cells).

Results: P4 was selected as the starting point for treatment with mAb1 to assess the effect of Ang2 and/or VEGF inhibition on RVD. Administration of mAb1 or aflibercept reduced the outgrowth of the superficial retinal vasculature compared to hFc treated controls. Specifically, mAb1 and aflibercept decreased the mean vascularized area of the retina by 17% and 36%, respectively, relative to hFc controls, while combined treatment with both mAb1 and aflibercept reduced vascular area by 72%, representing complete arrest of retinal vascular development over the treatment period (compared to retinal vascular area at P4). mAb1 and aflibercept also decreased the mean vessel length by 23% and 22%, respectively, compared to hFc controls. Combined treatment with mAb1 and aflibercept had a significant synergistic effect, leading to a dramatic 77% decrease in total vessel length. Total blood vessel length was even smaller by 25% in the combination treated samples compared to P4 retinas.

In a second experiment, doses of mAb1 (25 mg/kg, subcutaneous [SC]) and aflibercept (25 mg/kg, SC) utilized were in excess of the minimal doses required to obtain maximal suppression of retinal angiogenesis when each drug is used as a single agent. Administration of either mAb1 or aflibercept on P3 significantly reduced the mean vascularized area of the retina measured at P6 by 36% and 42%, respectively, relative to hFc controls. Moreover, the mean vascularized area of the retina was significantly smaller in the animals treated with both mAb1 and aflibercept, compared to animals treated with either agent alone, being reduced by 68%, representing a near complete arrest of retinal vascular development over the treatment period.

Conclusions: Combined pharmacological inhibition of Ang2 and VEGF-A had a greater effect on developmental retinal angiogenesis than administration of Ang2 or VEGF-A blocker alone, such that inhibition of both Ang2 and VEGF-A resulted in a near completed arrest of retinal vascular development during the treatment period and partial blood vessel regression compared to the initial treatment conditions at P4.

Example 2: Effect of IVT Injection of Co-Formulated mAb1 and Aflibercept on DL-Alpha-Aminoadipic Acid (DL-Alpha-AAA)—Induced Retinal Neovascularization (RNV) in Rabbit Eyes The glial toxin DL-alpha-AAA targets retinal Muller cells and astrocytes and leads to neovascularization and chronic vascular leak lasting at least 12 months (Kato et al 1993; Neuroscience 57: 473). The purpose of this study was to evaluate the effects of IVT injection of co-formulated Anti-Ang2 and aflibercept on RNV induced by DL-alpha-AAA.

Methods: Male New Zealand White Rabbits (>2 kg body weight) were treated with a single intravitreal injection of DL-alpha-AAA to induce RNV. The leak was monitored and quantitated non-invasively using fluorescein angiography (FA). Pathological vasculature and a relatively invariable leakage area were established over 13 weeks post injection. Upon disease establishment, the subjects were split into three groups for treatment, as shown below:

Group I: 125 µg/50 µl of aflibercept IVT
Group II: 500 µg/50 µl of mAb1 IVT
Group III: Co-formulated 125 µg aflibercept and 500 µg mAb1/50 µl, IVT A baseline examination was performed prior to first treatment to balance treatment groups. Follow-up examinations were performed on wk 1, 2, 3, 4, 5, 6, 7, and 8 Post-IVT treatments. Leakage area was quantified using Adobe Photoshop after fluorescein angiography (FA) analysis. A fluorescent agent was administered intravenously to monitor vessel leak and ocular coherence tomography using light waves was used to monitor retinal structure.

Results: As shown in FIG. 1, leakage was shown to return at week 3 in aflibercept-treated subjects, whereas leakage area did not change till week 8 in subjects treated with mAb1 and aflibercept combination. Co-treatment of aflibercept and mAb1 can significantly enhance the duration of anti-leak effects up to 3-fold compared to a single IVT injection of aflibercept alone.

Example 3: Systemic Administration of mAb1 Alone or Co-Treatment with VEGF Trap-Eye IVT on DL-AAA Induced Retinal Neo-Vascular Leak in Rabbit Eyes The purpose of this study was to evaluate the effects of co-treatment of Anti-Ang2 antibody and aflibercept on RNV induced by DL-alpha-AAA, wherein the intravitreal administration of aflibercept was followed by systemic administrations of mAb1. The rationale of this study was to try and maintain the suppression of leakage over longer periods of time with an initial IVT injection of aflibercept and follow up with systemic injections once in two weeks (q2w) of anti-Ang 2 antibody.

Figure 2:
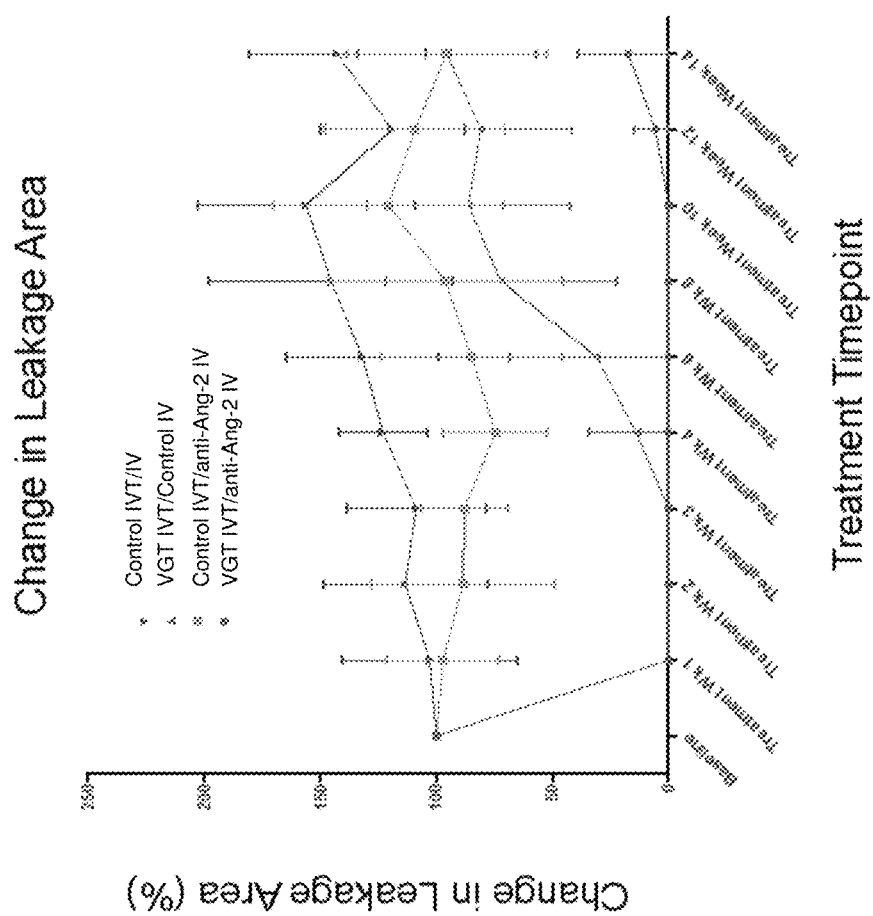
FIG. 2 shows the percent change in leakage area in rabbits with DL-alpha-AAA—induced retinal neovascularization which have been intravitreally (IVT) treated with VEGF antagonist (VGT) (or control) and intravenously (IV) treated with anti-Ang-2 antibody (or control) according to the following therapeutic regimen, as described in Example 3 herein: (a) control IVT and control IV; (b) VGT IVT and control IV; (c) control IVT and anti-Ang-2 IV; and (d) VGT IVT and anti-Ang-2 antibody IV.

As disclosed in Example 2, retinal neovascularization was induced in male New Zealand rabbits with a single intravitreal injection of DL-alpha-AAA. Stable retinal neovascularization and vascular leak was established 10 weeks post induction. After ten weeks of disease establishment, the subjects were split into four groups with balanced leakage severity and treatment was administered as shown below:

Group 1: Control 42 µg/50 µl, IVT and Control 5 mg/kg, IV, q2w
Group 2: Control 42 µg/50 µl, IVT and mAb1 (anti-Ang2 ab) 15 mg/kg, IV, q2w
Group 3: Aflibercept 125 µg/50 µl, IVT and Control 5 mg/kg, IV, q2w
Group 4: Aflibercept 125 µg/50 µl, IVT and mAb1 (a-Ang2) 15 mg/kg, IV, q2w Analysis of leakage area by Fluorescein Angiography (FA); Baseline fluorescein angiography (FA) and optic coherent tomography (OCT) prior to $1^{st}$ treatment; Follow-up FA and OCT on Week 1, 2, 3, 4, 6, 8, 10, 12 and 14 Post-IV treatment As shown in FIG. 2, there was no leakage in aflibercept-treated eyes in week 2. Leakage was shown to return at week 4 with aflibercept treatment alone. However there was no leakage till week 10 in subjects treated with the combination of aflibercept and mAb1. Initial return of leakage was shown in week 12 in co-treated subjects.

Example 4: IVT Injection of Aflibercept on DL-Alpha-AAA Induced RNV and Vascular Leak in Rabbit Eye This study is a dose-ranging study on the effect of IVT aflibercept monotherapy on DL-alpha-AAA induced retinal neovascularization (RNV) and vascular leak in rabbit eye. As disclosed in Example 2, DL-alpha-AAA was used to induce RNV in rabbit eyes. Upon establishment of RNV and vascular leak, the subjects were treated with 4 doses of aflibercept: 50 mcg, 125 mcg, 250 mcg, and 500 mcg. Retinal vascular leak was monitored and quantitated by FA (as disclosed elsewhere herein) at follow-up time points on weeks 1, 2, 3, 4, 5, 6, 8 10 and 12 post-IVT.

Without treatment, FA showed that retinal NV and vascular leak remain consistent from weeks 10 to 22. Table 1 shows the mean time of leak recurrence after treatment wherein "first leak recurrence"=time for recurrence of any leak, not full recurrence.

TABLE 1

Mean time of first leak recurrence

| IVT VTE dose | Mean (wks) | STD (wks) | Range (wks) |
|---|---|---|---|
| 500 mcg (n = 4) | 9 | 2 | 8-12 |
| 250 mcg (n = 3) | 6.3 | 1.5 | 5-8 |
| 125 mcg (n = 2) | 4.5 | 0.7 | 4-5 |
| 50 mcg (n = 2) | 2.5 | 0.7 | 2-3 |

500 mcg of aflibercept blocked retinal NV leak within 1 week, and leak did not resume until week 12 after treatment. Thus aflibercept treatment leads to suppression of vascular leak and partial regression of neovascularization. Vascular leakage reoccurs but length of suppression is dose dependent.

Example 5: Systemic Administration of Anti-Ang-2 Antibody Inhibits Matrigel-Induced Choroidal Neovascularization (CNV) in Rats Introduction: Ang2 is a ligand for the tyrosine kinase receptor Tie-2 and is broadly expressed in the vascular endothelium of developing blood vessels and in vessels undergoing active growth or remodeling in diverse physiological and pathophysiological conditions. mAb1 is a human monoclonal, neutralizing antibody against Ang-2. The study utilized a rat model of choroidal neovascularization (CNV) to assess the inhibitory effects of mAb1-mediated pharmacological inhibition of Ang-2 on CNV.

Methods:

CNV was induced in Sprague Dawley (SD) rats by a subretinal injection of Matrigel on Day 0. One group of animals (animals: N=4-6; eyes: N=8-12) was used to establish a baseline and animals were perfused with a dye [1,1'-Dioctadecyl-3,3,3',3'-Tetramethylindocarbocyanine Perchlorate (DiI)] to stain vessels 10 days after CNV induction. The other animals were divided into two groups (animals: N=5-6, and eyes: N=10-12, in each group) and treated with masked solutions by subcutaneous injection of 25 mg/kg mAb1, or 6.5 mg/kg hFc at equimolar amount relative to mAb1, respectively, on days 10, 13, and 16 followed by perfusion with DiI to stain vessels on Day 20. Subretinal lesion and CNV vessel volumes were quantified from 50 μm sections throughout the entire lesion using the formula $$V = T \times \sum_{i=1}^{n} A_i$$

wherein V: Total Lesion Volume;
T: Section Thickness;
A: Area of lesion or vessels on each section The results from two identical experiments were combined for lesion volume, vessel volume, and vessel density comparison among three groups. A two-tailed Student t-test was used to compare the differences of lesion volume, vessel volume, and vessel density between groups treated with mAb1 versus control. Concentrations of functional mAb1 and levels of anti-mAb1 antibodies in rat serum were measured using a direct enzyme linked immunosorbent assay (ELISA).

Figure 3:
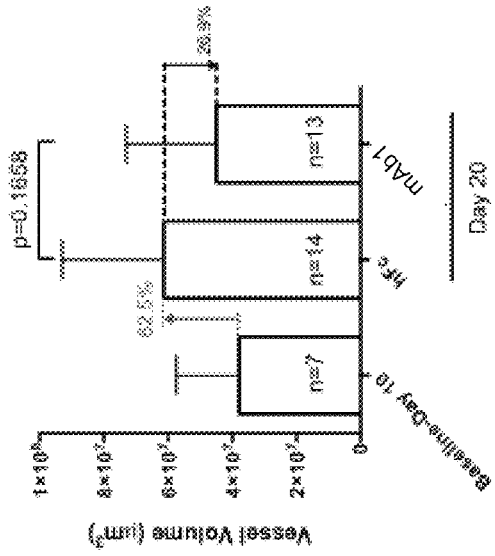
FIG. 3 shows quantification of the total subretinal lesion size (A), neovessel volume (B), and vessel density (C) of baseline, control (hFc), and anti-Ang-2 antibody (mAb1) treated groups, as described in Example 5 herein. Compared to hFc-treated controls, the mAb1-treated group showed statistically significant reduction of total lesion volume (Student t-test, p=0.0034), and a trend (26.9%) towards neovessel volume reduction (Student t-test, p=0.1658). Error bars indicate standard deviation.
Figure 3:
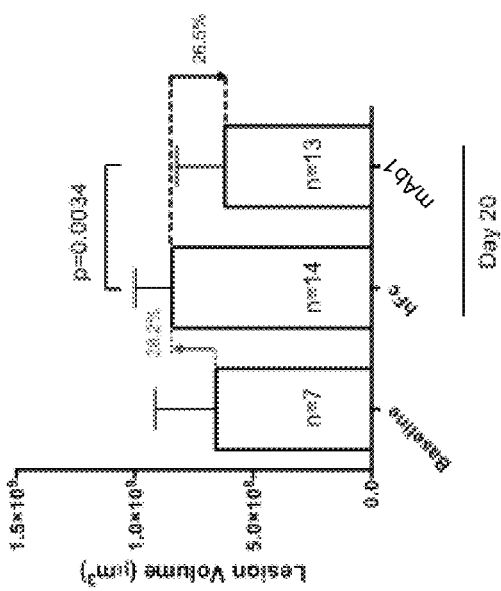

Results:

Systemic administration of mAb1 (25 mg/kg) to SD rats produced a suppression of the total lesion volume and vessel volume compared to hFc-treated control (FIG. 3). In the control treated group, subretinal lesion volume, neovessel volume, and neovessel density increased by 28.2%, 62.5%, and 28.6%, respectively, by Day 20, relative to the baseline at Day 10. The mAb1 treated group showed 26.5% reduction of total lesion volume, and 26.9% reduction of vessel volume, compared to hFc treated group, though the vessel density was unchanged compared to the hFc treated group (FIG. 3). Compared to hFc-treated controls, the mAb1 treated group showed statistically significant reduction of total lesion volume (Student t-test, p=0.0034), and a trend (26.9%) towards neovessel volume reduction, but this trend did not achieve statistical significance (Student t-test, p=0.1658, which may have been due to variation within the group. Bioanalytical analysis of functional mAb1 and anti-mAb1 antibodies in rat serum samples showed measurable concentrations of functional mAb1 in mAb1-treated animals with levels of 504±107 μg/mL on terminal date (Day 20) (Table 2). Individual anti-mAb1 responses were negative.

TABLE 2

Concentration of mAb1 and anti-mAb1 antibodies in rat serum samples

|  | mAb1 (μg/mL) (Mean ± SD) | Anti-mAb1 antibody |
|---|---|---|
| IVT mAb1 | 504 ± 107 | (−) |
| IVT hFc | BLQ | (−) |

BLQ: Below Limit of Quantification (<0.078 μg/mL)
(−): Antibody negative

Conclusions:

The effects of mAb1, a neutralizing, human monoclonal antibody against Ang2, were evaluated in Matrigel induced CNV in SD rats. The results indicate that systemic (subcutaneous) treatment with mAb1 can significantly inhibit Matrigel induced CNV lesion in rats. Thus, this Example provides additional support for the use of Ang-2 inhibitors (such as mAb1) as a systemic monotherapy to treat vascular eye diseases.

Example 6: Formulation Comprising an Anti-Ang-2 Antibody

Formulation development activities included the screening of buffers, organic co-solvents, and thermal stabilizers in liquid formulations of anti-Ang-2 antibody to identify excipients that enhance the stability of the protein. Buffer conditions were also examined to determine the optimal pH for maximum protein stability. Results generated from these studies were used to develop a stable, liquid formulation suitable for clinical use. The anti-Ang-2 antibody is the human anti-Ang-2 antibody with HCVR/LCVR of SEQ ID NOs: 1/2 and designated as H1H685 in US Patent Application Publication US20110027286 (also referred to herein as "mAb1").

The anti-Ang-2 antibody was formulated at four concentrations:
(i) 10 mg/mL±1.5 mg/mL,
(ii) 20 mg/mL±3.0 mg/mL,
(iii) 60 mg/mL±9.0 mg/mL, and
(iv) 120 mg/mL±18.0 mg/mL.

In various embodiments, the anti-Ang-2 antibody is formulated in 10±1.5 mM sodium phosphate (pH 6.2±0.3), 0.03%±0.0045% polysorbate 20, 40 mM±6.0 mM sodium chloride, and 5%±0.75% sucrose, in water.

The stability of the formulated drug substance and drug product was assessed using the following assays:

Color and appearance by visual inspection; pH; turbidity measured by increase in optical density at 405 nm; subvisible particulate analysis by microflow imaging (MFI); protein concentration by RP-HPLC; purity by size exclusion ultra-performance liquid chromatography (SE-UPLC); reduced and non-reduced SDS-PAGE; charged variant analysis by cation exchange UPLC; potency by bioassay. Additional details are described in Example 8.

Stability studies were initiated to determine the storage, accelerated (temperatures above storage conditions), and stress (agitation and freezing and thawing) stability of research lots of 10 mg/mL mAb1, and 120 mg/mL mAb1 FDS. These conditions were chosen to bracket the protein concentrations of FDS that used to manufacture the clinical DP. Evaluation of research lots of FDS under accelerated and stress conditions was performed by subjecting FDS to a variety of tests designed to exceed stresses the FDS may encounter during the manufacture of DP and to elucidate the degradation pathways for mAb1 FDS. FDS was filled in 5 mL polycarbonate vials The research stability of the drug substance was studied as shown in Tables 3 and 4:

TABLE 3

Research Stability Study for mAb1 Formulated Drug Substance

| | Storage Stability[1] | Container/Closure |
|---|---|---|
| Storage Temperature | Length of Storage (months) | 5 mL Nalge-Nunc |
| −80° C. | 0, 1, 3, 6, 9, 12, 18, 24, and 36 | polycarbonate vial with lined closure |
| −30° C. | 0, 1, 3, 6, 9, 12, 18, 24, and 36 | |
| −20° C. | 0, 1, 3, 6, 9, 12, 18, 24, and 36 | |
| Accelerated Stability[2] | | |
| Incubation Condition | Length of Incubation | |
| 5° C. | 0, 14, 28, and 56 days | |
| 25° C./60% RH | 0, 7, 14, and 28 days | |
| 40° C./75% RH | 0, 7, 14, and 28 days | |
| Stress Stability | | |
| Stress | Duration of Stress | |
| Agitation (vortex) | 0, 60, and 120 minutes | |
| Freeze/Thaw[3] | 0, 4, and 8 cycles | |

TABLE 4

Analysis Plan for mAb1 Formulated Drug Substance Research Stability Study

| Assay | Samples to be Analyzed |
|---|---|
| Color and Appearance | All Samples |
| pH | All Samples |
| Turbidity (Increase in OD at 405 nm) | All Samples |
| % mAb1 Recovered by RP-HPLC | All Samples |
| % mAb1 Purity by Non-Reduced and Reduced SDS-PAGE | t = 0, 6, 12, 24 and 36 months at −80° C., −30° C., and −20° C. 56 days at 5° C., 28 days at 25° C./60% RH and 40° C./75% RH 120 min Agitation, 8X Freeze/Thaw |
| % Purity by SE-UPLC | All Samples |
| Charge Variant Analysis by CEX-UPLC | All Samples |
| Charge Variant Analysis by iCIEF | All Samples |
| % mAb1 Relative Potency by Bioassay | t = 0, 6, 12, 24 and 36 months at −80° C. and −20° C. 56 days at 5° C., 28 days at 25° C./60% RH and 40° C./75% RH 120 min Agitation, 8X Freeze/Thaw |

The results of the stability studies are summarized in Tables 5-14 below:

TABLE 5

Research Stability of 10 mg/mL mAb1 Formulated Drug Substance Stored at −80° C.

| Formulation | 10 mg/mL mAb1, 10 mM sodium phosphate, 40 mM sodium chloride, 5% (w/v) sucrose, 0.03% (w/v) polysorbate 20, pH 6.2 |
|---|---|
| Fill Volume | 1.0 mL |
| Container/Closure | 5 mL polycarbonate vial with silicone lined polypropylene screw cap |

| | Length of Storage (months) | | | | | |
|---|---|---|---|---|---|---|
| Assay | 0 | 1 | 3 | 6 | 9 | 12 |
| Color and Appearance | Pass | Pass | Pass | Pass | Pass | Pass |
| Turbidity (Increase in OD at 405 nm) | 0.00 | 0.00 | 0.00 | 0.00 | 0.00 | 0.00 |
| pH | 6.2 | 6.2 | 6.2 | 6.3 | 6.2 | 6.2 |
| % Total mAb1 Recovered by RP-HPLC | 100 | 100 | 104 | 104 | 104 | 100 |

TABLE 5-continued

Research Stability of 10 mg/mL mAb1 Formulated Drug Substance Stored at −80° C.

| | | | | | | | |
|---|---|---|---|---|---|---|---|
| Purity by SDS-PAGE | Non-reduced; % main peak | 95 | NR | NR | 94 | NR | 95 |
| | Reduced; % heavy + light chain | 100 | NR | NR | 100 | NR | 100 |
| Purity by SE-UPLC | % HMW | 2.3 | 2.4 | 2.4 | 2.4 | 2.4 | 2.4 |
| | % Native | 96.8 | 96.4 | 96.5 | 96.4 | 96.6 | 96.7 |
| | % LMW | 0.9 | 1.2 | 1.1 | 1.2 | 1.0 | 0.9 |
| Charge Variant Analysis by CEX-UPLC | % Acidic | 35.9 | 35.3 | 35.6 | 35.1 | 33.4 | 34.5 |
| | % Main | 56.2 | 57.0 | 56.7 | 57.8 | 58.0 | 58.1 |
| | % Basic | 7.8 | 7.7 | 7.8 | 7.2 | 8.6 | 7.4 |
| Charge Variant Analysis by iCIEF | % Acidic | 33.8 | 33.1 | 32.7 | 34.4 | 34.5 | 33.2 |
| | % Main | 59.9 | 59.9 | 60.7 | 59.7 | 59.6 | 59.9 |
| | % Basic | 6.3 | 7.0 | 6.6 | 5.9 | 5.9 | 7.0 |
| % mAb1 Relative Potency by Bioassay | | 95 | NR | NR | 144 | NR | 99 |

TABLE 6

Research Stability of 10 mg/mL mAb1 Formulated Drug Substance Stored at −30° C.

| | |
|---|---|
| Formulation | 10 mg/mL mAb1, 10 mM sodium phosphate, 40 mM sodium chloride, 5% (w/v) sucrose, 0.03% (w/v) polysorbate 20, pH 6.2 |
| Fill Volume | 1.0 mL |
| Container/Closure | 5 mL polycarbonate vial with silicone lined polypropylene screw cap |

| | | Length of Storage (months) | | | | | |
|---|---|---|---|---|---|---|---|
| Assay | | 0 | 1 | 3 | 6 | 9 | 12 |
| Color and Appearance | | Pass | Pass | Pass | Pass | Pass | Pass |
| Turbidity (Increase in OD at 405 nm) | | 0.00 | 0.00 | 0.00 | 0.00 | 0.00 | 0.00 |
| pH | | 6.2 | 6.1 | 6.2 | 6.2 | 6.2 | 6.2 |
| % Total mAb1 Recovered by RP-HPLC | | 100 | 100 | 103 | 104 | 104 | 100 |
| Purity by SDS-PAGE | Non-reduced; % main peak | 95 | NR | NR | 96 | NR | 95 |
| | Reduced; % heavy + light chain | 100 | NR | NR | 100 | NR | 100 |
| Purity by SE-UPLC | % HMW | 2.3 | 2.4 | 2.3 | 2.4 | 2.3 | 2.3 |
| | % Native | 96.8 | 96.5 | 96.8 | 96.4 | 96.8 | 96.8 |
| | % LMW | 0.9 | 1.1 | 0.9 | 1.2 | 1.0 | 0.9 |
| Charge Variant Analysis by CEX-UPLC | % Acidic | 35.9 | 35.5 | 35.4 | 35.1 | 33.6 | 34.8 |
| | % Main | 56.2 | 56.8 | 56.9 | 57.9 | 58.5 | 58.0 |
| | % Basic | 7.8 | 7.8 | 7.7 | 7.1 | 8.0 | 7.2 |
| Charge Variant Analysis by iCIEF | % Acidic | 33.8 | 34.0 | 32.9 | 34.1 | 34.3 | 33.2 |
| | % Main | 59.9 | 60.0 | 61.2 | 60.2 | 59.1 | 60.3 |
| | % Basic | 6.3 | 6.0 | 5.9 | 5.7 | 6.5 | 6.5 |
| % mAb1 Relative Potency by Bioassay | | 95 | NR | NR | NR | NR | NR |

TABLE 7

Research Stability of 10 mg/mL mAb1 Formulated Drug Substance Stored at −20° C.

| | |
|---|---|
| Formulation | 10 mg/mL mAb1, 10 mM sodium phosphate, 40 mM sodium chloride, 5% (w/v) sucrose, 0.03% (w/v) polysorbate 20, pH 6.2 |
| Fill Volume | 1.0 mL |
| Container/Closure | 5 mL polycarbonate vial with silicone lined polypropylene screw cap |

| | | Length of Storage (months) | | | | | |
|---|---|---|---|---|---|---|---|
| Assay | | 0 | 1 | 3 | 6 | 9 | 12 |
| Color and Appearance | | Pass | Pass | Pass | Pass | Pass | Pass |
| Turbidity (Increase in OD at 405 nm) | | 0.00 | 0.00 | 0.00 | 0.00 | 0.00 | 0.00 |
| pH | | 6.2 | 6.2 | 6.2 | 6.2 | 6.3 | 6.2 |
| % Total mAb1 Recovered by RP-HPLC | | 100 | 104 | 103 | 106 | 105 | 100 |
| Purity by SDS-PAGE | Non-reduced; % main peak | 95 | NR | NR | 96 | NR | 95 |

TABLE 7-continued

Research Stability of 10 mg/mL mAb1 Formulated Drug Substance Stored at −20° C.

|  |  |  |  |  |  |  |  |
|---|---|---|---|---|---|---|---|
|  | Reduced; % heavy + light chain | 100 | NR | NR | 100 | NR | 99 |
| Purity by | % HMW | 2.3 | 2.1 | 2.0 | 1.9 | 1.8 | 1.9 |
| SE-UPLC | % Native | 96.8 | 96.7 | 96.8 | 96.8 | 97.3 | 97.3 |
|  | % LMW | 0.9 | 1.2 | 1.2 | 1.2 | 1.0 | 0.9 |
| Charge Variant | % Acidic | 35.9 | 35.4 | 35.5 | 34.9 | 33.5 | 34.3 |
| Analysis by | % Main | 56.2 | 56.8 | 56.9 | 57.9 | 58.7 | 58.1 |
| CEX-UPLC | % Basic | 7.8 | 7.7 | 7.6 | 7.3 | 7.9 | 7.6 |
| Charge Variant | % Acidic | 33.8 | 32.7 | 34.1 | 34.2 | 34.1 | 34.4 |
| Analysis by | % Main | 59.9 | 60.6 | 59.5 | 60.0 | 60.1 | 59.5 |
| iCIEF | % Basic | 6.3 | 6.4 | 6.3 | 5.8 | 5.7 | 6.2 |
| % mAb1 Relative Potency by Bioassay |  | 95 | NR | NR | 94 | NR | 85 |

TABLE 8

Research Stability of 120 mg/mL mAb1 Formulated Drug Substance Stored at −80° C.

| Formulation | 120 mg/mL mAb1, 10 mM sodium phosphate, 40 mM sodium chloride, 5% (w/v) sucrose, 0.03% (w/v) polysorbate 20, pH 6.2 |
|---|---|
| Fill Volume | 1.0 mL |
| Container/Closure | 5 mL polycarbonate vial with silicone lined polypropylene screw cap |

| Assay | | Length of Storage (months) | | | | | |
|---|---|---|---|---|---|---|---|
|  |  | 0 | 1 | 3 | 6 | 9 | 12 |
| Color and Appearance | | Pass | Pass | Pass | Pass | Pass | Pass |
| Turbidity (Increase in OD at 405 nm) | | 0.00 | 0.00 | 0.00 | 0.00 | 0.00 | 0.00 |
| pH | | 6.2 | 6.3 | 6.3 | 6.3 | 6.3 | 6.2 |
| % Total mAb1 Recovered by RP-HPLC | | 100 | 99 | 101 | 105 | 101 | 103 |
| Purity by | Non-reduced; % main peak | 96 | NR | NR | 96 | NR | 96 |
| SDS-PAGE | Reduced; % heavy + light chain | 100 | NR | NR | 100 | NR | 99 |
| Purity by | % HMW | 2.6 | 2.7 | 2.6 | 2.7 | 2.6 | 2.7 |
| SE-UPLC | % Native | 96.4 | 96.2 | 96.4 | 96.2 | 96.5 | 96.5 |
|  | % LMW | 1.0 | 1.1 | 1.0 | 1.2 | 0.9 | 0.8 |
| Charge Variant | % Acidic | 35.7 | 35.3 | 35.2 | 35.0 | 33.3 | 34.6 |
| Analysis by | % Main | 55.8 | 56.5 | 56.5 | 57.4 | 58.2 | 57.8 |
| CEX-UPLC | % Basic | 8.5 | 8.2 | 8.3 | 7.7 | 8.6 | 7.6 |
| Charge Variant | % Acidic | 33.6 | 33.9 | 32.8 | 34.2 | 32.7 | 33.9 |
| Analysis by | % Main | 59.9 | 59.9 | 60.8 | 59.2 | 60.7 | 59.8 |
| iCIEF | % Basic | 6.5 | 6.2 | 6.5 | 6.6 | 6.6 | 6.4 |
| % mAb1 Relative Potency by Bioassay | | 118 | NR | NR | 74 | NR | 89 |

TABLE 9

Research Stability of 120 mg/mL mAb1 Formulated Drug Substance Stored at −30° C.

| Formulation | 120 mg/mL mAb1, 10 mM sodium phosphate, 40 mM sodium chloride, 5% (w/v) sucrose, 0.03% (w/v) polysorbate 20, pH 6.2 |
|---|---|
| Fill Volume | 1.0 mL |
| Container/Closure | 5 mL polycarbonate vial with silicone lined polypropylene screw cap |

| Assay | | Length of Storage (months) | | | | | |
|---|---|---|---|---|---|---|---|
|  |  | 0 | 1 | 3 | 6 | 9 | 12 |
| Color and Appearance | | Pass | Pass | Pass | Pass | Pass | Pass |
| Turbidity (Increase in OD at 405 nm) | | 0.00 | 0.00 | 0.00 | 0.00 | 0.00 | 0.00 |
| pH | | 6.2 | 6.3 | 6.3 | 6.3 | 6.3 | 6.3 |
| % Total mAb1 Recovered by RP-HPLC | | 100 | 98 | 103 | 105 | 100 | 104 |
| Purity by | Non-reduced; % main peak | 96 | NR | NR | 96 | NR | 97 |
| SDS-PAGE | Reduced; % heavy + light chain | 100 | NR | NR | 100 | NR | 100 |

TABLE 9-continued

Research Stability of 120 mg/mL mAb1 Formulated Drug Substance Stored at −30° C.

| | | | | | | | |
|---|---|---|---|---|---|---|---|
| Purity by | % HMW | 2.6 | 2.6 | 2.6 | 2.6 | 2.6 | 2.6 |
| SE-UPLC | % Native | 96.4 | 96.2 | 96.3 | 96.2 | 96.6 | 96.6 |
| | % LMW | 1.0 | 1.2 | 1.1 | 1.1 | 0.9 | 0.8 |
| Charge Variant | % Acidic | 35.7 | 35.5 | 35.2 | 34.8 | 33.4 | 34.3 |
| Analysis by | % Main | 55.8 | 56.3 | 56.0 | 56.9 | 58.1 | 57.6 |
| CEX-UPLC | % Basic | 8.5 | 8.2 | 8.8 | 8.3 | 8.5 | 8.2 |
| Charge Variant | % Acidic | 33.6 | 32.9 | 33.4 | 33.4 | 34.1 | 32.4 |
| Analysis by | % Main | 59.9 | 60.4 | 60.1 | 60.8 | 59.6 | 61.1 |
| iCIEF | % Basic | 6.5 | 6.7 | 6.5 | 5.7 | 6.3 | 6.5 |
| % mAb1 Relative Potency by Bioassay | | 118 | NR | NR | NR | NR | NR |

TABLE 10

Research Stability of 120 mg/mL mAb1 Formulated Drug Substance Stored at −20° C.

| | |
|---|---|
| Formulation | 120 mg/mL mAb1, 10 mM sodium phosphate, 40 mM sodium chloride, 5% (w/v) sucrose, 0.03% (w/v) polysorbate 20, pH 6.2 |
| Fill Volume | 1.0 mL |
| Container/Closure | 5 mL polycarbonate vial with silicone lined polypropylene screw cap |

| | | Length of Storage (months) | | | | | |
|---|---|---|---|---|---|---|---|
| Assay | | 0 | 1 | 3 | 6 | 9 | 12 |
| Color and Appearance | | Pass | Pass | Pass | Pass | Pass | Pass |
| Turbidity (Increase in OD at 405 nm) | | 0.00 | 0.00 | 0.00 | 0.00 | 0.00 | 0.00 |
| pH | | 6.2 | 6.3 | 6.3 | 6.3 | 6.3 | 6.3 |
| % Total mAb1 Recovered by RP-HPLC | | 100 | 98 | 100 | 105 | 103 | 105 |
| Purity by | Non-reduced; % main peak | 96 | NR | NR | 96 | NR | 96 |
| SDS-PAGE | Reduced; % heavy + light chain | 100 | NR | NR | 100 | NR | 100 |
| Purity by | % HMW | 2.6 | 2.6 | 2.5 | 2.7 | 2.6 | 2.7 |
| SE-UPLC | % Native | 96.4 | 96.3 | 96.9 | 96.2 | 96.5 | 96.5 |
| | % LMW | 1.0 | 1.1 | 0.7 | 1.1 | 0.9 | 0.8 |
| Charge Variant | % Acidic | 35.7 | 35.4 | 35.2 | 34.7 | 33.1 | 34.2 |
| Analysis by | % Main | 55.8 | 56.2 | 56.5 | 57.2 | 58.2 | 57.5 |
| CEX-UPLC | % Basic | 8.5 | 8.4 | 8.4 | 8.1 | 8.7 | 8.3 |
| Charge Variant | % Acidic | 33.6 | 33.5 | 32.6 | 33.2 | 33.7 | 33.6 |
| Analysis by | % Main | 59.9 | 60.7 | 61.8 | 60.6 | 60.2 | 59.8 |
| iCIEF | % Basic | 6.5 | 5.8 | 5.6 | 6.2 | 6.1 | 6.5 |
| % mAb1 Relative Potency by Bioassay | | 118 | NR | NR | 80 | NR | 102 |

TABLE 11

Research Stability of 10 mg/mL mAb1 Formulated Drug Substance -Effect of Accelerated Conditions

| | |
|---|---|
| Formulation | 10 mg/mL mAb1, 10 mM sodium phosphate, 40 mM sodium chloride, 5% (w/v) sucrose, 0.03% (w/v) polysorbate 20, pH 6.2 |
| Fill Volume | 1.0 mL |
| Container/Closure | 5 mL polycarbonate vial w/silicone lined polypropylene screw cap |

| | | Storage Condition/Length of Storage (days) | | | | | | | | | |
|---|---|---|---|---|---|---|---|---|---|---|---|
| | | No Storage | 5° C. | | | 25° C./ 60% RH | | | 40° C./ 75% RH | | |
| Assay | | 0 | 14 | 28 | 56 | 7 | 14 | 28 | 7 | 14 | 28 |
| Color and Appearance | | Pass | Pass | Pass | Pass | Pass | Pass | Pass | Pass | Pass | Pass |
| Turbidity (Increase in OD at 405 nm) | | 0.00 | 0.00 | 0.00 | 0.00 | 0.00 | 0.00 | 0.00 | 0.00 | 0.00 | 0.00 |
| pH | | 6.2 | 6.2 | 6.2 | 6.2 | 6.2 | 6.2 | 6.2 | 6.2 | 6.2 | 6.1 |
| % Total mAb1 Recovered by RP-HPLC | | 100 | 105 | 103 | 105 | 104 | 106 | 109 | 104 | 109 | 121[1)] |
| Purity by | Non-reduced; % main peak | 95 | NR | NR | 95 | NR | NR | 91 | NR | NR | 84 |
| SDS-PAGE | Reduced; % heavy + light chain | 100 | NR | NR | 100 | NR | NR | 100 | NR | NR | 99 |

TABLE 11-continued

Research Stability of 10 mg/mL mAb1 Formulated Drug Substance -Effect of Accelerated Conditions

| | | | | | | | | | | | |
|---|---|---|---|---|---|---|---|---|---|---|---|
| Purity by | % HMW | 2.3 | 1.9 | 1.8 | 1.8 | 1.7 | 1.6 | 1.7 | 1.7 | 1.7 | 2.2 |
| SE-UPLC | % Native | 96.8 | 97.2 | 97.2 | 97.3 | 97.3 | 97.3 | 97.1 | 97.1 | 96.8 | 95.6 |
| | % LMW | 0.9 | 0.9 | 1.0 | 0.9 | 1.0 | 1.0 | 1.2 | 1.2 | 1.5 | 2.2 |
| Charge Variant | % Acidic | 35.9 | 35.9 | 35.9 | 35.4 | 36.1 | 37.0 | 38.6 | 41.0 | 46.9 | 56.0 |
| Analysis by | % Main | 56.2 | 56.5 | 56.9 | 57.1 | 55.9 | 55.4 | 54.0 | 50.8 | 46.1 | 37.4 |
| CEX-UPLC | % Basic | 7.8 | 7.7 | 7.2 | 7.5 | 8.0 | 7.6 | 7.5 | 8.2 | 7.0 | 6.6 |
| Charge | % Acidic | 33.8 | 33.9 | 33.0 | 33.9 | 33.7 | 35.3 | 37.0 | 40.1 | 45.7 | 55.1 |
| Variant | % Main | 59.9 | 59.6 | 60.7 | 59.5 | 59.6 | 57.8 | 55.6 | 52.5 | 46.3 | 37.2 |
| Analysis by iCIEF | % Basic | 6.3 | 6.4 | 6.3 | 6.6 | 6.7 | 6.9 | 7.3 | 7.4 | 8.1 | 7.7 |
| % mAb1 Relative Potency by Bioassay | | 95 | NR | NR | 101 | NR | NR | 90 | NR | NR | 136 |

TABLE 12

Research Stability of 120 mg/mL mAb1 Formulated Drug Substance - Effect of Accelerated Conditions

| | |
|---|---|
| Formulation | 120 mg/mL mAb1, 10 mM sodium phosphate, 40 mM sodium chloride, 5% (w/v) sucrose, 0.03% (w/v) polysorbate 20, pH 6.2 |
| Fill Volume | 1.0 mL |
| Container/Closure | 5 mL polycarbonate vial w/silicone lined polypropylene screw cap |

| | | Storage Condition/Length of Storage (days) | | | | | | | | |
|---|---|---|---|---|---|---|---|---|---|---|
| | | No Storage | 5° C. | | | 25° C./ 60% RH | | | 40° C./ 75% RH | | |
| Assay | | 0 | 14 | 28 | 56 | 7 | 14 | 28 | 7 | 14 | 28 |
| Color and Appearance | | Pass | Pass | Pass | Pass | Pass | Pass | Pass | Pass | Pass | Pass |
| Turbidity (Increase in OD at 405 nm) | | 0.00 | 0.00 | 0.00 | 0.00 | 0.00 | 0.00 | 0.00 | 0.00 | 0.00 | 0.00 |
| pH | | 6.2 | 6.3 | 6.3 | 6.2 | 6.3 | 6.3 | 6.2 | 6.3 | 6.3 | 6.2 |
| % Total mAb1 Recovered by RP-HPLC | | 100 | 102 | 101 | 102 | 102 | 104 | 104 | 104 | 105 | 107 |
| Purity by SDS-PAGE | Non-reduced; % main peak | 96 | NR | NR | 96 | NR | NR | 92 | NR | NR | 88 |
| | Reduced; % heavy + light chain | 100 | NR | NR | 100 | NR | NR | 100 | NR | NR | 100 |
| Purity by | % HMW | 2.6 | 2.6 | 2.5 | 2.7 | 2.7 | 2.9 | 3.0 | 3.8 | 4.9 | 6.5 |
| SE-UPLC | % Native | 96.4 | 96.5 | 96.5 | 96.4 | 96.5 | 96.3 | 95.9 | 95.0 | 93.5 | 91.5 |
| | % LMW | 1.0 | 0.9 | 0.9 | 0.9 | 0.8 | 0.9 | 1.1 | 1.2 | 1.7 | 1.9 |
| Charge Variant | % Acidic | 35.7 | 35.3 | 35.6 | 34.8 | 35.9 | 36.1 | 37.5 | 39.7 | 44.9 | 53.3 |
| Analysis by | % Main | 55.8 | 56.2 | 56.2 | 56.6 | 55.4 | 55.0 | 53.0 | 50.6 | 46.2 | 37.8 |
| CEX-UPLC | % Basic | 8.5 | 8.5 | 8.2 | 8.5 | 8.7 | 8.9 | 9.5 | 9.7 | 9.0 | 8.9 |
| Charge Variant | % Acidic | 33.6 | 34.4 | 32.3 | 34.2 | 33.2 | 34.2 | 36.1 | 38.4 | 44.8 | 54.2 |
| Analysis by | % Main | 59.9 | 60.0 | 61.5 | 59.5 | 60.3 | 58.9 | 56.7 | 53.9 | 46.6 | 37.4 |
| iCIEF | % Basic | 6.5 | 5.5 | 6.1 | 6.3 | 6.5 | 6.9 | 7.2 | 7.8 | 8.6 | 8.4 |
| % mAb1 Relative Potency by Bioassay | | 118 | NR | NR | 94 | NR | NR | 96 | NR | NR | 123 |

TABLE 13

Research Stability of 10 mg/mL mAb1 Formulated Drug Substance -Effect of Stress Conditions

| | |
|---|---|
| Formulation | 10 mg/mL mAb1, 10 mM sodium phosphate, 40 mM sodium chloride, 5% (w/v) sucrose, 0.03% (w/v) polysorbate 20, pH 6.2 |
| Fill Volume | 1.0 mL |
| Container/Closure | 5 mL polycarbonate vial with silicone lined polypropylene screw cap |

| | Stress Condition/Length of Stress | | | | |
|---|---|---|---|---|---|
| | No Stress | Agitation (minutes) | | Freeze/Thaw (Cycles) | |
| Assay | 0 | 60 | 120 | 4 | 8 |
| Color and Appearance | Pass | Pass | Pass | Pass | Pass |
| Turbidity (Increase in OD at 405 nm) | 0.00 | 0.00 | 0.00 | 0.00 | 0.00 |
| pH | 6.2 | 6.3 | 6.3 | 6.2 | 6.2 |
| % Total mAb1 Recovered by RP-HPLC | 100 | 96 | 97 | 103 | 105 |

TABLE 13-continued

Research Stability of 10 mg/mL mAb1 Formulated Drug Substance - Effect of Stress Conditions

| | | | | | | |
|---|---|---|---|---|---|---|
| Purity by SDS-PAGE | Non-reduced; % main peak | 95 | NR | 95 | NR | 95 |
| | Reduced; % heavy + light chain | 100 | NR | 100 | NR | 100 |
| Purity by SE-UPLC | % HMW | 2.3 | 2.0 | 2.0 | 2.4 | 2.3 |
| | % Native | 96.8 | 97.1 | 97.3 | 96.7 | 96.7 |
| | % LMW | 0.9 | 0.9 | 0.8 | 0.9 | 0.9 |
| Charge Variant Analysis by CEX-UPLC | % Acidic | 35.9 | 35.7 | 35.6 | 35.5 | 35.6 |
| | % Main | 56.2 | 56.2 | 55.9 | 56.2 | 56.3 |
| | % Basic | 7.8 | 8.1 | 8.5 | 8.4 | 8.1 |
| Charge Variant Analysis by iCIEF | % Acidic | 33.8 | 34.0 | 33.9 | 34.1 | 34.2 |
| | % Main | 59.9 | 59.5 | 60.4 | 59.8 | 59.6 |
| | % Basic | 6.3 | 6.5 | 5.7 | 6.1 | 6.3 |
| % mAb1 Relative Potency by Bioassay | | 95 | NR | 103 | NR | 107 |

TABLE 14

Research Stability of 120 mg/mL mAb1 Formulated Drug Substance - Effect of Stress Conditions

| | |
|---|---|
| Formulation | 120 mg/mL mAb1, 10 mM sodium phosphate, 40 mM sodium chloride, 5% (w/v) sucrose, 0.03% (w/v) polysorbate 20, pH 6.2 |
| Fill Volume | 1.0 mL |
| Container/Closure | 5 mL polycarbonate vial with silicone lined polypropylene screw cap |

| | | Stress Condition/Length of Stress | | | | |
|---|---|---|---|---|---|---|
| | | No Stress | Agitation (minutes) | | Freeze/Thaw (Cycles) | |
| Assay | | 0 | 60 | 120 | 4 | 8 |
| Color and Appearance | | Pass | Pass | Pass | Pass | Pass |
| Turbidity (Increase in OD at 405 nm) | | 0.00 | 0.00 | 0.00 | 0.00 | 0.00 |
| pH | | 6.2 | 6.3 | 6.3 | 6.3 | 6.3 |
| % Total mAb1 Recovered by RP-HPLC | | 100 | 94 | 95 | 100 | 100 |
| Purity by SDS-PAGE | Non-reduced; % main peak | 96 | NR | 96 | NR | 95 |
| | Reduced; % heavy + light chain | 100 | NR | 100 | NR | 100 |
| Purity by SE-UPLC | % HMW | 2.6 | 2.7 | 2.8 | 2.8 | 3.0 |
| | % Native | 96.4 | 96.4 | 96.4 | 96.3 | 96.2 |
| | % LMW | 1.0 | 0.9 | 0.9 | 0.9 | 0.8 |
| Charge Variant Analysis by CEX-UPLC | % Acidic | 35.7 | 35.8 | 35.8 | 35.8 | 35.7 |
| | % Main | 55.8 | 55.9 | 56.2 | 56.1 | 55.8 |
| | % Basic | 8.5 | 8.4 | 8.0 | 8.1 | 8.4 |
| Charge Variant Analysis by iCIEF | % Acidic | 33.6 | 33.2 | 33.2 | 33.9 | 33.7 |
| | % Main | 59.9 | 60.4 | 60.3 | 59.5 | 60.1 |
| | % Basic | 6.5 | 6.4 | 6.5 | 6.6 | 6.2 |
| % mAb1 Relative Potency by Bioassay | | 118 | NR | 120 | NR | 98 |

Research stability studies for the mAb1 drug products were conducted as shown in Tables 15 and 16:

TABLE 15

Research Stability Studies for mAb1 Drug Products

| Storage Stability[1] | | Container/Closure |
|---|---|---|
| Storage Temperature | Length of Storage (months) | Type 1 borosilicate glass with FluroTec ® coated 4432/50 butyl rubber stopper |
| 5° C. | 0, 1, 3, 6, 9, 12, 18, 24, and 36 | |
| Accelerated Stability[2] | | |
| Incubation Condition | Length of Incubation | |
| 25° C. | 0, 1, 3, and 6 months | |
| 37° C. | 0, 7, 14, and 28 days | |
| Stress Stability | | |
| Stress | Duration of Stress | |
| Agitation (vortex) | 0, 60, and 120 minutes | |
| Freeze/Thaw[3] | 0, 4, and 8 cycles | |

TABLE 16

Research Stability Study Analysis Plan for mAb1 Drug Products

| Assay | Samples to be Analyzed |
|---|---|
| Color and Appearance | All Samples |
| pH | All Samples |
| Turbidity (Increase in OD at 405 nm) | All Samples |
| % mAb1 Recovered by RP-HPLC | All Samples |
| % mAb1 Purity by Non-Reduced and Reduced SDS-PAGE | t = 0, 6, 12, 24 and 36 months at 5° C.; 6 months at 25° C.; 28 days at 37° C. 120 min Agitation, 8X Freeze/Thaw |
| % Purity by SE-UPLC | All Samples |
| Charge Variant Analysis by CEX-UPLC | All Samples |

TABLE 16-continued

Research Stability Study Analysis Plan for mAb1 Drug Products

| Assay | Samples to be Analyzed |
|---|---|
| Charge Variant Analysis by iCIEF | All Samples |
| Particulate Matter Analysis by MFI | t = 0, 6, 12, 24 and 36 months at 5° C.; 6 months at 25° C.; 28 days at 37° C. 120 min Agitation, 8X Freeze/Thaw |
| % mAb1 Relative Potency by Bioassay | t = 0, 6, 12, 24 and 36 months at 5° C.; 6 months at 25° C.; 28 days at 37° C. 120 min Agitation, 8X Freeze/Thaw |

The results of stability studies for the drug products are summarized in Tables 17-22:

TABLE 17

Research Stability of 10 mg/mL mAb1 Drug Product Stored at 5° C.

| | |
|---|---|
| Formulation | 10 mg/mL mAb1, 10 mM sodium phosphate, 40 mM sodium chloride, 5% (w/v) sucrose, 0.03% (w/v) polysorbate 20, pH 6.2 |
| Fill Volume | 0.5 mL |
| Container/Closure | 2 mL Type I borosilicate glass vial with West S2-F451 4432/50 GRY B2-40 stopper |

| Assay | | Length of Storage (months) | | | | |
|---|---|---|---|---|---|---|
| | | 0 | 1 | 3 | 6 | 9 |
| Color and Appearance | | Pass | Pass | Pass | Pass | Pass |
| Turbidity (Increase in OD at 405 nm) | | 0.00 | 0.00 | 0.00 | 0.00 | 0.00 |
| pH | | 6.3 | 6.3 | 6.2 | 6.2 | 6.3 |
| % mAb1 Recovered by RP-HPLC | | 100 | 102 | 99 | 97 | 98 |
| Purity by SDS-PAGE | Non-reduced; % main peak | 95 | NR | NR | 94 | NR |
| | Reduced; % heavy + light chain | 100 | NR | NR | 100 | NR |
| Purity by SE-UPLC | % HMW | 1.4 | 1.4 | 1.3 | 1.3 | 1.2 |
| | % Native | 97.7 | 97.6 | 97.6 | 97.5 | 97.8 |
| | % LMW | 1.0 | 1.1 | 1.1 | 1.1 | 1.0 |
| Charge Variant Analysis by CEX-UPLC | % Acidic | 39.3 | 39.1 | 37.5 | 37.3 | 38.5 |
| | % Main | 54.6 | 55.2 | 55.9 | 56.4 | 55.9 |
| | % Basic | 6.2 | 5.7 | 6.7 | 6.3 | 5.7 |
| Charge Variant Analysis by iCIEF | % Acidic | 37.6 | 38.3 | 37.5 | 38.4 | 37.3 |
| | % Main | 57.7 | 57.0 | 58.3 | 57.4 | 58.0 |
| | % Basic | 4.7 | 4.7 | 4.2 | 4.2 | 4.7 |
| Particulate Analysis by MFI (particles/mL) | ≥2 μm | 6790 | NR | NR | 6905 | NR |
| | ≥10 μm | 255 | NR | NR | 266 | NR |
| | ≥25 μm | 44 | NR | NR | 26 | NR |
| % mAb1 Relative Potency by Bioassay | | 94 | NR | NR | 114 | NR |

TABLE 18

Research Stability of 120 mg/mL mAb1 Drug Product Stored at 5° C.

| | |
|---|---|
| Formulation | 120 mg/mL mAb1, 10 mM sodium phosphate, 40 mM sodium chloride, 5% (w/v) sucrose, 0.03% (w/v) polysorbate 20, pH 6.2 |
| Fill Volume | 0.5 mL |
| Container/Closure | 2 mL Type I borosilicate glass vial with West S2-F451 4432/50 GRY B2-40 stopper |

| Assay | | Length of Storage (months) | | | | |
|---|---|---|---|---|---|---|
| | | 0 | 1 | 3 | 6 | 9 |
| Color and Appearance | | Pass | Pass | Pass | Pass | Pass |
| Turbidity (Increase in OD at 405 nm) | | 0.00 | 0.00 | 0.00 | 0.00 | 0.00 |
| pH | | 6.3 | 6.3 | 6.3 | 6.3 | 6.3 |
| % mAb1 Recovered by RP-HPLC | | 100 | 98 | 97 | 101 | 99 |
| Purity by SDS-PAGE | Non-reduced; % main peak | 95 | NR | NR | 94 | NR |
| | Reduced; % heavy + light chain | 100 | NR | NR | 100 | NR |
| Purity by SE-UPLC | % HMW | 2.6 | 2.7 | 2.8 | 3.1 | 3.0 |
| | % Native | 96.5 | 96.5 | 96.3 | 96.0 | 96.2 |
| | % LMW | 0.9 | 0.8 | 0.9 | 0.9 | 0.9 |

TABLE 18-continued

Research Stability of 120 mg/mL mAb1 Drug Product Stored at 5° C.

| Charge Variant | % Acidic | 38.8 | 38.7 | 36.7 | 36.4 | 38.3 |
|---|---|---|---|---|---|---|
| Analysis by | % Main | 54.3 | 54.3 | 55.9 | 55.4 | 56.0 |
| CEX-UPLC | % Basic | 6.9 | 7.0 | 7.4 | 8.2 | 5.7 |
| Charge Variant | % Acidic | 37.7 | 37.7 | 38.0 | 37.7 | 37.7 |
| Analysis by | % Main | 58.0 | 57.9 | 57.5 | 57.6 | 57.6 |
| iCIEF | % Basic | 4.3 | 4.4 | 4.5 | 4.7 | 4.7 |
| Particulate | ≥2 μm | 1995 | NR | NR | 12705 | NR |
| Analysis by MFI | ≥10 μm | 111 | NR | NR | 282 | NR |
| (particles/mL) | ≥25 μm | 13 | NR | NR | 9 | NR |
| % mAb1 Relative Potency by Bioassay | | 107 | NR | NR | 150 | NR |

TABLE 19

Research Stability of 10 mg/mL mAb1 Drug Product - Effect of Accelerated Conditions

| Formulation | 10 mg/mL mAb1, 10 mM sodium phosphate, 40 mM sodium chloride, 5% (w/v) sucrose, 0.03% (w/v) polysorbate 20, pH 6.2 |
|---|---|
| Fill Volume | 0.5 mL |
| Container/Closure | 2 mL Type I borosilicate glass vial with West S2-F451 4432/50 GRY B2-40 stopper |

| | | No Storage | 25° C. (months) | | | 37° C. (days) | | |
|---|---|---|---|---|---|---|---|---|
| Assay | | 0 | 1 | 3 | 6 | 7 | 14 | 28 |
| Color and Appearance | | Pass | Pass | Pass | Pass | Pass | Pass | Pass |
| Turbidity (Increase in OD at 405 nm) | | 0.00 | 0.00 | 0.00 | 0.00 | 0.00 | 0.00 | 0.00 |
| pH | | 6.3 | 6.2 | 6.2 | 6.2 | 6.3 | 6.3 | 6.3 |
| % mAb1 Recovered by RP-HPLC | | 100 | 105 | 99 | 98 | 100 | 105 | 98 |
| Purity by SDS-PAGE | Non-reduced; % main peak | 95 | NR | NR | 89 | NR | NR | 86 |
| | Reduced; % heavy + light chain | 100 | NR | NR | 100 | NR | NR | 96 |
| Purity by SE-UPLC | % HMW | 1.4 | 1.3 | 1.4 | 1.3 | 1.2 | 1.3 | 1.3 |
| | % Native | 97.7 | 97.4 | 96.8 | 96.5 | 97.1 | 97.0 | 96.2 |
| | % LMW | 1.0 | 1.3 | 1.8 | 2.2 | 1.7 | 1.7 | 2.6 |
| Charge Variant | % Acidic | 39.3 | 41.4 | 48.1 | 53.9 | 41.9 | 45.3 | 52.1 |
| Analysis by | % Main | 54.6 | 52.5 | 46.1 | 40.6 | 52.0 | 48.6 | 42.1 |
| CEX-UPLC | % Basic | 6.2 | 6.1 | 5.8 | 5.5 | 6.1 | 6.1 | 5.8 |
| Charge Variant | % Acidic | 37.6 | 40.7 | 47.3 | 54.7 | 40.1 | 44.2 | 51.7 |
| Analysis by | % Main | 57.7 | 53.4 | 47.5 | 39.2 | 54.7 | 50.2 | 41.8 |
| iCIEF | % Basic | 4.7 | 5.8 | 5.2 | 6.1 | 5.2 | 5.6 | 6.5 |
| Particulate | ≥2 μm | 6790 | NR | NR | 8385 | NR | NR | 3697 |
| Analysis by MFI | ≥10 μm | 255 | NR | NR | 280 | NR | NR | 153 |
| (particles/mL) | ≥25 μm | 44 | NR | NR | 23 | NR | NR | 21 |
| % Relative Potency by Bioassay | | 94 | NR | NR | 149 | NR | NR | 95 |

TABLE 20

Research Stability of 120 mg/mL mAb1 Drug Product - Effect of Accelerated Conditions

| Formulation | 120 mg/mL mAb1, 10 mM sodium phosphate, 40 mM sodium chloride, 5% (w/v) sucrose, 0.03% (w/v) polysorbate 20, pH 6.2 |
|---|---|
| Fill Volume | 0.5 mL |
| Container/Closure | 2 mL Type I borosilicate glass vial with West S2-F451 4432/50 GRY B2-40 stopper |

| | No Storage | 25° C. (months) | | | 37° C. (days) | | |
|---|---|---|---|---|---|---|---|
| Assay | 0 | 1 | 3 | 6 | 7 | 14 | 28 |
| Color and Appearance | Pass | Pass | Pass | Pass | Pass | Pass | Pass |
| Turbidity (Increase in OD at 405) | 0.00 | 0.00 | 0.00 | 0.01 | 0.00 | 0.00 | 0.00 |
| pH | 6.3 | 6.3 | 6.3 | 6.3 | 6.3 | 6.3 | 6.3 |
| % mAb1 Recovered by RP-HPLC | 100 | 98 | 96 | 100 | 96 | 104 | 95 |

TABLE 20-continued

Research Stability of 120 mg/mL mAb1 Drug Product - Effect of Accelerated Conditions

| | | | | | | | | |
|---|---|---|---|---|---|---|---|---|
| Purity by SDS-PAGE | Non-reduced; % main peak | 95 | NR | NR | 88 | NR | NR | 89 |
| | Reduced; % heavy + light chain | 100 | NR | NR | 100 | NR | NR | 100 |
| Purity by SE-UPLC | % HMW | 2.6 | 3.0 | 3.2 | 4.2 | 3.3 | 3.5 | 3.8 |
| | % Native | 96.5 | 95.2 | 95.2 | 93.6 | 95.1 | 95.2 | 94.1 |
| | % LMW | 0.9 | 1.9 | 1.6 | 2.2 | 1.7 | 1.3 | 2.1 |
| Charge Variant Analysis by CEX-UPLC | % Acidic | 38.8 | 40.5 | 44.3 | 51.8 | 40.7 | 44.0 | 50.6 |
| | % Main | 54.3 | 51.9 | 47.1 | 40.8 | 51.2 | 48.0 | 41.5 |
| | % Basic | 6.9 | 7.6 | 8.6 | 7.4 | 8.1 | 8.0 | 7.9 |
| Charge Variant Analysis by iCIEF | % Acidic | 37.7 | 39.9 | 46.9 | 54.4 | 40.5 | 44.6 | 50.8 |
| | % Main | 58.0 | 55.0 | 47.1 | 39.4 | 54.6 | 49.2 | 42.5 |
| | % Basic | 4.3 | 5.1 | 6.0 | 6.2 | 4.9 | 6.2 | 6.7 |
| Particulate Analysis by MFI (particles/mL) | ≥2 μm | 1995 | NR | NR | 7414 | NR | NR | 7027 |
| | ≥10 μm | 111 | NR | NR | 179 | NR | NR | 193 |
| | ≥25 μm | 13 | NR | NR | 13 | NR | NR | 5 |
| % Relative Potency by Bioassay | | 107 | NR | NR | 120 | NR | NR | 145 |

TABLE 21

Research Stability of mAb1 (10 mg/mL) Drug Product - Effect of Stress Conditions

| | |
|---|---|
| Formulation | 10 mg/mL mAb1, 10 mM sodium phosphate, 40 mM sodium chloride, 5% (w/v) sucrose, 0.03% (w/v) polysorbate 20, pH 6.2 |
| Fill Volume | 0.5 mL |
| Container/Closure | 2 mL Type I borosilicate glass vial with West S2-F451 4432/50 GRY B2-40 stopper |

| | | Stress Condition/Length of Stress | | | | |
|---|---|---|---|---|---|---|
| | | No Stress | Agitation (minutes) | | Freeze/Thaw (Cycles) | |
| Assay | | 0 | 60 | 120 | 4 | 8 |
| Color and Appearance | | Pass | Pass | Pass | Pass | Pass |
| Turbidity (Increase in OD at 405 nm) | | 0.00 | 0.00 | 0.00 | 0.00 | 0.00 |
| pH | | 6.3 | 6.3 | 6.3 | 6.3 | 6.3 |
| % mAb1 Recovered by RP-HPLC | | 100 | 103 | 103 | 98 | 99 |
| Purity by SDS-PAGE | Non-reduced; % main peak | 95 | NR | 95 | NR | 95 |
| | Reduced; % heavy + light chain | 100 | NR | 100 | NR | 100 |
| Purity by SE-UPLC | % Total HMW | 1.4 | 1.5 | 1.4 | 1.5 | 1.6 |
| | % Total Native | 97.7 | 97.5 | 97.6 | 97.7 | 97.4 |
| | % Total LMW | 1.0 | 1.0 | 1.1 | 0.8 | 1.1 |
| Charge Variant Analysis by CEX-UPLC | % Acidic | 39.3 | 39.1 | 39.1 | 39.2 | 39.3 |
| | % Main | 54.6 | 54.7 | 54.6 | 54.9 | 54.5 |
| | % Basic | 6.2 | 6.2 | 6.2 | 5.9 | 6.2 |
| Charge Variant Analysis by iCIEF | % Acidic | 37.6 | 37.3 | 37.1 | 38.2 | 38.6 |
| | % Main | 57.7 | 58.8 | 58.9 | 57.2 | 56.4 |
| | % Basic | 4.7 | 3.8 | 4.0 | 4.6 | 5.0 |
| Particulate Analysis by MFI (particles/mL) | ≥2 μm | 6790 | NR | 6089 | NR | 16535 |
| | ≥10 μm | 255 | NR | 284 | NR | 236 |
| | ≥25 μm | 44 | NR | 36 | NR | 42 |
| % Relative Potency by Bioassay | | 94 | NR | 110 | NR | 73 |

TABLE 22

Research Stability of mAb1 (120 mg/mL) Drug Product - Effect of Stress Conditions

| | |
|---|---|
| Formulation | 120 mg/mL mAb1, 10 mM sodium phosphate, 40 mM sodium chloride, 5% (w/v) sucrose, 0.03% (w/v) polysorbate 20, pH 6.2 |
| Fill Volume | 0.5 mL |
| Container/Closure | 2 mL Type I borosilicate glass vial with West S2-F451 4432/50 GRY B2-40 stopper |

TABLE 22-continued

Research Stability of mAb1 (120 mg/mL) Drug Product - Effect of Stress Conditions

| Assay | | No Stress | Agitation (minutes) | | Freeze/Thaw (Cycles) | |
|---|---|---|---|---|---|---|
| | | 0 | 60 | 120 | 4 | 8 |
| Color and Appearance | | Pass | Pass | Pass | Pass | Pass |
| Turbidity (Increase in OD at 405 nm) | | 0.00 | 0.00 | 0.00 | 0.00 | 0.00 |
| pH | | 6.3 | 6.3 | 6.3 | 6.3 | 6.3 |
| % mAb1 Recovered by RP-HPLC | | 100 | 99 | 99 | 96 | 96 |
| Purity by SDS-PAGE | Non-reduced; % main peak | 95 | NR | 94 | NR | 93 |
| | Reduced; % heavy + light chain | 100 | NR | 100 | NR | 100 |
| Purity by SE-UPLC | % Total HMW | 2.6 | 2.6 | 2.6 | 3.0 | 3.0 |
| | % Total Native | 96.5 | 96.3 | 96.3 | 96.2 | 96.2 |
| | % Total LMW | 0.9 | 1.2 | 1.2 | 0.8 | 0.8 |
| Charge Variant Analysis by CEX-UPLC | % Acidic | 38.8 | 39.0 | 38.8 | 39.2 | 39.1 |
| | % Main | 54.3 | 54.5 | 54.6 | 53.6 | 53.8 |
| | % Basic | 6.9 | 6.5 | 6.6 | 7.3 | 7.2 |
| Charge Variant Analysis by iCIEF | % Acidic | 37.7 | 37.4 | 37.2 | 36.8 | 37.8 |
| | % Main | 58.0 | 58.5 | 58.2 | 58.5 | 57.4 |
| | % Basic | 4.3 | 4.1 | 4.5 | 4.7 | 4.8 |
| Particulate Analysis by MFI (particles/mL) | ≥2 μm | 108 | NR | 891 | NR | 6365 |
| | ≥10 μm | 11 | NR | 93 | NR | 175 |
| | ≥25 μm | 0 | NR | 30 | NR | 19 |
| % Relative Potency by Bioassay | | 107 | NR | 125 | NR | 111 |

The results of the stability studies indicated that:

Formulated drug substance (FDS) 10 mg/mL mAb1 is stable when stored at ≤−20° C. for at least 12 months FDS 120 mg/mL mAb1 is stable when stored at ≤−20° C. for at least 12 months FDS 10 mg/mL mAb1 was physically and chemically stable after 56 days of incubation at 5° C. and maintained potency when incubated at 5° C. for 56 days or at 25° C./60% relative humidity (RH) and at 40° C./75% RH for 28 days.

FDS 120 mg/mL mAb1 was physically and chemically stable after 56 days of incubation at 5° C. and maintained potency when incubated at 5° C. for 56 days or at 25° C./60% relative humidity (RH) and at 40° C./75% RH for 28 days.

10 mg/mL mAb1 FDS was physically and chemically stable when agitated (vortexed at ambient temperature) for 120 minutes or when subjected to 8 freeze/thaw cycles (freezing at −30° C. and thawing at room temperature). No appreciable change in the physical or chemical stability was detected in any of the monitored attributes. mAb1 maintained potency when the 10 mg/mL mAb1 FDS was agitated (vortexed at ambient temperature) for 120 minutes or when subjected to 8 freeze/thaw cycles (freezing at −30° C. and thawing at room temperature).

120 mg/mL mAb1 FDS was physically and chemically stable when agitated (vortexed at ambient temperature) for 120 minutes or when subjected to 8 freeze/thaw cycles (freezing at −30° C. and thawing at room temperature). No appreciable change in the physical or chemical stability was detected in any of the monitored attributes. mAb1 maintained potency when the 120 mg/mL mAb1 FDS was agitated (vortexed at ambient temperature) for 120 minutes or when subjected to 8 freeze/thaw cycles (freezing at −30° C. and thawing at room temperature).

Drug product (DP) 10 mg/mL mAb1 is stable when stored at 2-8° C. for at least 9 months DP 120 mg/mL mAb1 is stable when stored at 2-8° C. for at least 9 months.

Example 7: Co-Formulation Comprising an Anti-Ang-2 Antibody and a VEGF Antagonist Co-formulation development activities included the screening of buffers, organic co-solvents, and thermal stabilizers in liquid formulations of VEGF antagonist and anti-Ang-2 antibody to identify excipients that enhance the stability of the protein. Buffer conditions were also examined to determine the optimal pH for maximum protein stability. Results generated from these studies were used to develop a stable, liquid co-formulation suitable for clinical use. The VEGF antagonist consists of a dimer of two polypeptides consisting of amino acids 27-457 of SEQ ID NO: 11 (also referred to herein as aflibercept). The anti-Ang-2 antibody is the human anti-Ang-2 antibody with HCVR/LCVR of SEQ ID NOs: 1/2 and designated as H1H685 in US Patent Application Publication US20110027286 (also referred to herein as "mAb1"). The VEGF antagonist was co-formulated with anti-Ang-2 antibody at four concentrations:

(i) 40 mg/mL±6.0 mg/mL aflibercept with 10 mg/mL±1.5 mg/mL mAb1, (ii) 40 mg/mL±6.0 mg/mL aflibercept with 20 mg/mL±3.0 mg/mL mAb1, (iii) 40 mg/mL±6.0 mg/mL aflibercept with 60 mg/mL±9.0 mg/mL mAb1, and (iv) 40 mg/mL±6.0 mg/mL aflibercept with 120 mg/mL±18.0 mg/mL mAb1.

In various embodiments, the anti-Ang-2 antibody and VEGF antagonist are co-formulated in 10±1.5 mM sodium phosphate (pH 6.2±0.3), 0.03%±0.0045% polysorbate 20, 40 mM±6.0 mM sodium chloride, and 5%±0.75% sucrose, in water.

The stability of the formulated drug substance and drug product was assessed using assays as described in Example 8 herein. Charge variant analysis was done using imaged capillary isoelectric focusing (iCIEF) for the formulated drug substance and drug product.

Stability studies were initiated to determine the storage, accelerated (temperatures above storage conditions), and stress (agitation and freezing and thawing) stability of research lots of 10 mg/mL:40 mg/mL and 120 mg/mL:40 mg/mL (mAb1:aflibercept) FDS. These conditions were chosen to bracket the protein concentrations of FDS that used to manufacture the clinical DP. Evaluation of research lots of FDS under accelerated and stress conditions was performed by subjecting FDS to a variety of tests designed to exceed stresses the FDS may encounter during the manufacture of DP and to elucidate the degradation pathways for mAb1:aflibercept FDS. FDS was filled in 5 mL polycarbonate vials.

The research stability for the co-formulated drug substance was studied as shown in Tables 23 and 24:

TABLE 23

Research Stability Study for mAb1:aflibercept Formulated Drug Substance

| Storage Stability[1] | | Container/Closure |
|---|---|---|
| Storage Temperature | Length of Storage (months) | 5 mL Nalge-Nunc polycarbonate vial with lined closure |
| −80° C. | 0, 1, 3, 6, 9, 12, 18, 24, and 36 | |
| −30° C. | 0, 1, 3, 6, 9, 12, 18, 24, and 36 | |
| −20° C. | 0, 1, 3, 6, 9, 12, 18, 24, and 36 | |
| Accelerated Stability[2] | | |
| Incubation Condition | Length of Incubation | |
| 5° C. | 0, 14, 28, and 56 days | |
| 25° C./60% RH | 0, 7, 14, and 28 days | |
| 40° C./75% RH | 0, 7, 14, and 28 days | |
| Stress Stability | | |
| Stress | Duration of Stress | |
| Agitation (vortex) | 0, 60, and 120 minutes | |
| Freeze/Thaw[3] | 0, 4, and 8 cycles | |

TABLE 24

Analysis Plan for mAb1:aflibercept Formulated Drug Substance Research Stability Study

| Assay | Samples to be Analyzed |
|---|---|
| Color and Appearance | All Samples |
| pH | All Samples |
| Turbidity (Increase in OD at 405 nm) | All Samples |
| % mAb1 Recovered by RP-HPLC | All Samples |
| % Aflibercept Recovered by RP-HPLC | All Samples |
| Total Purity (mAb1 + aflibercept) by Non-Reduced and Reduced SDS-PAGE | t = 0, 6, 12, 24 and 36 months at −80° C., −30° C., and −20° C. 56 days at 5° C., 28 days at 25° C./60% RH and 40° C./75% RH ° C. 120 min Agitation, 8X Freeze/Thaw |
| Total (mAb1 + aflibercept) Purity by SE-UPLC | All Samples |
| REGN910 Charge Variant Analysis by iCIEF | All Samples |
| Aflibercept Charge Variant Analysis by iCIEF | All Samples |
| % mAb1 Relative Potency by Bioassay | t = 0, 6, 12, 24 and 36 months at −80° C. and −20° C. 56 days at 5° C., 28 days at 25° C./60% RH and 40° C./75% RH ° C. 120 min Agitation, 8X Freeze/Thaw |
| % Aflibercept Relative Potency by Bioassay | t = 0, 6, 12, 24 and 36 months at −80° C. and −20° C. 56 days at 5° C., 28 days at 25° C./60% RH and 40° C./75% RH ° C. 120 min Agitation, 8X Freeze/Thaw |

The stability results for the co-formulated drug substance are summarized in Tables 25-34 below:

TABLE 25

Research Stability of mAb1:aflibercept (10 mg/mL:40 mg/mL) Formulated Drug Substance Stored at −80° C.

| Formulation | 10 mg/mL mAb1, 40 mg/mL aflibercept, 10 mM sodium phosphate, pH 6.2, 40 mM sodium chloride, 0.03% (w/v) polysorbate 20, 5% (w/v) sucrose |
|---|---|
| Fill Volume | 1.0 mL |
| Container/Closure | 5 mL polycarbonate vial with silicone lined polypropylene screw cap |

| | | Length of Storage (months) | | | | | |
|---|---|---|---|---|---|---|---|
| Assay | | 0 | 1 | 3 | 6 | 9 | 12 |
| Color and Appearance | | Pass | Pass | Pass | Pass | Pass | Pass |
| Turbidity (Increase in OD at 405 nm) | | 0.00 | 0.01 | 0.00 | 0.00 | 0.00 | 0.00 |
| pH | | 6.3 | 6.3 | 6.3 | 6.3 | 6.3 | 6.3 |
| % Total Recovered by RP-HPLC | mAb1 | 100 | 104 | 104 | 95 | 99 | 94 |
| | Aflibercept | 100 | 102 | 101 | 103 | 99 | 102 |
| Purity by SDS-PAGE | Non-reduced; % mAb1 main + % Aflibercept main | 98 | NR | NR | 98 | NR | 96 |
| | Reduced; % mAb1 heavy chain + % mAb1 light chain + % Aflibercept main | 98 | NR | NR | 98 | NR | 98 |
| Purity by SE-UPLC | % Total HMW | 2.5 | 2.5 | 2.4 | 2.4 | 2.4 | 2.4 |
| | % Total Native | 96.8 | 97.0 | 96.9 | 97.4 | 97.0 | 97.0 |
| | % Total LMW | 0.7 | 0.6 | 0.7 | 0.2 | 0.6 | 0.6 |
| Charge Variant Analysis by iCIEF | mAb1 % Acidic | 33.6 | 34.3 | 33.6 | 33.8 | 35.6 | 33.9 |
| | % Main | 59.9 | 60.0 | 59.7 | 59.7 | 57.6 | 59.8 |
| | % Basic | 6.5 | 5.8 | 6.7 | 6.6 | 6.8 | 6.3 |

TABLE 25-continued

Research Stability of mAb1:aflibercept (10 mg/mL:40 mg/mL)
Formulated Drug Substance Stored at −80° C.

|  |  |  |  |  |  |  |  |
|---|---|---|---|---|---|---|---|
|  | Aflibercept | % Acidic | 17.4 | 17.3 | 17.1 | 16.8 | 17.9 | 16.7 |
|  |  | % Main | 78.4 | 78.6 | 78.6 | 78.9 | 77.8 | 79.2 |
|  |  | % Basic | 4.2 | 4.2 | 4.4 | 4.3 | 4.4 | 4.1 |
| % Relative | mAb1 |  | 87 | NR | NR | 123 | NR | 86 |
| Potency by | Aflibercept |  | 118 | NR | NR | 132 | NR | 100 |
| Bioassay |  |  |  |  |  |  |  |  |

TABLE 26

Research Stability of mAb1:aflibercept (10 mg/mL:40 mg/mL)
Formulated Drug Substance Stored at −30° C.

| Formulation | 10 mg/mL mAb1, 40 mg/mL aflibercept, 10 mM sodium phosphate, pH 6.2, 40 mM sodium chloride, 0.03% (w/v) polysorbate 20, 5% (w/v) sucrose |
|---|---|
| Fill Volume | 1.0 mL |
| Container/Closure | 5 mL polycarbonate vial with silicone lined polypropylene screw cap |

| | | | Length of Storage (months) | | | | | |
|---|---|---|---|---|---|---|---|---|
| Assay | | | 0 | 1 | 3 | 6 | 9 | 12 |
| Color and Appearance | | | Pass | Pass | Pass | Pass | Pass | Pass |
| Turbidity (Increase in OD at 405 nm) | | | 0.00 | 0.01 | 0.00 | 0.00 | 0.00 | 0.00 |
| pH | | | 6.3 | 6.3 | 6.3 | 6.3 | 6.3 | 6.3 |
| % Total | mAb1 | | 100 | 105 | 104 | 94 | 102 | 95 |
| Recovered by | Aflibercept | | 100 | 103 | 102 | 103 | 101 | 102 |
| RP-HPLC | | | | | | | | |
| Purity by | Non-reduced; | | 98 | NR | NR | 98 | NR | 96 |
| SDS-PAGE | % mAb1 main + | | | | | | | |
|  | % Aflibercept main | | | | | | | |
|  | Reduced; | | 98 | NR | NR | 98 | NR | 98 |
|  | % mAb1 heavy chain + | | | | | | | |
|  | % mAb1 light chain + | | | | | | | |
|  | % Aflibercept main | | | | | | | |
| Purity by | % Total HMW | | 2.5 | 2.5 | 2.4 | 2.5 | 2.4 | 2.4 |
| SE-UPLC | % Total Native | | 96.8 | 96.9 | 96.9 | 97.3 | 97.0 | 97.2 |
|  | % Total LMW | | 0.7 | 0.6 | 0.7 | 0.2 | 0.6 | 0.5 |
| Charge Variant | mAb1 | % Acidic | 33.6 | 34.2 | 34.4 | 34.3 | 33.5 | 33.6 |
| Analysis by |  | % Main | 59.9 | 59.3 | 59.1 | 60.1 | 60.0 | 60.0 |
| iCIEF |  | % Basic | 6.5 | 6.5 | 6.5 | 5.6 | 6.5 | 6.4 |
|  | Aflibercept | % Acidic | 17.4 | 17.0 | 17.1 | 17.5 | 17.1 | 17.1 |
|  |  | % Main | 78.4 | 78.7 | 78.8 | 78.5 | 78.7 | 78.8 |
|  |  | % Basic | 4.2 | 4.3 | 4.2 | 4.1 | 4.2 | 4.1 |
| % Relative | mAb1 | | 87 | NR | NR | NR | NR | NR |
| Potency by | Aflibercept | | 118 | NR | NR | NR | NR | NR |
| Bioassay | | | | | | | | |

TABLE 27

Research Stability of mAb1:aflibercept (10 mg/mL:40 mg/mL)
Formulated Drug Substance Stored at −20° C.

| Formulation | 10 mg/mL mAb1, 40 mg/mL aflibercept, 10 mM sodium phosphate, pH 6.2, 40 mM sodium chloride, 0.03% (w/v) polysorbate 20, 5% (w/v) sucrose |
|---|---|
| Fill Volume | 1.0 mL |
| Container/Closure | 5 mL polycarbonate vial with silicone lined polypropylene screw cap |

| | | Length of Storage (months) | | | | | |
|---|---|---|---|---|---|---|---|
| Assay | | 0 | 1 | 3 | 6 | 9 | 12 |
| Color and Appearance | | Pass | Pass | Pass | Pass | Pass | Pass |
| Turbidity (Increase in OD at 405 nm) | | 0.00 | 0.01 | 0.00 | 0.00 | 0.00 | 0.00 |
| pH | | 6.3 | 6.3 | 6.3 | 6.3 | 6.3 | 6.3 |
| % Total | mAb1 | 100 | 105 | 101 | 101 | 108 | 98 |
| Recovered by | Aflibercept | 100 | 103 | 100 | 100 | 103 | 105 |
| RP-HPLC | | | | | | | |

TABLE 27-continued

Research Stability of mAb1:aflibercept (10 mg/mL:40 mg/mL)
Formulated Drug Substance Stored at −20° C.

| | | | | | | | | |
|---|---|---|---|---|---|---|---|---|
| Purity by SDS-PAGE | Non-reduced; % mAb1 main + % Aflibercept main | | 98 | NR | NR | 98 | NR | 96 |
| | Reduced; % mAb1 heavy chain + % mAb1 light chain + % Aflibercept main | | 98 | NR | NR | 96 | NR | 98 |
| Purity by SE-UPLC | % Total HMW | | 2.5 | 2.5 | 2.6 | 2.8 | 2.6 | 2.7 |
| | % Total Native | | 96.8 | 97.0 | 96.6 | 97.1 | 96.8 | 96.7 |
| | % Total LMW | | 0.7 | 0.5 | 0.7 | 0.2 | 0.6 | 0.6 |
| Charge Variant Analysis by iCIEF | mAb1 | % Acidic | 33.6 | 34.5 | 33.2 | 34.2 | 33.8 | 33.5 |
| | | % Main | 59.9 | 59.2 | 61.0 | 59.6 | 59.9 | 60.1 |
| | | % Basic | 6.5 | 6.3 | 5.8 | 6.2 | 6.3 | 6.4 |
| | Aflibercept | % Acidic | 17.4 | 17.5 | 17.3 | 17.4 | 16.9 | 17.0 |
| | | % Main | 78.4 | 78.5 | 78.6 | 78.4 | 78.9 | 78.8 |
| | | % Basic | 4.2 | 4.0 | 4.2 | 4.3 | 4.2 | 4.2 |
| % Relative Potency by Bioassay | mAb1 | | 87 | NR | NR | 98 | NR | 120 |
| | Aflibercept | | 118 | NR | NR | 126 | NR | 125 |

TABLE 28

Research Stability of mAb1:aflibercept (120 mg/mL:40 mg/mL)
Formulated Drug Substance Stored at −80° C.

| | |
|---|---|
| Formulation | 120 mg/mL mAb1, 40 mg/mL aflibercept, 10 mM sodium phosphate, pH 6.2, 40 mM sodium chloride, 0.03% (w/v) polysorbate 20, 5% (w/v) sucrose |
| Fill Volume | 1.0 mL |
| Container/Closure | 5 mL polycarbonate vial with silicone lined polypropylene screw cap |

| | | | Length of Storage (months) | | | | | |
|---|---|---|---|---|---|---|---|---|
| Assay | | | 0 | 1 | 3 | 6 | 9 | 12 |
| Color and Appearance | | | Pass | Pass | Pass | Pass | Pass | Pass |
| Turbidity (Increase in OD at 405 nm) | | | 0.00 | 0.01 | 0.01 | 0.00 | 0.00 | 0.00 |
| pH | | | 6.3 | 6.3 | 6.3 | 6.3 | 6.3 | 6.3 |
| % Total Recovered by RP-HPLC | mAb1 | | 100 | 103 | 99 | 100 | 105 | 104 |
| | Aflibercept | | 100 | 98 | 94 | 99 | 96 | 96 |
| Purity by SDS-PAGE | Non-reduced; % mAb1 main + % Aflibercept main | | 98 | NR | NR | 98 | NR | 97 |
| | Reduced; % mAb1 heavy chain + % mAb1 light chain + % Aflibercept main | | 99 | NR | NR | 99 | NR | 98 |
| Purity by SE-UPLC | % Total HMW | | 2.8 | 2.7 | 2.7 | 2.7 | 2.7 | 2.6 |
| | % Total Native | | 96.4 | 96.6 | 96.4 | 96.9 | 96.3 | 96.9 |
| | % Total LMW | | 0.8 | 0.7 | 1.0 | 0.4 | 1.0 | 0.6 |
| Charge Variant Analysis by iCIEF | mAb1 | % Acidic | 33.3 | 33.4 | 33.6 | 33.2 | 33.3 | 33.6 |
| | | % Main | 60.4 | 60.4 | 60.0 | 60.5 | 60.3 | 60.1 |
| | | % Basic | 6.3 | 6.3 | 6.4 | 6.3 | 6.5 | 6.3 |
| | Aflibercept | % Acidic | 15.9 | 14.7 | 15.8 | 15.6 | 17.3 | 14.6 |
| | | % Main | 80.7 | 81.2 | 80.0 | 80.6 | 78.8 | 80.9 |
| | | % Basic | 3.4 | 4.1 | 4.2 | 3.8 | 3.9 | 4.4 |
| % Relative Potency by Bioassay | mAb1 | | 70 | NR | NR | 130 | NR | 80 |
| | Aflibercept | | 109 | NR | NR | 109 | NR | 84 |

TABLE 29

Research Stability of mAb1:aflibercept (120 mg/mL:40 mg/mL)
Formulated Drug Substance Stored at −30° C.

| | |
|---|---|
| Formulation | 120 mg/mL mAb1, 40 mg/mL aflibercept, 10 mM sodium phosphate, pH 6.2, 40 mM sodium chloride, 0.03% (w/v) polysorbate 20, 5% (w/v) sucrose |

TABLE 29-continued

Research Stability of mAb1:aflibercept (120 mg/mL:40 mg/mL)
Formulated Drug Substance Stored at −30° C.

Fill Volume 1.0 mL
Container/Closure 5 mL polycarbonate vial with silicone lined polypropylene screw cap

| Assay | | | Length of Storage (months) | | | | | |
|---|---|---|---|---|---|---|---|---|
| | | | 0 | 1 | 3 | 6 | 9 | 12 |
| Color and Appearance | | | Pass | Pass | Pass | Pass | Pass | Pass |
| Turbidity (Increase in OD at 405 nm) | | | 0.00 | 0.01 | 0.00 | 0.00 | 0.00 | 0.00 |
| pH | | | 6.3 | 6.3 | 6.3 | 6.3 | 6.3 | 6.3 |
| % Total Recovered by RP-HPLC | mAb1 | | 100 | 105 | 101 | 104 | 104 | 105 |
| | Aflibercept | | 100 | 99 | 94 | 101 | 96 | 97 |
| Purity by SDS-PAGE | Non-reduced; % mAb1 main + % Aflibercept main | | 98 | NR | NR | 98 | NR | 97 |
| | Reduced; % mAb1 heavy chain + % mAb1 light chain + % Aflibercept main | | 99 | NR | NR | 99 | NR | 98 |
| Purity by SE-UPLC | % Total HMW | | 2.8 | 2.7 | 2.7 | 2.8 | 2.8 | 2.7 |
| | % Total Native | | 96.4 | 96.6 | 96.8 | 96.7 | 96.3 | 96.8 |
| | % Total LMW | | 0.8 | 0.7 | 0.6 | 0.6 | 1.0 | 0.6 |
| Charge Variant Analysis by iCIEF | mAb1 | % Acidic | 33.3 | 33.5 | 33.5 | 33.4 | 33.2 | 33.5 |
| | | % Main | 60.4 | 60.3 | 60.1 | 60.3 | 60.4 | 60.3 |
| | | % Basic | 6.3 | 6.3 | 6.3 | 6.3 | 6.4 | 6.2 |
| | Aflibercept | % Acidic | 15.9 | 16.2 | 16.1 | 17.3 | 16.8 | 14.9 |
| | | % Main | 80.7 | 79.4 | 79.6 | 78.6 | 79.3 | 80.6 |
| | | % Basic | 3.4 | 4.4 | 4.3 | 4.1 | 3.9 | 4.5 |
| % Relative Potency by Bioassay | mAb1 | | 70 | NR | NR | NR | NR | NR |
| | Aflibercept | | 109 | NR | NR | NR | NR | NR |

TABLE 30

Research Stability of mAb1:aflibercept (120 mg/mL:40 mg/mL)
Formulated Drug Substance Stored at −20° C.

Formulation 120 mg/mL mAb1, 40 mg/mL aflibercept, 10 mM sodium phosphate, pH 6.2,
40 mM sodium chloride, 0.03% (w/v) polysorbate 20, 5% (w/v) sucrose
Fill Volume 1.0 mL
Container/Closure 5 mL polycarbonate vial with silicone lined polypropylene screw cap

| Assay | | | Length of Storage (months) | | | | | |
|---|---|---|---|---|---|---|---|---|
| | | | 0 | 1 | 3 | 6 | 9 | 12 |
| Color and Appearance | | | Pass | Pass | Pass | Pass | Pass | Pass |
| Turbidity (Increase in OD at 405 nm) | | | 0.00 | 0.01 | 0.00 | 0.00 | 0.00 | 0.00 |
| pH | | | 6.3 | 6.3 | 6.3 | 6.3 | 6.3 | 6.3 |
| % Total Recovered by RP-HPLC | mAb1 | | 100 | 104 | 103 | 103 | 106 | 107 |
| | Aflibercept | | 100 | 99 | 96 | 101 | 97 | 99 |
| Purity by SDS-PAGE | Non-reduced; % mAb1 main + % Aflibercept main | | 98 | NR | NR | 97 | NR | 97 |
| | Reduced; % mAb1 heavy chain + % mAb1 light chain + % Aflibercept main | | 99 | NR | NR | 99 | NR | 97 |
| Purity by SE-UPLC | % Total HMW | | 2.8 | 2.7 | 2.7 | 2.8 | 2.9 | 2.8 |
| | % Total Native | | 96.4 | 96.7 | 96.6 | 96.7 | 96.2 | 96.7 |
| | % Total LMW | | 0.8 | 0.6 | 0.8 | 0.6 | 0.9 | 0.6 |
| Charge Variant Analysis by iCIEF | mAb1 | % Acidic | 33.3 | 34.2 | 34.1 | 33.9 | 34.7 | 33.3 |
| | | % Main | 60.4 | 59.6 | 59.6 | 59.8 | 59.1 | 60.4 |
| | | % Basic | 6.3 | 6.2 | 6.4 | 6.3 | 6.2 | 6.3 |
| | Aflibercept | % Acidic | 15.9 | 16.4 | 14.3 | 17.2 | 15.5 | 16.7 |
| | | % Main | 80.7 | 80.0 | 81.3 | 78.0 | 79.5 | 79.1 |
| | | % Basic | 3.4 | 3.7 | 4.4 | 4.8 | 5.1 | 4.2 |
| % Relative Potency by Bioassay | mAb1 | | 70 | NR | NR | 83 | NR | 110 |
| | Aflibercept | | 109 | NR | NR | 133 | NR | 140 |

TABLE 31

Research Stability of mAb1:aflibercept (10 mg/mL:40 mg/mL) Formulated Drug Substance - Effect of Accelerated Conditions

| Formulation | 10 mg/mL mAb1, 40 mg/mL aflibercept, 10 mM sodium phosphate, pH 6.2, 40 mM sodium chloride, 0.03% (w/v) polysorbate 20, 5% (w/v) sucrose |
|---|---|
| Fill Volume | 1.0 mL |
| Container/Closure | 5 mL polycarbonate vial w/silicone lined polypropylene screw cap |

| | | | Storage Condition/Length of Storage (days) | | | | | | | | |
|---|---|---|---|---|---|---|---|---|---|---|---|
| | | | No Storage | 5° C. | | | 25° C./ 60% RH | | | 40° C./ 75% RH | | |
| Assay | | | 0 | 14 | 28 | 56 | 7 | 14 | 28 | 7 | 14 | 28 |
| Color and Appearance | | | Pass | Pass | Pass | Pass | Pass | Pass | Pass | Pass | Pass | Pass |
| Turbidity (Increase in OD at 405 nm) | | | 0.00 | 0.00 | 0.00 | 0.00 | 0.00 | 0.00 | 0.00 | 0.00 | 0.01 | 0.00 |
| pH | | | 6.3 | 6.3 | 6.3 | 6.4 | 6.3 | 6.3 | 6.3 | 6.3 | 6.3 | 6.2 |
| % Total Recovered by RP-HPLC | mAb1 | | 100 | 97 | 105 | 102 | 98 | 102 | 113 | 101 | 103 | 115 |
| | Aflibercept | | 100 | 103 | 105 | 106 | 105 | 108 | 109 | 108 | 110 | 114[1)] |
| Purity by SDS-PAGE | Non-reduced; % mAb1 main + % Aflibercept main | | 98 | NR | NR | 97 | NR | NR | 98 | NR | NR | 95 |
| | Reduced; % mAb1 heavy chain + % mAb1 light chain + % Aflibercept main | | 98 | NR | NR | 98 | NR | NR | 97 | NR | NR | 96 |
| Purity by SE-UPLC | % Total HMW | | 2.5 | 2.2 | 2.3 | 2.3 | 2.2 | 2.6 | 2.8 | 4.8 | 9.5 | 11.2 |
| | % Total Native | | 96.8 | 96.6 | 97.1 | 97.6 | 96.8 | 96.3 | 96.6 | 94.2 | 88.8 | 87.9 |
| | % Total LMW | | 0.7 | 1.2 | 0.6 | 0.2 | 1.0 | 1.2 | 0.7 | 1.0 | 1.7 | 0.9 |
| Charge Variant Analysis by iCIEF | mAb1 | % Acidic | 33.6 | 34.2 | 34.2 | 34.3 | 34.3 | 36.3 | 36.3 | 38.7 | 49.6 | 53.5 |
| | | % Main | 59.9 | 59.3 | 59.3 | 59.5 | 59.8 | 56.9 | 56.7 | 53.6 | 42.0 | 38.3 |
| | | % Basic | 6.5 | 6.5 | 6.5 | 6.2 | 6.0 | 6.8 | 7.0 | 7.7 | 8.4 | 8.2 |
| | Aflibercept | % Acidic | 17.4 | 17.6 | 17.6 | 16.9 | 17.2 | 17.3 | 18.1 | 18.3 | 21.9 | 23.4 |
| | | % Main | 78.4 | 78.0 | 78.0 | 78.8 | 78.6 | 78.5 | 77.8 | 77.8 | 75.5 | 73.8 |
| | | % Basic | 4.2 | 4.4 | 4.4 | 4.3 | 4.2 | 4.2 | 4.2 | 3.9 | 2.7 | 2.8 |
| % Relative Potency by Bioassay | mAb1 | | 87 | NR | NR | 97 | NR | NR | 113 | NR | NR | 136 |
| | Aflibercept | | 118 | NR | NR | 109 | NR | NR | 71 | NR | NR | 112 |

TABLE 32

Research Stability of mAb1:aflibercept (120 mg/mL:40 mg/mL) Formulated Drug Substance - Effect of Accelerated Conditions

| Formulation | 120 mg/mL mAb1, 40 mg/mL aflibercept, 10 mM sodium phosphate, pH 6.2, 40 mM sodium chloride, 0.03% (w/v) polysorbate 20, 5% (w/v) sucrose |
|---|---|
| Fill Volume | 1.0 mL |
| Container/Closure | 5 mL polycarbonate vial w/silicone lined polypropylene screw cap |

| | | | Storage Condition/Length of Storage (days) | | | | | | | | |
|---|---|---|---|---|---|---|---|---|---|---|---|
| | | | No Storage | 5° C. | | | 25° C./ 60% RH | | | 40° C./ 75% RH | | |
| Assay | | | 0 | 14 | 28 | 56 | 7 | 14 | 28 | 7 | 14 | 28 |
| Color and Appearance | | | Pass | Pass | Pass | Pass | Pass | Pass | Pass | Pass | Pass | Pass |
| Turbidity (Increase in OD at 405 nm) | | | 0.00 | 0.00 | 0.00 | 0.00 | 0.01 | 0.00 | 0.01 | 0.00 | 0.01 | 0.01 |
| pH | | | 6.3 | 6.3 | 6.3 | 6.4 | 6.3 | 6.3 | 6.2 | 6.3 | 6.3 | 6.2 |
| % Total Recovered by RP-HPLC | mAb1 | | 100 | 99 | 103 | 100 | 102 | 102 | 110 | 102 | 104 | 126 |
| | Aflibercept | | 100 | 101 | 102 | 101 | 103 | 103 | 107 | 103 | 104 | 118[1)] |
| Purity by SDS-PAGE | Non-reduced; % mAb1 main + % Aflibercept main | | 98 | NR | NR | 95 | NR | NR | 97 | NR | NR | 94 |
| | Reduced; % mAb1 heavy chain + % mAb1 light chain + % Aflibercept main | | 99 | NR | NR | 99 | NR | NR | 99 | NR | NR | 97 |
| Purity by SE-UPLC | % Total HMW | | 2.8 | 2.8 | 2.9 | 3.0 | 3.0 | 3.4 | 3.5 | 5.1 | 8.6 | 10.7 |
| | % Total Native | | 96.4 | 96.0 | 96.4 | 96.4 | 96.1 | 95.3 | 95.5 | 93.8 | 89.2 | 87.0 |
| | % Total LMW | | 0.8 | 1.1 | 0.7 | 0.6 | 0.9 | 1.3 | 0.9 | 1.1 | 2.3 | 2.3 |
| Charge Variant Analysis by iCIEF | REGN 910 | % Acidic | 33.3 | 33.5 | 33.6 | 33.5 | 34.2 | 35.8 | 36.2 | 38.7 | 48.9 | 51.9 |
| | | % Main | 60.4 | 60.1 | 60.1 | 60.0 | 59.1 | 57.4 | 56.8 | 53.4 | 42.0 | 38.7 |
| | | % Basic | 6.3 | 6.4 | 6.3 | 6.4 | 6.7 | 6.9 | 7.0 | 7.9 | 9.1 | 9.4 |

TABLE 32-continued

Research Stability of mAb1:aflibercept (120 mg/mL:40 mg/mL) Formulated Drug Substance - Effect of Accelerated Conditions

|  |  |  |  |  |  |  |  |  |  |  |  |
|---|---|---|---|---|---|---|---|---|---|---|---|
|  | Aflibercept | % Acidic | 15.9 | 15.8 | 15.7 | 15.8 | 15.9 | 16.4 | 16.9 | 14.4 | 19.8 | 22.8 |
|  |  | % Main | 80.7 | 80.3 | 79.9 | 80.0 | 79.6 | 79.4 | 78.9 | 81.7 | 77.1 | 75.0 |
|  |  | % Basic | 3.4 | 3.9 | 4.3 | 4.2 | 4.5 | 4.2 | 4.2 | 3.9 | 3.1 | 2.2 |
| % Relative Potency by Bioassay | mAb1 |  | 70 | NR | NR | 97 | NR | NR | 141 | NR | NR | 143 |
|  | Aflibercept |  | 109 | NR | NR | 121 | NR | NR | 107 | NR | NR | 104 |

TABLE 33

Research Stability of mAb1:aflibercept (10 mg/mL:40 mg/mL)
Formulated Drug Substance - Effect of Stress Conditions

| Formulation | 10 mg/mL mAb1, 40 mg/mL aflibercept, 10 mM sodium phosphate, pH 6.2, 40 mM sodium chloride, 0.03% (w/v) polysorbate 20, 5% (w/v) sucrose |
|---|---|
| Fill Volume | 1.0 mL |
| Container/Closure | 5 mL polycarbonate vial w/silicone lined polypropylene screw cap |

|  |  |  | Stress Condition/Length of Stress | | | | |
|---|---|---|---|---|---|---|---|
|  |  |  | No Stress | Agitation (minutes) | | Freeze/Thaw (Cycles) | |
|  | Assay |  | 0 | 60 | 120 | 4 | 8 |
| Color and Appearance | | | Pass | Pass | Pass | Pass | Pass |
| Turbidity (Increase in OD at 405 nm) | | | 0.00 | 0.00 | 0.00 | 0.00 | 0.00 |
| pH | | | 6.3 | 6.3 | 6.3 | 6.3 | 6.2 |
| % Total Recovered by RP-HPLC | mAb1 | | 100 | 99 | 99 | 105 | 104 |
|  | Aflibercept | | 100 | 103 | 103 | 102 | 102 |
| Purity by SDS-PAGE | Non-reduced; % mAb1 main + % Aflibercept main | | 98 | NR | 98 | NR | 98 |
|  | Reduced; % mAb1 heavy chain + % mAb1 light chain + % Aflibercept main | | 98 | NR | 98 | NR | 98 |
| Purity by SE-UPLC | % Total HMW | | 2.5 | 2.4 | 2.3 | 2.5 | 2.4 |
|  | % Total Native | | 96.8 | 96.8 | 97.0 | 97.0 | 97.0 |
|  | % Total LMW | | 0.7 | 0.8 | 0.7 | 0.5 | 0.6 |
| Charge Variant Analysis by iCIEF | mAb1 | % Acidic | 33.6 | 34.3 | 34.5 | 34.7 | 35.0 |
|  |  | % Main | 59.9 | 59.6 | 59.3 | 59.4 | 58.8 |
|  |  | % Basic | 6.5 | 6.1 | 6.2 | 5.9 | 6.2 |
|  | Aflibercept | % Acidic | 17.4 | 17.9 | 17.9 | 17.8 | 17.9 |
|  |  | % Main | 78.4 | 77.9 | 77.8 | 78.1 | 77.8 |
|  |  | % Basic | 4.2 | 4.2 | 4.3 | 4.1 | 4.3 |
| % Relative Potency by Bioassay | mAb1 | | 87 | NR | 96 | NR | 113 |
|  | Aflibercept | | 118 | NR | 104 | NR | 133 |

TABLE 34

Research Stability of mAb1:aflibercept (120 mg/mL:40 mg/mL)
Formulated Drug Substance - Effect of Stress Conditions

| Formulation | 120 mg/mL mAb1, 40 mg/mL aflibercept, 10 mM sodium phosphate, pH 6.2, 40 mM sodium chloride, 0.03% (w/v) polysorbate 20, 5% (w/v) sucrose |
|---|---|
| Fill Volume | 1.0 mL |
| Container/Closure | 5 mL polycarbonate vial w/silicone lined polypropylene screw cap |

|  |  | Stress Condition/Length of Stress | | | | |
|---|---|---|---|---|---|---|
|  |  | No Stress | Agitation (minutes) | | Freeze/Thaw (Cycles) | |
|  | Assay | 0 | 60 | 120 | 4 | 8 |
| Color and Appearance | | Pass | Pass | Pass | Pass | Pass |
| Turbidity (Increase in OD at 405 nm) | | 0.00 | 0.00 | 0.00 | 0.01 | 0.01 |
| pH | | 6.3 | 6.3 | 6.3 | 6.3 | 6.3 |
| % Total Recovered by RP-HPLC | mAb1 | 100 | 99 | 101 | 104 | 103 |
|  | Aflibercept | 100 | 98 | 101 | 98 | 98 |

TABLE 34-continued

Research Stability of mAb1:aflibercept (120 mg/mL:40 mg/mL)
Formulated Drug Substance - Effect of Stress Conditions

| | | | | | | | |
|---|---|---|---|---|---|---|---|
| Purity by SDS-PAGE | Non-reduced; % mAb1 main + % Aflibercept main | | 98 | NR | 98 | NR | 98 |
| | Reduced; % mAb1 heavy chain + % mAb1 light chain + % Aflibercept main | | 99 | NR | 99 | NR | 99 |
| Purity by SE-UPLC | % Total HMW | | 2.8 | 3.2 | 3.7 | 2.7 | 2.8 |
| | % Total Native | | 96.4 | 96.3 | 95.7 | 96.5 | 96.4 |
| | % Total LMW | | 0.8 | 0.6 | 0.6 | 0.8 | 0.8 |
| Charge Variant Analysis by iCIEF | mAb1 | % Acidic | 33.3 | 34.3 | 34.2 | 33.9 | 34.0 |
| | | % Main | 60.4 | 59.4 | 59.4 | 59.8 | 59.6 |
| | | % Basic | 6.3 | 6.2 | 6.4 | 6.4 | 6.3 |
| | Aflibercept | % Acidic | 15.9 | 16.8 | 16.3 | 15.8 | 16.6 |
| | | % Main | 80.7 | 78.3 | 79.0 | 79.9 | 79.3 |
| | | % Basic | 3.4 | 4.9 | 4.7 | 4.3 | 4.2 |
| % Relative Potency by Bioassay | mAb1 | | 70 | NR | 97 | NR | 75 |
| | Aflibercept | | 109 | NR | 95 | NR | 143 |

The stability of the co-formulated drug products was studied as shown in Tables 35 and 36:

TABLE 35

Research Stability Studies for mAb1:aflibercept Drug Products

| Storage Stability[1] | | Container/Closure |
|---|---|---|
| Storage Temperature | Length of Storage (months) | Type 1 borosilicate glass with FluroTec ® coated 4432/50 butyl rubber stopper |
| 5° C. | 0, 1, 3, 6, 9, 12, 18, 24, and 36 | |
| Accelerated Stability[2] | | |
| Incubation Condition | Length of Incubation | |
| 25° C. | 0, 1, 3, and 6 months | |
| 37° C. | 0, 7, 14, and 28 days | |
| Stress Stability | | |
| Stress | Duration of Stress | |
| Agitation (vortex) | 0, 60, and 120 minutes | |
| Freeze/Thaw[3] | 0, 4, and 8 cycles | |

TABLE 36

Research Stability Studies Analysis Plan
for mAb1:aflibercept Drug Products

| Assay | Samples to be Analyzed |
|---|---|
| Color and Appearance | All Samples |
| pH | All Samples |
| Turbidity (Increase in OD at 405 nm) | All Samples |
| % Total mAb1 Recovered by RP-HPLC | All Samples |
| % Aflibercept Recovered by RP-HPLC | All Samples |
| Total Purity (mAb1 + aflibercept) by Non-Reduced and Reduced SDS-PAGE | t = 0, 6, 12, 24 and 36 months at 5° C.; 6 months at 25° C.; 28 days at 37° C. 120 min Agitation, 8X Freeze/Thaw |
| Total (mAb1 + aflibercept) Purity by SE-UPLC | All Samples |
| mAb1 Charge Variant Analysis by iCIEF | All Samples |
| Aflibercept Charge Variant Analysis by iCIEF | All Samples |
| Particulate Matter Analysis by MFI | t = 0, 6, 12, 24 and 36 months at 5° C.; 6 months at 25° C.; 28 days at 37° C. 120 min Agitation, 8X Freeze/Thaw |
| % mAb1 Relative Potency by Bioassay | t = 0, 6, 12, 24 and 36 months at 5° C.; 6 months at 25° C.; 28 days at 37° C. 120 min Agitation, 8X Freeze/Thaw |
| % Aflibercept Relative Potency by Bioassay | t = 0, 6, 12, 24 and 36 months at 5° C.; 6 months at 25° C.; 28 days at 37° C. 120 min Agitation, 8X Freeze/Thaw |

The results of the stability for the co-formulated drug products are summarized in Tables 37-42 below:

TABLE 37

Research Stability of mAb1:aflibercept (10 mg/mL:40 mg/mL) Drug Product Stored at 5° C.

| | |
|---|---|
| Formulation | 10 mg/mL mAb1, 40 mg/mL aflibercept, 10 mM sodium phosphate, pH 6.2, 40 mM sodium chloride, 0.03% (w/v) polysorbate 20, 5% (w/v) sucrose |
| Fill Volume | 0.5 mL |
| Container/Closure | 2 mL Type I borosilicate glass vial with West S2-F451 4432/50 GRY B2-40 stopper |

| | Length of Storage (months) | | | | |
|---|---|---|---|---|---|
| Assay | 0 | 1 | 3 | 6 | 9 |
| Color and Appearance | Pass | Pass | Pass | Pass | Pass |
| Turbidity (Increase in OD at 405 nm) | 0.00 | 0.00 | 0.00 | 0.00 | 0.00 |
| pH | 6.3 | 6.3 | 6.3 | 6.3 | 6.3 |

TABLE 37-continued

Research Stability of mAb1:aflibercept (10 mg/mL:40 mg/mL) Drug Product Stored at 5° C.

| | | | | | | |
|---|---|---|---|---|---|---|
| % Total Recovered by RP-HPLC | mAb1 | 100 | 100 | 95 | 104 | 94 |
| | Aflibercept | 100 | 102 | 101 | 97 | 97 |
| Purity by SDS-PAGE | Non-reduced; % mAb1 main + % Aflibercept main | 99 | NR | NR | 98 | NR |
| | Reduced; % mAb1 heavy chain + % mAb1 light chain + % Aflibercept main | 97 | NR | NR | 98 | NR |
| Purity by SE-UPLC | % Total HMW | 1.6 | 1.7 | 1.8 | 1.9 | 2.0 |
| | % Total Native | 97.6 | 97.8 | 97.8 | 97.4 | 97.5 |
| | % Total LMW | 0.8 | 0.6 | 0.4 | 0.7 | 0.5 |
| Charge Variant Analysis by iCIEF | mAb1  % Acidic | 37.1 | 37.6 | 37.5 | 37.5 | 37.6 |
| | % Main | 58.1 | 58.0 | 57.8 | 58.2 | 57.8 |
| | % Basic | 4.8 | 4.4 | 4.7 | 4.3 | 4.7 |
| | Aflibercept  % Acidic | 19.5 | 19.7 | 19.7 | 20.3 | 19.4 |
| | % Main | 77.5 | 77.0 | 76.3 | 76.7 | 77.7 |
| | % Basic | 3.0 | 3.2 | 4.0 | 3.0 | 2.9 |
| Particulate Analysis by MFI (particles/mL) | ≥2 μm | 4137 | NR | NR | 2344 | NR |
| | ≥10 μm | 103 | NR | NR | 23 | NR |
| | ≥25 μm | 15 | NR | NR | 0 | NR |
| % Relative Potency (Bioassay) | mAb1 | 124 | NR | NR | 78 | 124 |
| | Aflibercept | 125 | NR | NR | 165 | 107 |

TABLE 38

Research Stability of mAb1:aflibercept (120 mg/mL:40 mg/mL) Drug Product Stored at 5° C.

| | |
|---|---|
| Formulation | 120 mg/mL mAb1, 40 mg/mL aflibercept, 10 mM sodium phosphate, pH 6.2, 40 mM sodium chloride, 0.03% (w/v) polysorbate 20, 5% (w/v) sucrose |
| Fill Volume | 0.5 mL |
| Container/Closure | 2 mL Type I borosilicate glass vial with West S2-F451 4432/50 GRY B2-40 stopper |

| | | Length of Storage (months) | | | | |
|---|---|---|---|---|---|---|
| Assay | | 0 | 1 | 3 | 6 | 9 |
| Color and Appearance | | Pass | Pass | Pass | Pass | Pass |
| Turbidity (Increase in OD at 405 nm) | | 0.00 | 0.00 | 0.00 | 0.00 | 0.00 |
| pH | | 6.3 | 6.4 | 6.3 | 6.3 | 6.3 |
| % Total Recovered by RP-HPLC | mAb1 | 100 | 102 | 101 | 103 | 102 |
| | Aflibercept | 100 | 103 | 104 | 98 | 99 |
| Purity by SDS-PAGE | Non-reduced; % mAb1 main + % Aflibercept main | 97 | NR | NR | 96 | NR |
| | Reduced; % mAb1 heavy chain + % mAb1 light chain + % Aflibercept main | 95 | NR | NR | 96 | NR |
| Purity by SE-UPLC | % Total HMW | 2.4 | 2.8 | 3.0 | 3.2 | 3.4 |
| | % Total Native | 96.6 | 96.5 | 96.3 | 96.1 | 96.0 |
| | % Total LMW | 1.1 | 0.7 | 0.6 | 0.8 | 0.7 |
| Charge Variant Analysis by iCIEF | mAb1  % Acidic | 37.7 | 37.6 | 37.5 | 37.7 | 37.5 |
| | % Main | 57.8 | 57.9 | 57.8 | 57.6 | 57.7 |
| | % Basic | 4.5 | 4.5 | 4.7 | 4.7 | 4.8 |
| | Aflibercept  % Acidic | 19.5 | 18.0 | 18.2 | 18.8 | 18.1 |
| | % Main | 77.9 | 80.0 | 79.1 | 77.5 | 77.8 |
| | % Basic | 2.6 | 2.0 | 2.7 | 3.7 | 4.0 |
| Particulate Analysis by MFI (particles/mL) | ≥2 μm | 3276 | NR | NR | 2400 | NR |
| | ≥10 μm | 145 | NR | NR | 99 | NR |
| | ≥25 μm | 15 | NR | NR | 7 | NR |
| % Relative Potency (Bioassay) | mAb1 | 87 | NR | NR | 57 | 76 |
| | Aflibercept | 109 | NR | NR | 130 | 63 |

TABLE 39

Research Stability of mAb1:aflibercept (10 mg/mL:40 mg/mL)
Drug Product - Effect of Accelerated Conditions

| | |
|---|---|
| Formulation | 10 mg/mL mAb1, 40 mg/mL aflibercept, 10 mM sodium phosphate, pH 6.2, 40 mM sodium chloride, 0.03% (w/v) polysorbate 20, 5% (w/v) sucrose |
| Fill Volume | 0.5 mL |
| Container/Closure | 2 mL Type I borosilicate glass vial with West S2-F451 4432/50 GRY B2-40 stopper |

| | | | No Storage | 25° C. (months) | | | 37° C. (days) | | |
|---|---|---|---|---|---|---|---|---|---|
| | | Assay | 0 | 1 | 3 | 6 | 7 | 14 | 28 |
| Color and Appearance | | | Pass | Pass | Pass | Pass | Pass | Pass | Pass |
| Turbidity (Increase in OD at 405 nm) | | | 0.00 | 0.00 | 0.00 | 0.00 | 0.00 | 0.00 | 0.00 |
| | | pH | 6.3 | 6.3 | 6.4 | 6.3 | 6.3 | 6.3 | 6.3 |
| % Total Recovered by RP-HPLC | | mAb1 | 100 | 104 | 99 | 102 | 105 | 103 | 107 |
| | | Aflibercept | 100 | 103 | 103 | 98 | 101 | 98 | 101 |
| Purity by SDS-PAGE | | Non-reduced; % mAb1 main + % Aflibercept main | 99 | NR | NR | 94 | NR | NR | 95 |
| | | Reduced; % mAb1 heavy chain + % mAb1 light chain + % Aflibercept main | 97 | NR | NR | 94 | NR | NR | 96 |
| Purity by SE-UPLC | | % Total HMW | 1.6 | 2.3 | 2.8 | 3.5 | 2.8 | 3.7 | 5.3 |
| | | % Total Native | 97.6 | 97.1 | 96.5 | 95.0 | 95.9 | 95.6 | 93.7 |
| | | % Total LMW | 0.8 | 0.7 | 0.7 | 1.5 | 1.3 | 0.8 | 1.0 |
| Charge Variant Analysis by iCIEF | mAb1 | % Acidic | 37.1 | 39.3 | 45.9 | 53.2 | 40.6 | 43.7 | 50.3 |
| | | % Main | 58.1 | 54.9 | 48.2 | 40.5 | 53.7 | 50.2 | 42.7 |
| | | % Basic | 4.8 | 5.8 | 5.9 | 6.2 | 5.7 | 6.1 | 7.0 |
| | Aflibercept | % Acidic | 19.5 | 21.3 | 22.2 | 26.1 | 20.9 | 22.3 | 24.2 |
| | | % Main | 77.5 | 75.5 | 74.7 | 71.4 | 76.0 | 74.7 | 72.8 |
| | | % Basic | 3.0 | 3.2 | 3.1 | 2.6 | 3.1 | 3.0 | 2.9 |
| Particulate Analysis by MFI (particles/mL) | | ≥2 µm | 4137 | NR | NR | 3628 | NR | NR | 1593 |
| | | ≥10 µm | 103 | NR | NR | 105 | NR | NR | 61 |
| | | ≥25 µm | 15 | NR | NR | 17 | NR | NR | 5 |
| % Relative Potency by Bioassay | | mAb1 | 124 | NR | NR | 59 | NR | NR | 123 |
| | | Aflibercept | 125 | NR | NR | 146 | NR | NR | 139 |

TABLE 40

Research Stability of mAb1:aflibercept (120 mg/mL:40 mg/mL)
Drug Product - Effect of Accelerated Conditions

| | |
|---|---|
| Formulation | 120 mg/mL mAb1, 40 mg/mL aflibercept, 10 mM sodium phosphate, pH 6.2, 40 mM sodium chloride, 0.03% (w/v) polysorbate 20, 5% (w/v) sucrose |
| Fill Volume | 0.5 mL |
| Container/Closure | 2 mL Type I borosilicate glass vial with West S2-F451 4432/50 GRY B2-40 stopper |

| | | No Storage | 25° C. (months) | | | 37° C. (days) | | |
|---|---|---|---|---|---|---|---|---|
| | Assay | 0 | 1 | 3 | 6 | 7 | 14 | 28 |
| Color and Appearance | | Pass | Pass | Pass | Pass | Pass | Pass | Pass |
| Turbidity (Increase in OD at 405 nm) | | 0.00 | 0.00 | 0.00 | 0.01 | 0.00 | 0.00 | 0.00 |
| | pH | 6.3 | 6.4 | 6.4 | 6.3 | 6.3 | 6.3 | 6.4 |
| % Total Recovered by RP-HPLC | mAb1 | 100 | 101 | 101 | 103 | 102 | 99 | 103 |
| | Aflibercept | 100 | 102 | 102 | 97 | 100 | 95 | 99 |
| Purity by SDS-PAGE | Non-reduced; % mAb1 main + % Aflibercept main | 97 | NR | NR | 91 | NR | NR | 92 |
| | Reduced; % mAb1 heavy chain + % mAb1 light chain + % Aflibercept main | 95 | NR | NR | 95 | NR | NR | 96 |

TABLE 40-continued

Research Stability of mAb1:aflibercept (120 mg/mL:40 mg/mL) Drug Product - Effect of Accelerated Conditions

| | | | | | | | | |
|---|---|---|---|---|---|---|---|---|
| Purity by SE-UPLC | | % Total HMW | 2.4 | 3.7 | 4.5 | 5.2 | 4.2 | 5.0 | 6.5 |
| | | % Total Native | 96.6 | 95.5 | 94.5 | 93.1 | 94.5 | 93.8 | 92.0 |
| | | % Total LMW | 1.1 | 0.8 | 1.1 | 1.7 | 1.4 | 1.2 | 1.6 |
| Charge Variant Analysis by iCIEF | mAb1 | % Acidic | 37.7 | 40.2 | 46.4 | 53.7 | 41.2 | 44.5 | 50.3 |
| | | % Main | 57.8 | 54.2 | 47.5 | 39.2 | 52.9 | 49.2 | 42.5 |
| | | % Basic | 4.5 | 5.6 | 6.2 | 7.1 | 5.9 | 6.3 | 7.2 |
| | Aflibercept | % Acidic | 19.5 | 18.8 | 20.5 | 23.1 | 20.2 | 20.4 | 22.5 |
| | | % Main | 77.9 | 79.0 | 77.7 | 75.0 | 77.7 | 77.1 | 75.5 |
| | | % Basic | 2.6 | 2.2 | 1.8 | 1.9 | 2.1 | 2.6 | 2.0 |
| Particulate Analysis by MFI (particles/mL) | | ≥2 μm | 3276 | NR | NR | 2701 | NR | NR | 953 |
| | | ≥10 μm | 145 | NR | NR | 55 | NR | NR | 38 |
| | | ≥25 μm | 15 | NR | NR | 3 | NR | NR | 3 |
| % Relative Potency by Bioassay | | mAb1 | 87 | NR | NR | 70 | NR | NR | 116 |
| | | Aflibercept | 109 | NR | NR | 108 | NR | NR | 79 |

TABLE 41

Research Stability of mAb1:aflibercept (10 mg/mL:40 mg/mL) Drug Product - Effect of Stress Conditions

| | |
|---|---|
| Formulation | 10 mg/mL mAb1, 40 mg/mL aflibercept, 10 mM sodium phosphate, pH 6.2, 40 mM sodium chloride, 0.03% (w/v) polysorbate 20, 5% (w/v) sucrose |
| Fill Volume | 0.5 mL |
| Container/Closure | 2 mL Type I borosilicate glass vial with West S2-F451 4432/50 GRY B2-40 stopper |

| | | No Stress | Agitation (minutes) | | Freeze/Thaw (Cycles) | |
|---|---|---|---|---|---|---|
| Assay | | 0 | 60 | 120 | 4 | 8 |
| Color and Appearance | | Pass | Pass | Pass | Pass | Pass |
| Turbidity (Increase in OD at 405 nm) | | 0.00 | 0.00 | 0.00 | 0.00 | 0.00 |
| pH | | 6.3 | 6.3 | 6.3 | 6.3 | 6.4 |
| % Total Recovered by RP-HPLC | mAb1 | 100 | 94 | 95 | 99 | 98 |
| | Aflibercept | 100 | 99 | 99 | 101 | 101 |
| Purity by SDS-PAGE | Non-reduced; % mAb1 main + % Aflibercept main | 99 | NR | 98 | NR | 98 |
| | Reduced; % mAb1 heavy chain + % mAb1 light chain + % Aflibercept main | 97 | NR | 98 | NR | 98 |
| Purity by SE-UPLC | % Total HMW | 1.6 | 1.5 | 1.5 | 1.6 | 1.6 |
| | % Total Native | 97.6 | 97.7 | 97.6 | 97.9 | 97.8 |
| | % Total LMW | 0.8 | 0.9 | 0.8 | 0.5 | 0.6 |
| Charge Variant Analysis by iCIEF | mAb1 % Acidic | 37.1 | 36.8 | 37.1 | 37.6 | 37.1 |
| | % Main | 58.1 | 58.5 | 58.7 | 58.3 | 58.6 |
| | % Basic | 4.8 | 4.7 | 4.2 | 4.1 | 4.3 |
| | Aflibercept % Acidic | 19.5 | 19.6 | 20.0 | 20.3 | 20.1 |
| | % Main | 77.5 | 77.3 | 76.8 | 76.5 | 76.7 |
| | % Basic | 3.0 | 3.1 | 3.2 | 3.2 | 3.2 |
| Particulate Analysis by MFI (particles/mL) | ≥2 μm | 4137 | NR | 3181 | NR | 2799 |
| | ≥10 μm | 103 | NR | 164 | NR | 55 |
| | ≥25 μm | 15 | NR | 21 | NR | 5 |
| % Relative Potency (Bioassay) | mAb1 | 124 | NR | 122 | NR | 130 |
| | Aflibercept | 125 | NR | 131 | NR | 136 |

TABLE 42

Research Stability of mAb1:aflibercept (120 mg/mL:40 mg/mL) Drug Product - Effect of Stress Conditions

| | |
|---|---|
| Formulation | 120 mg/mL mAb1, 40 mg/mL aflibercept, 10 mM sodium phosphate, pH 6.2, 40 mM sodium chloride, 0.03% (w/v) polysorbate 20, 5% (w/v) sucrose |
| Fill Volume | 0.5 mL |
| Container/Closure | 2 mL Type I borosilicate glass vial with West S2-F451 4432/50 GRY B2-40 stopper |

| | | | No Stress | Agitation (minutes) | | Freeze/Thaw (Cycles) | |
|---|---|---|---|---|---|---|---|
| Assay | | | 0 | 60 | 120 | 4 | 8 |
| Color and Appearance | | | Pass | Pass | Pass | Pass | Pass |
| Turbidity (Increase in OD at 405 nm) | | | 0.00 | 0.00 | 0.00 | 0.00 | 0.00 |
| pH | | | 6.3 | 6.3 | 6.3 | 6.3 | 6.4 |
| % Total Recovered by RP-HPLC | | mAb1 | 100 | 102 | 101 | 101 | 101 |
| | | Aflibercept | 100 | 100 | 100 | 103 | 103 |
| Purity by SDS-PAGE | | Non-reduced; % mAb1 main + % Aflibercept main | 97 | NR | 97 | NR | 97 |
| | | Reduced; % mAb1 heavy chain + % mAb1 light chain + % Aflibercept main | 95 | NR | 98 | NR | 98 |
| Purity by SE-UPLC | | % Total HMW | 2.4 | 2.3 | 2.3 | 2.5 | 2.6 |
| | | % Total Native | 96.6 | 96.9 | 97.0 | 96.7 | 96.7 |
| | | % Total LMW | 1.1 | 0.8 | 0.7 | 0.8 | 0.8 |
| Charge Variant Analysis by iCIEF | mAb1 | % Acidic | 37.7 | 37.3 | 37.5 | 37.5 | 37.6 |
| | | % Main | 57.8 | 58.2 | 57.9 | 57.9 | 57.9 |
| | | % Basic | 4.5 | 4.5 | 4.5 | 4.6 | 4.6 |
| | Aflibercept | % Acidic | 19.5 | 19.7 | 19.7 | 18.9 | 19.3 |
| | | % Main | 77.9 | 78.1 | 77.7 | 78.9 | 78.3 |
| | | % Basic | 2.6 | 2.2 | 2.6 | 2.3 | 2.4 |
| Particulate Analysis by MFI (particles/mL) | | ≥2 μm | 3276 | NR | 5403 | NR | 6448 |
| | | ≥10 μm | 145 | NR | 216 | NR | 189 |
| | | ≥25 μm | 15 | NR | 11 | NR | 11 |
| % Relative Potency (Bioassay) | | mAb1 | 87 | NR | 108 | NR | 57 |
| | | Aflibercept | 109 | NR | 114 | NR | 111 |

The results of the stability studies indicated that:

Formulated drug substance (FDS) 10:40 mg/mL mAb1:aflibercept is stable when stored at ≤−20° C. for at least 12 months FDS 120:40 mg/mL mAb1:aflibercept is stable when stored at ≤−20° C. for at least 12 months 10 mg/mL:40 mg/mL mAb1:aflibercept FDS was physically and chemically stable after 56 days of incubation at 5° C. or 28 days of incubation at 25° C./60% RH. No appreciable change in the physical or chemical stability was detected in any of the monitored attributes. Both mAb1 and aflibercept maintained potency when the 10 mg/mL:40 mg/mL FDS was incubated at 5° C. for 56 days or at 25° C./60% RH for 28 days.

120 mg/mL:40 mg/mL mAb1:aflibercept FDS was physically and chemically stable after 56 days of incubation at 5° C. No appreciable change in the physical or chemical stability was detected in any of the monitored attributes. 120 mg/mL:40 mg/mL FDS was physically stable after 28 days of incubation at 25° C./60% RH. No appreciable change in the physical or chemical stability was detected in any of the other monitored attributes. mAb1 and aflibercept both maintained potency when the 120 mg/mL:40 mg/mL FDS was incubated at 5° C. for 56 days or at 25° C./60% RH for 28 days.

10 mg/mL:40 mg/mL mAb1:aflibercept FDS was physically and chemically stable when agitated (vortexed at ambient temperature) for 120 minutes or when subjected to 8 freeze/thaw cycles (freezing at −30° C. and thawing at room temperature). No appreciable change in the physical or chemical stability was detected in any of the monitored attributes. mAb1 and aflibercept maintained potency when the 10 mg/mL:40 mg/mL FDS was agitated (vortexed at ambient temperature) for 120 minutes or when subjected to 8 freeze/thaw cycles (freezing at −30° C. and thawing at room temperature).

10 mg/mL:40 mg/mL mAb1:aflibercept FDS was physically and chemically stable when agitated (vortexed at ambient temperature) for 60 minutes or when subjected to 8 freeze/thaw cycles (freezing at −30° C. and thawing at room temperature). No appreciable change in the physical or chemical stability was detected in any of the monitored attributes. Although a 0.9% increase in high molecular weight species (SE-UPLC) was observed when FDS was agitated (vortexed at ambient temperature) for 120 minutes, no appreciable change was detected in any of the other monitored attributes. 120 minutes of vortex agitation is an extreme stress and agitation will be minimized for 120 mg/mL:40 mg/mL mAb1:aflibercept FDS during the manufacturing process. mAb1 and aflibercept maintained potency when the 10 mg/mL:40 mg/mL mAb1:aflibercept FDS was agitated (vortexed at ambient temperature) for 120 minutes or when subjected to 8 freeze/thaw cycles (freezing at −30° C. and thawing at room temperature).

Drug product (DP) 10:40 mg/mL mAb1:aflibercept is stable when stored at 2-8° C. for at least 9 months DP 120:40 mg/mL mAb1:aflibercept is stable when stored at 2-8° C. for at least 9 months.

Example 8: Methods Used to Assess Stability of Formulations

The research stability of mAb1 and mAb1:aflibercept FDS and DP were assessed using the following assays: Color and appearance by visual inspection; pH; Turbidity measured by increase in Optical Density (OD) at 405 nm; Subvisible particulate analysis on DP by Microflow Imaging (MFI); Protein concentration by reversed-phase high performance liquid chromatography (RP-HPLC).

Purity was assessed by the following assays: Size exclusion ultra performance liquid chromatography (SE-UPLC); Reduced and non-reduced sodium dodecyl sulfate polyacrylamide gel electrophoresis (SDS-PAGE).

Charge variant analysis was assessed by the following assays: Cation exchange UPLC (CEX-UPLC) for mAb1 FDS and DP; imaged capillary isoelectric focusing (iCIEF) for mAb1 and mAb1:aflibercept FDS and DP.

Potency was assessed by bioassays performed for mAb1 in the mAb1 formulation; and for both mAb1 and aflibercept in the mAb1:aflibercept formulation. The relative potency of each sample is determined using a bioassay and is defined as: ($IC_{50}$ Reference Sample/$IC_{50}$ Sample)*100%. The measured potency of storage stability samples must be within 50-150% of the measured potency of the reference standard.

The physical stability of a formulation refers to properties such as color, appearance, pH, turbidity and protein concentration. The presence of visible particulates in solution can be detected by visual inspection. A solution passes visual inspection if it is clear to slightly opalescent, essentially free from visible particulates, and colorless to pale yellow. Turbidity, measured by an increase in OD at 405 nm, can also be used to detect particulates in solution. An increase in OD at 405 nm may indicate the presence of particulates, an increase in opalescence, or color change of the test articles. MFI is used to measure subvisible particulates that are ≥2 μm in size. Protein concentration is measured by a RP-HPLC assay and reported as percent protein recovery relative to the starting material. In the RP-HPLC assay, a single mAb1 peak is resolved from a single aflibercept peak following elution from the reversed phase column. The mAb1 concentration is determined by comparing the mAb1 peak area to a calibration curve generated using a mAb1 standard whereas the aflibercept concentration is determined by comparing the aflibercept peak area to a calibration curve generated using an aflibercept standard. Percent recovery is calculated based on the measured mAb1 or aflibercept concentration relative to the starting mAb1 or aflibercept concentration, respectively.

Chemical stability refers to the formation of covalently modified forms (e.g. covalent aggregates, cleavage products or charge variant forms) and non-covalently modified forms (e.g. non-covalent aggregates) of protein. Higher and lower molecular weight degradation products can be separated from native molecular weight product using SE-UPLC and SDS-PAGE methods. The percentage of degraded mAb1 in the SE-UPLC method is calculated from the ratio of the area of all non-native peaks to the total area of all mAb1 peaks. mAb1 Purity by non-reduced and reduced SDS-PAGE is calculated from the ratio of main band intensity to the total intensity of all bands. Charge variant forms of mAb1 are resolved using iCIEF and CEX-UPLC. In these methods, peaks that are focused to a pI lower than that of the main peak are labeled "Acidic" peaks, whereas those focused to a pI higher than that of the main peak are labeled "Basic" peaks.

mAb1:aflibercept formulations are characterized using total molecular weight purity (native mAb1+native aflibercept) by SE-UPLC (i.e. molecular weight purity of mAb1 and aflibercept will not be determined individually), because mAb1 and aflibercept native species cannot be fully resolved from each other. Similarly, mAb1:aflibercept formulations will be characterized using total HMW species (mAb1 HMW+aflibercept HMW) and total LMW species (mAb1 LMW+aflibercept LMW), because mAb1 HMW species cannot be resolved from aflibercept HMW species and mAb1 LMW species cannot be resolved from aflibercept LMW species.

The percentage of total HMW species or total LMW species in mAb1:aflibercept, determined using the SE-UPLC method is calculated from the ratio of the area of total HMW species or total LMW species to the total area of all mAb1:aflibercept peaks, respectively. Purity by non-reduced and reduced SDS-PAGE is calculated from the ratio of (aflibercept main band+mAb1 main band) intensity to the total intensity of all bands. Aflibercept is a highly glycosylated protein that contains a high level of sialic acid. As a result of the complex charge distribution on aflibercept the CEX-UPLC method did not have sufficient resolution to separate all charge variant forms and was therefore not used to assay changes in the charge variant profile for the mAb1:aflibercept samples. Charge variant forms of mAb1 and aflibercept that are co-formulated within mAb1:aflibercept were resolved using iCIEF only.

For mAb1, peaks that are focused to a pI lower than that of the main peak are labeled "Acidic" peaks, whereas those focused to a pI higher than that of the main peak are labeled "Basic" peaks. For aflibercept, peaks 3-8 are the major peaks and are labeled "Main" peaks. Aflibercept peaks that are focused to a pI lower than that of peak 3 are labeled "Acidic" peaks, whereas those focused to a pI higher than that of peak 8 are labeled "Basic" peaks.

Example 9: Storage Stability Comparison of mAb1, mAb1:Aflibercept and Aflibercept Formulations SE-UPLC results from studies evaluating the storage stability of research formulations of 10 mg/mL mAb1, 120 mg/mL mAb1, and 40 mg/mL aflibercept were compared to results from the mAb1:aflibercept (10 mg/mL:40 mg/mL) and (120 mg/mL:40 mg/ml) co-formulations. This evaluation was performed to determine if co-formulating mAb1 and aflibercept resulted in differences in the relative amounts of high molecular weight species formed when compared to the individually formulated solutions of mAb1 and aflibercept (mono-formulations). The SE-UPLC results from the mono-formulations, incubated under equivalent conditions as the co-formulations, were used to calculate a theoretical increase in % HMW species for a co-formulation containing the same concentrations of each protein. The theoretical increase in HMW was compared to the increase in HMW observed when the actual co-formulated drug product was incubated at 5° C. The DS lots used for these studies are representative of the DS manufactured for clinical use.

A summary of the SE-UPLC results for formulations stored at 5° C. containing 10 mg/mL mAb1 alone, 40 mg/mL aflibercept alone, and the mAb1:aflibercept (10 mg/mL:40 mg/mL) co-formulation is as follows: After 9 months of storage at 5° C., the HMW content in the 10 mg/mL mAb1 formulation did not increase. Over the same assessment period the % HMW in the 40 mg/mL aflibercept formulation increased 0.4%. Based on the results from the 10 mg/mL mAb1 and 40 mg/mL aflibercept formulations an increase of 0.4% HMW species was predicted to occur over the 9 month assessment period in a mAb1:aflibercept (10 mg/mL:40 mg/mL) co-formulation. A 0.4% increase in total HMW species was observed for the mAb1:aflibercept (10 mg/mL:40 mg/mL) DP during the 9 month assessment period. The agreement between the calculated and observed increase in % HMW suggest that storage of mAb1 and aflibercept as mAb1:aflibercept (10 mg/mL:40 mg/mL) DP for 9 months at 5° C. did not lead to enhanced generation of HMW forms, relative to the increases observed for the individually formulated drug products.

A summary of the SE-UPLC results for formulations stored at 5° C. containing 120 mg/mL mAb1 alone, 40 mg/mL aflibercept alone, and the mAb1:aflibercept (120 mg/mL:40 mg/mL) co-formulation is as follows: After 9 months of storage at 5° C., the HMW content in the 120 mg/mL mAb1 formulation and the 40 mg/mL aflibercept formulations increased by 0.5% and 0.4%, respectively. Based on the results from the 120 mg/mL mAb1 and 40 mg/mL aflibercept formulation an increase of 0.9% HMW species was predicted to occur over the 9 month incubation period in a mAb1:aflibercept (120 mg/mL:40 mg/mL) co-formulation. This theoretical result was comparable to the 1.0% increase in total HMW species observed for the mAb1:aflibercept (120 mg/mL:40 mg/mL) DP during 9 months of storage at 5° C. The close agreement between the calculated and actual increases in % HMW suggest that storage of mAb1 and aflibercept as mAb1:aflibercept (120 mg/mL:40 mg/mL) DP for 9 months at 5° C. did not lead to enhanced generation of HMW forms, relative to the increases observed for the individually formulated drug products.

Example 10: Clinical Trial of Intravitreally (IVT) Administered mAb1 in Combination with Aflibercept in Patients with Either Neo-Vascular AMD or DME This study is a phase I, open-label, dose escalation clinical study designed to evaluate the safety, tolerability, and efficacy of IVT administration of mAb1 alone or in combination with aflibercept in patients with neovascular AMD or DME.

The primary objective of the study is to investigate the safety and tolerability of IVT mAb1 and aflibercept, and IVT mAb1 in patients with neovascular AMD, and separately in patients with DME.

The secondary objectives of the study are: (i) to characterize the systemic pharmacokinetics (PK) of mAb1 and aflibercept following IVT injection of mAb1 and aflibercept; and (ii) to characterize the presence of anti-mAb1 and anti-aflibercept antibodies following IVT injection.

The primary endpoint is the incidence and severity of ocular and systemic treatment-emergent adverse events (TE-AEs) through week 24 in patients treated with IVT mAb1 alone or with IVT co-formulated mAb1 and aflibercept.

The secondary endpoints are: (i) pharmacokinetics; and (ii) development of anti-drug antibodies (ADA) after IVT injection of the co-formulation.

The exploratory endpoints are: (1) change in BCVA from baseline; (2) change in central retinal thickness from baseline (measured by OCT) at week 12 and week 24; and (3) the number of PRN aflibercept injections from week 12 through week 20.

For AMD patients only: (i) change in CNV area from baseline (measured by FA) at week 12 and week 24; (ii) change in total lesion area from baseline (measured by FA) at week 12 and week 24; (iii) change in area of leakage from baseline (measured by FA) at week 12 and week 24.

For DME patients only: change in DRSS (measured by FP) from baseline at week 12 and week 24

Rationale for Study Design

Anti-VEGF therapy (e.g., aflibercept) is standard of care treatment for neovascular AMD and DME. Targeting both the VEGF and Angiopoeitin-2 (Ang-2) pathways in neovascular eye disease may result in additional efficacy over treatment with an anti-VEGF therapy alone, and also has the possibility of providing a longer duration of action resulting in a longer treatment interval. In a preclinical model of retinal neovascularization and chronic vascular leak induced by DL-AAA in rabbit, treatment with intravenous (IV) mAb1 (15 mg/kg) with IVT aflibercept (125 μg/50 μl) resulted in a suppression of vascular leak through week 8, compared to only week 3 with aflibercept alone (see details in Example 2).

In another study, the effect of mAb1 on retinal vascular development was compared to that of aflibercept, or to treatment with both mAb1 and aflibercept. Doses of mAb1 (25 mg/kg, subcutaneous [SC]) and aflibercept (25 mg/kg, SC) utilized in this experiment were in excess of the minimal doses required to obtain maximal suppression of retinal angiogenesis when each drug is used as a single agent. Administration of either mAb1 or aflibercept on P3 significantly reduced the mean vascularized area of the retina measured at P6 by 36% and 42%, respectively, relative to hFc controls. Moreover, the mean vascularized area of the retina was significantly smaller in the animals treated with both mAb1 and aflibercept, compared to animals treated with either agent alone, being reduced by 68%, representing a near complete arrest of retinal vascular development over the treatment period (see details in Example 3).

Rationale for Dose Selection

The starting dose is composed of a co-formulation of 0.5 mg mAb1:2 mg aflibercept, administered via IVT injection in the study eye. The 2 mg dose of aflibercept is equivalent to that presently approved and marketed for the treatment of wet AMD and central retinal vein occlusion.

The 0.5 mg:2 mg dose of the co-formulation is one-half of the lowest dose administered IVT bilaterally to cynomolgus monkeys during the Good Laboratory Practice toxicology study. Doses of up to 6 mg mAb1 in combination with 2 mg aflibercept, and 6 mg mAb1 alone were well-tolerated in the monkeys.

The rationale for this starting dose from a biologic standpoint is based on the DL-AAA model for neovascularization in the rabbit eye. In that model, a co-formulation of IVT aflibercept (0.125 mg) and mAb1 (0.5 mg) significantly increased the duration of anti-leak effects from 3 weeks to 8 weeks compared to aflibercept monotherapy. Extrapolating to the human eye (which is approximately 4 times larger than the rabbit eye) doses ranging from 0.5 mg to 0.6 mg would be expected to show biologic activity. Thus an initial dose of 0.5 mg is reasonable from a pharmacologic standpoint (see Example 2).

Safety of the proposed initial dose is supported by a 13-week IVT toxicology study in monkeys which utilized doses of mAb1 of 1, 3, and 6 mg in combination with 2 mg aflibercept bilaterally and included the 6 mg dose of mAb1 alone. Given that the volume of the human vitreous cavity is approximately 4 times that of the monkey vitreous cavity, the initial starting dose is effectively 8 times lower than the lowest dose in the monkey study, and approximately 48 times lower than the highest planned dose. Thus, the lowest dose used in the monkey IVT study provides an adequate safety margin for the proposed clinical starting dose.

Study Design

The study consists of a screening period (day −21 to day −1), a baseline visit (day 1), a treatment period (day 1 through day 57), follow-up (day 85 through day 141) and an end of study visit [day 169 (week 24)]. On day 1/baseline, eligible patients undergo safety assessments prior to receiving the first dose of study drug.

On day 1, day 29 and day 57, patients receive an injection of the co-formulation (mAb1 and aflibercept) or mAb1 alone for a total of 3 doses. The initial cohort receive the co-formulation at 0.5 mg:2 mg. Planned administration of the co-formulation and mAb1 alone is outlined in Table 43. If a maximum tolerated dose (MTD) is determined, the dose of mAb1 given alone will correspond to the highest dose of mAb1 administered within the co-formulation of mAb1 and aflibercept.

TABLE 43

Planned Dose Levels

| Cohort (n = 4-8) | IVT mAb1:aflibercept | IVT mAb1 |
|---|---|---|
| 1 | 0.5 mg:2 mg | |
| 2 | 1 mg:2 mg | |
| 3 | 3 mg:2 mg | |
| 4 | 6 mg:2 mg | |
| 5 | | 6 mg |

The last dose of study drug is administered at week 8. Intravitreal aflibercept injection (2 mg) is available to all patients beginning at week 12 for the study eye through week 20. Patients receiving aflibercept at week 12 will continue to receive aflibercept treatment with the possibility of up to monthly injections.

Patients are evaluated at study visits for ocular and systemic safety (including ophthalmic exams, laboratory assessments, etc.) and efficacy (optical coherence tomography [OCT], fluorescein angiography [FA]/fundus photography [FP], fundus autofluorescence [FAF] and BCVA using the 4-meter Early Treatment Diabetic Retinopathy Study [ETDRS] protocol), and are followed to week 24 (end of study).

Study Eye/Fellow Eye Selection:

Only 1 eye per patient is enrolled in the study. The enrolled eye will be designated as the study eye. The other eye is considered to be the fellow eye.

For patients who meet eligibility criteria in both eyes, the eye with the worse BCVA score is selected as the study eye. If a patient has similar BCVA scores in both eyes, the eye with the clearest media is selected as the study eye. If the ocular media of both eyes are similar in clarity, the patient's non-dominant eye (if identifiable) is selected as the study eye. If neither eye is dominant, the right eye is designated as the study eye.

Study Cohorts

Approximately 20 to 40 patients are enrolled in this dose escalation study. Four sequential ascending dose cohorts are planned for the co-formulated mAb1 and aflibercept (0.5 mg:2 mg, 1 mg:2 mg, 3 mg:2 mg, and 6 mg:2 mg) and 1 cohort is planned for mAb1 alone (6 mg). Each dose cohort initially consists of 4 patients, 2 DME and 2 AMD. If 1 dose limiting toxicity (DLT) occurs, the cohort can be expanded to include 2 additional DME patients and/or 2 additional AMD patients. Cohorts 4 and 5 can be run in parallel if cohort 4 is reached.

Dose Escalation and Study Stopping Rules

The decision to escalate to the next higher dose level of co-formulated mAb1 and aflibercept is based upon safety and tolerability information from both AMD and DME patients evaluated during the ongoing cohort and reviewed. The decision to escalate can take place after the last patient in a cohort (both AMD and DME) is observed for at least 1 week after receiving their first dose of study medication. The mAb1 alone cohort will be enrolled either at the MTD or the highest dose (6 mg), if an MTD is not identified. If an MTD is not identified, enrollment in this cohort will be concurrent with the 6 mg:2 mg mAb1: aflibercept co-formulation cohort.

If a DLT is observed, expansion of the cohort may be considered. Expansion of a cohort may involve 2 additional AMD patients and/or 2 additional DME patients. The rationale to increase the number of patients in each cohort beyond 4 following a DLT event is to enhance the ability to differentiate certain AEs that are known to occur sporadically with IVT injections (e.g., hypersensitivity responses or moderate to severe intraocular inflammation) from a true DLT event related to study drug exposure. Cohort expansion will not be automatic. Instead, the findings will be discussed to adjudicate the clinical significance of any potential DLT to determine if cohort expansion or dose escalation to the next higher dose level of the co-formulation will occur.

All patients are observed for at least 7 days after receiving co-formulated mAb1 and aflibercept before opening enrollment in the next dose cohort (although screening for the next dose cohort may begin prior to confirmation that the current dose is safe). Escalation to the next dose cohort will occur once all of the initial 4 patients enrolled in a cohort have completed day 8 (visit 7) safety assessments and the data have been reviewed. Please refer to Table 44 for the dose escalation and stopping rules.

TABLE 44

Dose Escalation and Stopping Rules

| No. of Patients with DLT(s) per Cohort | Action |
|---|---|
| 0 out of 4 | Escalate to the next dose level |
| 1 out of 4 patients with AMD or DME | Consider expanding the current dose level by 2 AMD patients and/or 2 DME patients up to a total of 8 patients |
| 1 out of 6 or 8 | Escalate to the next dose level |
| ≥2 in any cohort | Stop enrollment at the current dose level. |

If 2 or more DLTs are observed, dosing will be suspended until a safety review has been conducted. The outcome of the safety review will be a decision to: continue the study as planned, expand the current dose cohort, or stop dosing at the current dose. In this case, the observed toxicity will be considered to be dose-limiting, and the dose below the highest dose administered will be considered the MTD. If 1 grade 4 AE or grade 4 serious adverse event (SAE) is observed in any cohort (original dosing cohort or expansion cohort), dosing will be suspended and a comprehensive safety review will be conducted prior to consideration of further dosing.

Dose-Limiting Toxicities

A DLT is defined as the following: A grade 2 or 3 ocular toxicity as determined by the Ocular Toxicity Grading Scale or a grade 3 or 4 toxicity in the Food and Drug Administration (FDA) September 2007 Guidance for Industry, Toxicity Grading Scale for Healthy Adult and Adolescent Volunteers Enrolled in Preventive Vaccine Clinical Trials.

Maximum Tolerated Dose

The MTD is defined as the dose level immediately below the level at which dosing is stopped due to the occurrence of 2 or more DLTs. If the study is not stopped due to the occurrence of a DLT, it will be considered that the MTD has not been determined.

Study Population

The target population are men and women 50 years and older with neovascular AMD, or men and women 18 years and older with clinically significant DME with central involvement.

Inclusion Criteria:

A patient must meet the following criteria to be eligible for inclusion in the study: (1) For patients with AMD: a. active subfoveal choroidal neovascularization (CNV) secondary to AMD, including juxtafoveal lesions that affect the fovea as evidenced by FA or OCT in the study eye, as determined by the investigator; and b. Men or women ≥50 years and older. For patients with DME: c. Patients with clinically significant DME with central involvement (≥300 µm in the central subfield on spectral domain OCT); and d. Men or women ≥18 years and older. (2) Willing and able to comply with clinic visits and study-related procedures; and (3) Provide signed informed consent.

Exclusion Criteria:

A patient who meets any of the following criteria is excluded from the study: (1) (a) For patients with neovascular AMD: Evidence of CNV due to any cause other than AMD in either eye; Evidence of DR or DME in either eye; (b) For patients with DME: Evidence of neovascular AMD or CNV due to any cause in either eye; (2) Prior aflibercept in either eye; (3) IVT bevacizumab, ranibizumab, or pegaptanib sodium in the study eye within 8 weeks of day 1 or an AE with any of these previous treatments that would preclude administration of drug in this study; (4) Any prior treatment with angiopoietin inhibitors; (5) Any prior systemic (IV) anti-VEGF administration; (6) History of vitreoretinal surgery in the study eye; (7) Pan retinal laser photocoagulation or macular laser photocoagulation in the study eye within 3 months of the screening visit; (8) Previous use of intraocular or periocular corticosteroids in the study eye within 4 months of screening; (9) Intraocular pressure (IOP)≥25 mm Hg in the study eye at screening/baseline; (10) Evidence of infectious blepharitis, keratitis, scleritis, or conjunctivitis in either eye at screening/baseline; (11) Any intraocular inflammation/infection in either eye within 3 months of the screening visit; (12) Current iris neovascularization, vitreous hemorrhage, or tractional retinal detachment visible at the screening visit in the study eye; (13) Inability to obtain photographs, FA, or OCT to document CNV, eg, due to media opacity, allergy to fluorescein dye or lack of venous access at screening/baseline; (14) Uncontrolled diabetes mellitus, in the opinion of the investigator; (15) Uncontrolled blood pressure (defined as systolic >160 mm Hg or diastolic >95 mm Hg while patient is sitting); (16) History of cerebrovascular accident or myocardial infarction within 180 days of day 1; (17) Renal failure, dialysis, or history of renal transplant; (18) Known sensitivity to doxycycline or similar compound (ie, tetracyclines); (19) Known sensitivity to any of the compounds of the study formulation; (20) Pregnant or breastfeeding women; and (210 Sexually active men or women of childbearing potential who are unwilling to practice adequate contraception during the study (adequate contraceptive measures include stable use of oral contraceptives or other prescription pharmaceutical contraceptives for 2 or more menstrual cycles prior to screening; intrauterine device; bilateral tubal ligation; vasectomy; condom plus contraceptive sponge, foam, or jelly, or diaphragm plus contraceptive sponge, foam, or jelly).

Study Treatments

Investigational and Reference Treatments

Co-formulated mAb1 and aflibercept is a drug product that is composed of mAb1 (anti-Ang2 antibody) and aflibercept. It will be supplied for this study as an aqueous solution in sterile, single-use 2 mL glass vials for IVT administration, in the following concentrations (with progressively higher concentrations to be used for the progressively higher doses in dose escalation): 10:40 mg/mL, 20:40 mg/mL; 60:40 mg/mL; and 120:40 mg/mL (mAb1:aflibercept).

The mAb1 alone drug product is also supplied for this study as an aqueous solution in sterile, single-use 2 mL glass vials for IVT administration, at a concentration of 120 mg/mL.

The co-formulation and mAb1 is delivered via IVT injection and the injection volume will be 50 µl (0.05 cc). There will be a 0.050 ml minimum withdrawable content. Each vial contains a withdrawable volume of 0.3 mL of mAb1.

Patients will be given 3 doses of study drug. Study drug is administered on day 1, day 29 and day 57 by the investigator, or other qualified study personnel. Patients are enrolled in order to receive one of the following co-formulation or mAb1 treatment regimens:

cohort 1: 0.5 mg:2 mg (mAb1: aflibercept)
cohort 2: 1 mg:2 mg (mAb1: aflibercept)
cohort 3: 3 mg:2 mg (mAb1: aflibercept)
cohort 4: 6 mg:2 mg (mAb1: aflibercept)
cohort 5: 6 mg (mAb1 alone)

Background Treatments

Study Eye Treatment:

Intravitreal aflibercept injections are supplied in sterile, sealed vials with a volume sufficient to prepare a syringe with 50 uL at a concentration of 40 mg/mL. Beginning at week 12 (and continuing through week 20), patients will be eligible to receive monthly aflibercept treatment (2 mg) in the study eye, if any of the re-treatment criteria listed below are satisfied: (1) There is a >50 µm increase in central retinal thickness on OCT compared to the lowest previous measurement. (2) There are new or persistent cystic retinal changes or subretinal fluid on OCT, or persistent diffuse edema in the central subfield on OCT. (3) A loss of 5 or more letters from the best previous measurement in conjunction with any increase in retinal thickness in the central subfield on OCT. (4) An improvement of BCVA between the current and most recent visit of letters.

Fellow Eye Treatment:

At week 4, aflibercept (2 mg) will be made available to patients with AMD or DME in the fellow eye at screening, or who are diagnosed with AMD or DME during the trial. The fellow eye will be assessed for safety during the trial, but will not be considered a study eye. The patient's fellow eye may, at the discretion of the investigator, receive treatment on the same day as the treatment of the study eye. All fellow eye treatments must be recorded on the electronic case report form (CRF) as a procedure for the fellow eye.

Patients who receive treatment for the fellow eye will not be required to be withdrawn from the study. Study assessments and all AEs for the fellow eye will be collected.

Prohibited Medications

Study Eye:

Patients may not receive any standard or investigational agents for AMD or DME treatment in the study eye other than their assigned study treatment with IVT co-formulation or IVT mAb1, and, if needed, aflibercept, as specified in this protocol. This includes medications administered locally (eg, IVT, topical, juxtascleral or periorbital routes), as well as those administered systemically, with the intent of treating neovascular AMD or DME in the study eye.

Fellow Eye:

Starting at week 4, if the fellow eye has DME involving or threatening the center of the macula or neo-vascular AMD, aflibercept (2 mg) may be administered. Other conditions in the fellow eye may be treated with approved therapies; however they must be administered locally.

Non-Ocular Systemic:

Non-ocular (systemic) standard or investigational treatments for neo-vascular AMD and DME of the study or fellow eye are not permitted. Systemic anti-angiogenic agents will not be permitted during the study.

Study Procedures

Safety and tolerability is assessed by monitoring/evaluation of treatment-emergent adverse events (TEAEs), physical examinations, vital signs, electrocardiograms (ECGs), and clinical evaluations (hematology, blood chemistry and urinalysis). Ocular safety is assessed by ophthalmic examinations (slit lamp, indirect ophthalmoscopy, intraocular pressure [IOP], spectral domain OCT, BCVA, FAF and information from FP and FA. Serum samples will be collected for assessing mAb1 and plasma PK samples for aflibercept. Serum samples to assess ADA responses will be collected.

Best Corrected Visual Acuity (BCVA):

Visual function of the study eye and the fellow eye is assessed using the 4M ETDRS protocol (The Early Treatment Diabetic Retinopathy Study Group 1985) at 4 meters at each study visit at screening, baseline, and week 1, 4, 6, 8, 12, 16, 20 and 24 after treatment.

Fluorescein Angiography/Fundus Photography (FA/FP):

The anatomical state of the retinal vasculature of the study eye and the fellow eye is evaluated by funduscopic examination, FA, and FP at time points each study visit at screening, baseline, and week 1, 4, 6, 8, 12, 16, 20 and 24 after treatment. At a minimum, information on the following variables will be collected:

For AMD only: total lesion area, CNV area, classic CNV area, and area of fluorescein leakage.

For DME only: Diabetic Retinopathy Severity Score (DRSS).

Certified photographers will perform FA and FP in both eyes at the time points listed above. Fundus and angiographic images are sent to the independent reading center. The study eye will be the transit eye. All FA and FP will be archived at the site as part of the source documentation.

Spectral Domain Optical Coherence Tomography:

Retinal and lesion characteristics are evaluated using spectral domain OCT at time points each study visit at screening, baseline, and week 1, 4, 6, 8, 12, 16, 20 and 24 after treatment.

Images are captured and transmitted at the study site by OCT technicians using spectral domain OCT for the study eye and fellow eye. Optical coherence tomography images are sent to the independent reading center where images for the study eye will be read. All OCTs will be electronically archived at the study sites as part of the source documentation. Optical coherence tomography technicians will be certified by the reading center to ensure consistency and quality in image acquisition and will be masked to patients' dose level of the co-formulation.

Fundus Autofluorescence:

Anatomic characteristics of the retina are also evaluated using autofluorescence. Certified photographers will perform FAF at time points each study visit at screening, baseline, and week 1, 4, 6, 8, 12, 16, 20 and 24 after treatment. Images will be sent to the independent reading center. All images will be archived at the site as part of the source documentation.

Intraocular Pressure:

Intraocular pressure of the study eye is measured at each study visit, using Goldmann applanation tonometry or Tonopen™. The same method of IOP measurement must be used in each patient throughout the study. On visits where an aflibercept treatment is given, IOP must be measured pre-treatment (bilateral) and at approximately 30 minutes post-treatment (study eye only).

Slit Lamp Examination:

The anterior segment and the anterior vitreous is examined using a slit lamp at time points each study visit at screening, baseline, and week 1, 4, 6, 8, 12, 16, 20 and 24 after treatment. Both eyes are examined. Examination of the fundus is also conducted by indirect ophthalmoscopy.

Anterior chamber flare and cells are graded. The intensity of the cellular reaction in the anterior chamber is graded according to the number of inflammatory cells seen in a 1×3-mm high-powered beam at full intensity at a 45° to 60° angle. In addition, vitreal inflammatory response is graded.

Indirect Ophthalmoscopy:

Indirect ophthalmoscopy is performed at time points each study visit at screening, baseline, and week 1, 4, 6, 8, 12, 16, 20 and 24 after treatment. It will be performed bilaterally predose, and in the study eye immediately after administration of study drug on days when study drug is administered. The appropriate lenses and optics are used, ie, a head mounted or handheld ophthalmoscope for the periphery, and a slit lamp for the central fundus. The pupil is dilated, and examination of the fundus is done on both eyes.

Safety Non-Ocular:

Vital signs, including temperature, sitting blood pressure, pulse, and respiration is collected, a complete and thorough physical examination, a standard 12-lead ECG as well as standard laboratory testing for hematology, chemistry, urinalysis, and pregnancy testing will be carried out predose at time points each study visit at screening, baseline, and week 1, 4, 6, 8, 12, 16, 20 and 24 after treatment.

Safety

Safety and tolerability is assessed by monitoring/evaluation of treatment-emergent adverse events (TEAEs), physical examinations, vital signs, electrocardiograms (ECGs), and clinical evaluations (hematology, blood chemistry and urinalysis).

An adverse event (AE) is any untoward medical occurrence in a patient administered a study drug which may or may not have a causal relationship with the study drug. Therefore, an AE is any unfavorable and unintended sign (including abnormal laboratory finding), symptom, or disease which is temporally associated with the use of a study drug, whether or not considered related to the study drug.

A serious adverse event (SAE) is any untoward medical occurrence that at any dose: results in death, is life-threatening, requires in-patient hospitalization or prolongation of existing hospitalization, results in persistent or significant disability/incapacity, is a congenital anomaly/birth defect, and/or is an important medical event. Criteria for serious sight-threatening ocular AEs include the following: (1) AE causes a decrease in BCVA of >30 letters (compared with the most recent assessment of BCVA). (2) AE causes a decrease in VA to the level of light perception or worse. (3) AE requires surgical intervention (e.g., vitreous tap or biopsy with IVT injection of anti-infectives, laser or retinal cryopexy with gas) to prevent permanent loss of sight. (4) AE is associated with severe intraocular inflammation (ie, 4+anterior chamber cell/flare or 4+vitritis). (5) In the opinion of the investigator, AE may require medical intervention to prevent permanent loss of sight.

Results

Preliminary analysis of safety results indicated that the co-formulation was well tolerated in both AMD and DME patients with a favorable safety profile.

Tables 45 and 46 show the baseline demographics of patients with AMD and DME respectively.

TABLE 45

Baseline demographics in AMD patients

|  | Cohort 1<br>0.5 mg:2 mg<br>(N = 2) | Cohort 2<br>1 mg:2 mg<br>(N = 2) | Cohort 3<br>3 mg:2 mg<br>(N = 2) | Cohort 4<br>6 mg:2 mg<br>(N = 2) | Cohort 5<br>6 mg mAb1<br>(N = 4) | Overall<br>(N = 10) |
|---|---|---|---|---|---|---|
| Age | | | | | | |
| Years | 82 | 71 | 72 | 78 | 76 | 76 |
| Min:Max | 78:86 | 61:81 | 57:87 | 78:79 | 64:89 | 57:89 |
| Gender, n (%) | | | | | | |
| Female | 1 | 1 | 1 | 0 | 1 | 4 (40%) |
| Male | 1 | 1 | 1 | 2 | 1 | 6 (60%) |
| Race, n (%) | | | | | | |
| White | 2 | 2 | 2 | 2 | 2 | 10 (100%) |
| Black | 0 | 0 | 0 | 0 | 0 | 0 |
| Asian | 0 | 0 | 0 | 0 | 0 | 0 |

TABLE 46

Baseline demographics in DME patients

|  | Cohort 1<br>0.5 mg:2 mg<br>(N = 2) | Cohort 2<br>1 mg:2 mg<br>(N = 2) | Cohort 3<br>3 mg:2 mg<br>(N = 2) | Cohort 4<br>6 mg:2 mg<br>(N = 2) | Cohort 5<br>6 mg<br>REGN910<br>(N = 2) | Overall<br>(N = 10) |
|---|---|---|---|---|---|---|
| Age | | | | | | |
| years | 66 | 55 | 66 | 61 | 57 | 61 |
| Min:Max | 56:77 | 54:57 | 65:68 | 55:67 | 57:58 | 54:77 |
| Gender, n (%) | | | | | | |
| Female | 1 | 2 | 2 | 1 | 1 | 7 (70%) |
| Male | 1 | 0 | 0 | 1 | 1 | 3 (30%) |
| Race, n (%) | | | | | | |
| White | 2 | 0 | 2 | 1 | 2 | 7 (70%) |
| Black | 0 | 1 | 0 | 1 | 0 | 2 (20%) |
| Asian | 0 | 1 | 0 | 0 | 0 | 1 (10%) |

The baseline characteristics of AMD and DME patients are summarized in Tables 47 and 48, respectively.

TABLE 47

Baseline characteristics of AMD patients

| | |
|---|---|
| N (All Cohorts) | 10 |
| BCVA | 61.7 (12.41) |
| Min:Max | 35:76 |
| IOP | 17.0 (3.40) |
| Min:Max | 10:22 |
| CRT(μm) | 415.6 (105.69) |
| Min:Max | 263:621 |

TABLE 48

Baseline characteristics of DME patients

| | |
|---|---|
| N (All Cohorts) | 10 |
| BCVA | 59.7 (11.92) |
| Min:Max | 31:75 |
| IOP | 14.9 (3.14) |
| Min:Max | 9:20 |
| CRT(μm) | 453.6 (129.87) |
| Min:Max | 310:689 |

Results to date (at 12 weeks) demonstrate improvement in vision (increase in visual acuity of up to 20 letters) and retinal morphology (decrease in central subfield thickness) at all dose levels. Duration of effect was extended at higher doses (for the 3 mg:2 mg and 6 mg:2 mg doses).

At 24 weeks after treatment, it is expected that the visual acuity gains will be maintained or improved in patients with AMD or DME.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for treating a vascular eye disease or disorder, in a human subject in need thereof, comprising intravitreally administering 2 mg aflibercept and 6 mg nesvacumab in a pharmaceutical composition comprising
   (i) 40 mg/ml of aflibercept;
   (ii) 120 mg/ml of nesvacumab;
   (iii) a sodium phosphate buffer at pH of 6.2±0.3;
   (iv) polysorbate 20;
   (v) sodium chloride; and
   (vi) sucrose,
   to the subject.

2. The method of claim 1, wherein the pharmaceutical composition is administered to the subject every 4 weeks.

3. The method of claim 1, wherein the eye disease or disorder is selected from the group consisting of diabetic retinopathy, diabetic macular edema, age-related macular degeneration, retinal neovascularization, central retinal vein occlusion, branched retinal vein occlusion, polypoidal choroidal vasculopathy, and choroidal neovascularization.

4. The method of claim 3, wherein the eye disease or disorder is age-related macular degeneration.

5. The method of claim 3, wherein the eye disease or disorder is diabetic macular edema.

6. A method for inhibiting retinal angiogenesis, inhibiting retinal neovascularization, inhibiting vascular leak and/or suppressing vascular leak, in a human subject in need thereof, comprising intravitreally administering 2 mg aflibercept and 6 mg nesvacumab in a pharmaceutical composition comprising
   (i) 40 mg/ml of aflibercept;
   (ii) 120 mg/ml of nesvacumab;
   (iii) a sodium phosphate buffer at pH of 6.2±0.3;
   (iv) polysorbate 20;
   (v) sodium chloride; and
   (vi) sucrose,
   to the subject.

7. The method of claim 6, wherein the retinal angiogenesis, retinal neovascularization, or vascular leak is associated with an eye disease or disorder selected from the group consisting of diabetic retinopathy, diabetic macular edema, age-related macular degeneration, retinal neovascularization, central retinal vein occlusion, branched retinal vein occlusion, polypoidal choroidal vasculopathy, and choroidal neovascularization.

8. The method of claim 6, wherein the pharmaceutical formulation is intravitreally administered to the subject every 4 weeks.

9. A method for treating diabetic macular edema, in a human subject diagnosed with diabetic macular edema, comprising:
   every four weeks intravitreally administering 2 mg aflibercept and 6 mg nesvacumab in a pharmaceutical composition comprising
   (i) 40 mg/ml of aflibercept;
   (ii) 120 mg/ml of nesvacumab;
   (iii) a sodium phosphate buffer at pH of 6.2±0.3;
   (iv) polysorbate 20;
   (v) sodium chloride; and
   (vi) sucrose,
   to the subject.

* * * * *

SEQUENCE LISTING

<160> NUMBER OF SEQ ID NOS: 11

<210> SEQ ID NO 1
<211> LENGTH: 122
<212> TYPE: PRT
<213> ORGANISM: Artificial Sequence
<220> FEATURE:
<223> OTHER INFORMATION: synthetic

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Ile His Trp Val Arg Gln Ala Thr Gly Lys Gly Leu Glu Trp Val
        35                  40                  45

Ser Ala Ile Gly Pro Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Leu Ile Thr Phe Gly Gly Leu Ile Ala Pro Phe Asp Tyr Trp
            100                 105                 110

Gly Gln Gly Thr Leu Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: synthetic

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Asp Asn Ser Gln
                85                  90                  95

Thr Phe Gly Gln Gly Thr Lys Val Glu Ile Lys
            100                 105

<210> SEQ ID NO 3
<211> LENGTH: 8
<212> TYPE: PRT
<213> ORGANISM: Artificial Sequence
<220> FEATURE:
<223> OTHER INFORMATION: synthetic

<400> SEQUENCE: 3

Gly Phe Thr Phe Ser Ser Tyr Asp
1               5

<210> SEQ ID NO 4
<211> LENGTH: 7
<212> TYPE: PRT
<213> ORGANISM: Artificial Sequence
<220> FEATURE:
<223> OTHER INFORMATION: synthetic

<400> SEQUENCE: 4

Ile Gly Pro Ala Gly Asp Thr
1               5

<210> SEQ ID NO 5
<211> LENGTH: 16
<212> TYPE: PRT
<213> ORGANISM: Artificial Sequence
<220> FEATURE:
<223> OTHER INFORMATION: synthetic

<400> SEQUENCE: 5

Ala Arg Gly Leu Ile Thr Phe Gly Gly Leu Ile Ala Pro Phe Asp Tyr
1               5                   10                  15

<210> SEQ ID NO 6
<211> LENGTH: 7
<212> TYPE: PRT
<213> ORGANISM: Artificial Sequence
<220> FEATURE:
<223> OTHER INFORMATION: synthetic

<400> SEQUENCE: 6

Gln Ser Val Ser Ser Thr Tyr
1               5

<210> SEQ ID NO 7
<211> LENGTH: 3
<212> TYPE: PRT
<213> ORGANISM: Artificial Sequence
<220> FEATURE:
<223> OTHER INFORMATION: synthetic

<400> SEQUENCE: 7

Gly Ala Ser
1

<210> SEQ ID NO 8
<211> LENGTH: 8
<212> TYPE: PRT
<213> ORGANISM: Artificial Sequence
<220> FEATURE:
<223> OTHER INFORMATION: synthetic

<400> SEQUENCE: 8

Gln His Tyr Asp Asn Ser Gln Thr
1               5

<210> SEQ ID NO 9
<211> LENGTH: 452
<212> TYPE: PRT
<213> ORGANISM: Artificial Sequence
<220> FEATURE:
<223> OTHER INFORMATION: synthetic

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Ile His Trp Val Arg Gln Ala Thr Gly Lys Gly Leu Glu Trp Val
            35                  40                  45

Ser Ala Ile Gly Pro Ala Gly Asp Thr Tyr Tyr Pro Gly Ser Val Lys
 50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
            85                  90                  95

Arg Gly Leu Ile Thr Phe Gly Gly Leu Ile Ala Pro Phe Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
 130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
 210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
 290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu

```
                   435                 440                 445

Ser Pro Gly Lys
        450

<210> SEQ ID NO 10
<211> LENGTH: 214
<212> TYPE: PRT
<213> ORGANISM: Artificial Sequence
<220> FEATURE:
<223> OTHER INFORMATION: synthetic

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Asp Asn Ser Gln
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 458
<212> TYPE: PRT
<213> ORGANISM: Artificial Sequence
<220> FEATURE:
<223> OTHER INFORMATION: synthetic

<400> SEQUENCE: 11

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60
```

-continued

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
            245                 250                 255

Lys Pro Lys Asp Thr Leu Met Ile Ser Arg Thr Pro Glu Val Thr Cys
        260                 265                 270

Val Val Val Asp Val Ser His Glu Asp Pro Glu Val Lys Phe Asn Trp
    275                 280                 285

Tyr Val Asp Gly Val Glu Val His Asn Ala Lys Thr Lys Pro Arg Glu
290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
            325                 330                 335

Lys Ala Leu Pro Ala Pro Ile Glu Lys Thr Ile Ser Lys Ala Lys Gly
        340                 345                 350

Gln Pro Arg Glu Pro Gln Val Tyr Thr Leu Pro Pro Ser Arg Asp Glu
    355                 360                 365

Leu Thr Lys Asn Gln Val Ser Leu Thr Cys Leu Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Tyr Ser Lys Leu Thr Val Asp Lys Ser Arg Trp Gln Gln Gly Asn
        420                 425                 430

Val Phe Ser Cys Ser Val Met His Glu Ala Leu His Asn His Tyr Thr
    435                 440                 445

Gln Lys Ser Leu Ser Leu Ser Pro Gly Lys
450                 455